US005759833A

United States Patent [19]
Shiba et al.

[11] Patent Number: 5,759,833
[45] Date of Patent: Jun. 2, 1998

[54] HUMAN ISOLEUCYL-TRNA SYNTHETASE PROTEINS, NUCLEIC ACIDS AND TESTER STRAINS COMPRISING SAME

[75] Inventors: Kiyotaka Shiba, Tokyo, Japan; Janice E. Kranz, Boston; Paul R. Schimmel, Cambridge, both of Mass.

[73] Assignees: Cubist Pharmaceuticals, Inc., Cambridge, Mass.; Cancer Institute, Japanese Foundation for Cancer Research, Tokyo, Japan

[21] Appl. No.: 468,557

[22] Filed: Jun. 6, 1995

Related U.S. Application Data

[63] Continuation-in-part of Ser. No. 250,852, May 27, 1994, abandoned.
[51] Int. Cl.$^6$ .............................. C12N 9/00; C12N 15/00; C12N 1/14; C07H 21/04
[52] U.S. Cl. ................. 435/183; 435/252.3; 435/254.11; 435/254.21; 435/320.1; 435/325; 536/23.2
[58] Field of Search .......................... 435/252.3, 254.11, 435/320.1, 183; 536/23.2

[56] References Cited

U.S. PATENT DOCUMENTS

| | | | |
|---|---|---|---|
| 4,713,337 | 12/1987 | Jasin et al. | 435/172.3 |
| 4,952,501 | 8/1990 | Jasin et al. | 435/69.2 |
| 4,963,487 | 10/1990 | Schimmel | 435/172.3 |
| 5,338,669 | 8/1994 | Gillies | 435/69.1 |
| 5,484,703 | 1/1996 | Raben et al. | 435/7.4 |
| 5,527,668 | 6/1996 | Kawasaki et al. | 435/6 |
| 5,561,054 | 10/1996 | Kron et al. | 435/69.1 |

FOREIGN PATENT DOCUMENTS

WO 95/09927  4/1995  WIPO.

OTHER PUBLICATIONS

Georgiou, G. (1988) AIChE J. 34(8):1233–1248.
Nichols, R.C. (1994) Genbank Accession U04953.
Shiba, K. (1994) Genbank Accession D28473.
Nichols, Ralph C., et al., "Human isoleucyl–tRNA Synthetase:Sequence of the CDNA, Alternative mRNA Splicing, and the Characteristics of an Unusually Long C–Terminal Extension," *Gene*, 155:299–304 (1995).
Shiba, K., et al., "Isolation of Higher Eukaryote Aminoacyl–tRNA Synthetase Genes by an Alignment–Guided Cross–Species PCR: Application to Human Isoleucine tRNA Synthetase," [From *Programme and Abstracts*, p. F.46], 15th International tRNA Workshop, Socieété Francaise de Biochimie et Biologie Moléculaire, Cap d'Agde, France, May 30–Jun. 4 (1993), Abstract No. 364. Printout of a computer record of parts of a poster presented at Cap d'Agde, France, May 30–Jun. 4, 1993, 15th International tRNA Workshop, Société Francaise de Biochimie et Biologie Moléculaire.

Sequence of Human Isoleucyl–tRNA Synthetase Gene. GenBank Name: HSU04953, Accession: U04953, National Center for Biotechnology Information Seq ID: 450850. Entered by Nichols, R. C., et al. First Available: Jan. 13, 1994; Updated: Jan. 26, 1994.
Hughes, J., et al., "Inhibition of Isoleucyl–Transfer Ribonucleic Acid Synthetase in *Escherichia coli* by Pseudomonic Acid," *Biochem. J.* 176:305–318 (1978), Great Britain.
Webster, T., et al., "Specific Sequence Homology and Three–Dimensional Structure of an Aminoacyl Transfer RNA Synthetase," *Science* 226:1315–1317, Dec. 1984.
Tsui, F. W. L., et al., "Isolation, structure and expression of mammalian genes for histidyl–tRNA synthetase," *Nucleic Acids Research* 15:3349–3367 (1987).
Edwards, H., et al., "An *E. coli* Aminoacyl–tRNA Synthetase Can Substitute for Yeast Mitochondrial Enzyme Function In Vivo," *Cell* 51:643–649, Nov. 20, 1987.
Englisch, U., et al., "Structure of the Yeast Isoleucyl–tRNA Synthetase Gene (ILS1)," *Biol. Chem. Hoppe–Seyler* 368:971–979, Aug. 1987.
Martindale, D. W., et al., "Isolation and complete sequence of the yeast isoleucyl–tRNA synthetase gene (ILS1)," *Current Genetics* 15:99–106 (1989).
Jacobo–Molina, A., et al., "cDNA Sequence, Predicted Primary Structure, and Evolving Amphiphilic Helix of Human Aspartyl–tRNA Synthetase," *The Journal of Biological Chemistry* 264:16608–16612, Oct. 5, 1989.
Fett, R., et al., "The Primary Structure of Human Glutaminyl–tRNA Synthetase," *The Journal of Biological Chemistry* 266(3):1448–1455, Jan. 25, 1991.

(List continued on next page.)

*Primary Examiner*—Robert A. Wax
*Assistant Examiner*—Lisa J. Hobbs
*Attorney, Agent, or Firm*—Hamilton, Brook, Smith & Reynolds, P.C.

[57] ABSTRACT

Isolated, recombinant nucleic acids which encode an isoleucyl-tRNA synthetase (IleRS) of human origin have been used to make expression constructs and transformed host cells for the production of a recombinant human IleRS. A recombinant enzyme has been purified, and is active in the specific aminoacylation of tRNA by isoleucine. Isolated, recombinant enzyme, and antibodies made specifically thereto, can be useful in assays to diagnose and monitor the autoimmune disease known as "antisynthetase syndrome." The essential isoleucyl-tRNA synthetases of microbes pathogenic in humans can be the targets of inhibitory agents having antimicrobial activity. A human isoleucyl-tRNA synthetase, isolated and purified, can be used to assess the toxic effect in humans of such an inhibitory agent in various biochemical activity assays. This human enzyme can also be expressed in "tester strains," whose cells rely upon the function of the human isoleucyl-tRNA synthetase for tRNA$^{Ile}$ charging. Such tester strains can be used to test for any toxic effects of an antimicrobial agent that specifically interacts with a heterologous human IleRS gene or gene product.

21 Claims, 3 Drawing Sheets

OTHER PUBLICATIONS

Cruzen, M. E., et al., "Nucleotide and Deduced Amino Acid Sequence of Human Threonyl–tRNA Synthetase Reveals Extensive Homology to the *Escherichia coli* and Yeast Enzymes," *The Journal of Biological Chemistry* 266(15):9919–9923, May 25, 1991.

Jenal, U., et al., "Isoleucyl–tRNA Synthetase of *Methanobacterium thermautotrophicum* Marburg," *The Journal of Biological Chemistry* 266(16):10570–10577, Jun. 5, 1991.

Racher, K. L., et al., "Expression and Characterization of a Recombinant Yeast Isoleucyl–tRNA Synthetase," *The Journal of Biological Chemistry* 266(26):17158–17164, Sep. 15, 1991.

Csank, C., et al., Isoleucyl–tRNA Synthetase from the Ciliated Protozoan *Tetrahymena thermophila*, *The Journal of Biological Chemistry* 267(7):4592–4599, Mar. 5, 1992.

Vilalta, A., et al., "Cloning, sequencing and expression of a cDNA encoding mammalian valyl–tRNA synthetase," *Gene*, 123:181–186 (1993).

Frolova, L. Y., et al., "The human gene encoding tryptophanyl–tRNA synthetase: interferon–response elements and exon–intron organization," *Gene*, 128:237–245 (1993).

Shiba, K., et al., "Human cytoplasmic isoleucyl–tRNA synthetase: Selective divergence of the anticodon–binding domain and acquisition of a new structural unit," *Proc. Natl. Acad. Sci. USA*, 91:7435–7439, Aug. 1994.

Raben, N., "Improved Assay Using Recombinant Histidyl–tRNA Synthetase," *U.S. Department of Commerce National Technical Information Service*, Report No. PAT–APPL–8–052 404, 22 Apr. 1993.

Targoff, I. N., "Autoantibodies to Aminoacyl–Transfer RNA Synthetases for Isoleucine and Glycine," *The J. of Immunol.* 144(5):1737–1743, Mar. 1, 1990.

Raben, N., "A Motif in Human Histidyl–tRNA Synthetase Which Is Shared among Several Aminoacyl–tRNA Synthetases Is a Coiled–coil That Is Essential for Enzymatic Activity and Contains the Major Autoantigenic Epitope," *The J. of Bio. Chem.* 269(39):24277–24283, Sep. 30, 1994.

Friedrich von der Haar, et al., "Target Directed Drug Synthesis: The Aminoacyl–tRNA Synthetase as Possible Targets," *Angew. Chem. Int. Ed.*, 20(3):217–223 (Mar. 1981).

Chalker, A. F., et al., "Analysis and Toxic Overexpression in *Escherichia coli* of a Straphylococcal Gene Encoding Isoleucyl–tRNA Synthetase," *Gene*, 141: 103–108 (1994).

Walter, R.D. and Kuhlow, F., "Parasite–Specific Interaction of N–[4–(4' nitroanilino) –phenyl]–S–(β–carboxyethyl) – dithiocarbamic acid–ester with Arginyl–tRNA–Synthetase from *Dirofilaria immitis*," *Trop. Med. Parasit.*, 36: 230–232 (1985).

Jasin, M. and Schimmel, P., "Deletion of an Essential Gene in *Escherichia coli* by Site–Specific Recombination with Linear DNA Fragments," *Journal of Bacteriology*, 159(2):783–786 (1984).

Edwards, Helen and Schimmel, P., "A Bacterial Amber Suppressor in *Saccharomyces cerevisiae* Is Selectively Recognized by a Bacterial Aminoacyl–tRNA Synthetase," *Molecular and Cellular Biology*, 10(4):1633–1641 (1990).

Meinnel, T., et al., "Aminoacyl–tRNA Synthetases: Occurrence, Structure, and Function." In *tRNA; Structure, Biosynthesis, and Function*, D. Söll, et al., eds. (Washington, DC: American Society for Microbiology), pp. 251–300 (1995).

Hughes, J. and Mellows, G., "Interaction of Pseudomonic Acid A with *Escherichia coli* B Isoleucyl–tRNA Synthetase," *Biochem J.*, 191:209–219 (1980).

Weygand–Durašević, I., et al., "Yeast Seryl–tRNA Synthetase Expressed in *Escherichia coli* Recognizes Bacterial Serine–Specific tRNAs in vivo," *Eur. J. Biochem.* 214:869–877 (1993).

Shepard, A., et al., "RNA Binding Determinant in Some Class I tRNA Synthetases Identified by Alignment–Guided Mutagenesis," *Proc. Natl. Acad. Sci. USA*, 89:9964–9968 (1992).

Shiba, K. and Shimmel, P., "Functional Assembly of a Randomly Cleaved Protein," *Proc. Natl. Acad. Sci. USA*, 89:1880–1884 (1992).

Iaccarino, M. and Berg, P., "Isoleucine Auxotrophy as a Consequence of a Mutationally Altered Isoleucyl–Transfer Ribonucleic Acid Synthetase," *J. Bacteriol.*, 105:527–537 (1970).

Hou, Y–M., et al., "Sequence Determination and Modeling of Structural Motifs for the Smallest Monomeric Aminoacyl–tRNA Synthetase," *Proc. Natl. Acad. Sci.*, 88:976–980 (1991).

Heck, J. D. and Hatfield, G. W., "Valyl–tRNA Synthetase Gene of *Escherichia coli* K12: Primary Structure and Homology Within a Family of Aminoacyl–tRNA Synthetases," *The Journal of Biological Chemistry* 263(2):868–877 (1988).

Lazard, M., et al., "Purification and Characterization of the Isoleucyl–tRNA Synthetase Component from the High Molecular Weight Complex of Sheep Liver: A Hydrophobic Metalloprotein," *Biochemistry*, 24:5099–5106 (1985).

Naparstek, Y. and Plotz, P. H., "The Role of Autoantibodies in Autoimmune Disease," *Annu. Rev. Immunol.*, 11:79–104 (1993).

Dang, C. V. and Dang, C. V., "Multienzyme Complex of Aminoacyl–tRNA Synthetases: An Essence of Being Eukaryotic." *Biochem. J.*, 239:249–255 (1986).

Mathews, M. B. and Bernstein, R. M., "Myositis Autoantibody Inhibits Histidyl–tRNA Synthetase: A Model for Autoimmunity," *Nature*, 304:177–179 (1983).

Gelpi, C., et al., "Autoantibodies to a Transfer RNA–Associated Protein in a Murine Model of Chronic Graft Versus Host Disease," *Journal of Immunology*, 1989–1999 (1994).

SEQUENCE LISTING ( 1 ) GENERAL INFORMATION:

( i i i ) NUMBER OF SEQUENCES: 26

( 2 ) INFORMATION FOR SEQ ID NO:1:

( i ) SEQUENCE CHARACTERISTICS:
        ( A ) LENGTH: 3387 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 3..2981

( x i ) SEQUENCE DESCRIPTION: SEQ ID NO:1:

```
GA  AGT TTG TGG GGG ACG CCC CGC CTT CCC TGC AGC CCG GGA TGG CAA         47
    Ser Leu Trp Gly Thr Pro Arg Leu Pro Cys Ser Pro Gly Trp Gln
    1               5                   10                  15

GGG GCG ACG AAG AGG CTT CTG GTG CGG TCG GTC TCC GGG GCC AGT AAC         95
Gly Ala Thr Lys Arg Leu Leu Val Arg Ser Val Ser Gly Ala Ser Asn
            20                  25                  30

CAC CAG CCG AAC TCG AAT AGT GGC AGA TAC CGG GAC ACG GTG CTG CTG        143
His Gln Pro Asn Ser Asn Ser Gly Arg Tyr Arg Asp Thr Val Leu Leu
                35                  40                  45

CCG CAG ACG AGC TTC CCC ATG AAG CTG CTG GGC CGC CAG CAG CCG GAC        191
Pro Gln Thr Ser Phe Pro Met Lys Leu Leu Gly Arg Gln Gln Pro Asp
            50                  55                  60

ACG GAG CTG GAG ATC CAG CAG AAA TGT GGA TTT TCA GAA CTT TAT TCA        239
Thr Glu Leu Glu Ile Gln Gln Lys Cys Gly Phe Ser Glu Leu Tyr Ser
65                  70                  75

TGG CAA AGA GAA AGA AAA GTA AAG ACA GAA TTT TGC CTT CAT GAT GGA        287
Trp Gln Arg Glu Arg Lys Val Lys Thr Glu Phe Cys Leu His Asp Gly
80                  85                  90                  95

CCT CCT TAT GCA AAC GGT GAC CCT CAT GTT GGA CAT GCT TTA AAT AAG        335
Pro Pro Tyr Ala Asn Gly Asp Pro His Val Gly His Ala Leu Asn Lys
            100                 105                 110

ATT TTG AAA GAC ATA GCC AAT CGA TTC CAT ATG ATG AAT GGC TCC AAA        383
Ile Leu Lys Asp Ile Ala Asn Arg Phe His Met Met Asn Gly Ser Lys
                115                 120                 125

ATA CAT TTT GTG CCC GGC TGG GAT TGT CAT GGG TTG CCC ATT GAA ATA        431
Ile His Phe Val Pro Gly Trp Asp Cys His Gly Leu Pro Ile Glu Ile
            130                 135                 140

AAA GTA TTA TCA GAA CTT GGT AGA GAA GCT CAG AAT CTT TCA GCT ATG        479
Lys Val Leu Ser Glu Leu Gly Arg Glu Ala Gln Asn Leu Ser Ala Met
145                 150                 155

GAA ATT AGA AAG AAA GCT AGA TCA TTT GCT AAA GCA GCC ATT GAG AAA        527
Glu Ile Arg Lys Lys Ala Arg Ser Phe Ala Lys Ala Ala Ile Glu Lys
160                 165                 170                 175

CAG AAA TCA GCA TTT ATT CGT TGG GGA ATA ATG GCA GAT TGG AAT AAT        575
Gln Lys Ser Ala Phe Ile Arg Trp Gly Ile Met Ala Asp Trp Asn Asn
            180                 185                 190

TGC TAC TAT ACA TTT GAT GGG AAG TAT GAA GCC AAA CAG TTG AGA ACT        623
Cys Tyr Tyr Thr Phe Asp Gly Lys Tyr Glu Ala Lys Gln Leu Arg Thr
                195                 200                 205

TTT TAC CAA ATG TAT GAT AAG GGC TTG GTT TAT CGA TCT TAC AAA CCT        671
Phe Tyr Gln Met Tyr Asp Lys Gly Leu Val Tyr Arg Ser Tyr Lys Pro
            210                 215                 220

GTG TTT TGG TCT CCG TCA TCT AGG ACT GCA TTG GCT GAA GCA GAA CTT        719
Val Phe Trp Ser Pro Ser Ser Arg Thr Ala Leu Ala Glu Ala Glu Leu
225                 230                 235

GAA TAT AAT CCT GAG CAT GTC AGT CGT TCA ATA TAT GTA AAA TTT CCT        767
Glu Tyr Asn Pro Glu His Val Ser Arg Ser Ile Tyr Val Lys Phe Pro
240                 245                 250                 255

CTC TTA AAG CCT TCT CCA AAA TTG GCA TCT CTT ATA GAT GGT TCA TCT        815
Leu Leu Lys Pro Ser Pro Lys Leu Ala Ser Leu Ile Asp Gly Ser Ser
            260                 265                 270

CCT GTT AGT ATT TTG GTC TGG ACC ACA CAA CCT TGG ACG ATT CCA GCC        863
Pro Val Ser Ile Leu Val Trp Thr Thr Gln Pro Trp Thr Ile Pro Ala
                275                 280                 285

AAT GAA GCT GTT TGC TAT ATG CCT GAA TCA AAG TAT GCT GTT GTG AAA        911
Asn Glu Ala Val Cys Tyr Met Pro Glu Ser Lys Tyr Ala Val Val Lys
            290                 295                 300

TGT TCT AAG TCT GGA GAC CTC TAC GTA CTG GCG GCA GAT AAA GTA GCA        959
Cys Ser Lys Ser Gly Asp Leu Tyr Val Leu Ala Ala Asp Lys Val Ala
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     |     |     | 305 |     |     |     | 310 |     |     |     | 315 |     |     |     |      |
| TCT | GTT | GCT | TCT | ACT | TTG | GAA | ACA | ACA | TTT | GAG | ACT | ATT | TCA | ACA | CTT | 1007 |
| Ser | Val | Ala | Ser | Thr | Leu | Glu | Thr | Thr | Phe | Glu | Thr | Ile | Ser | Thr | Leu |      |
| 320 |     |     |     |     | 325 |     |     |     |     | 330 |     |     |     |     | 335 |      |
| TCA | GGT | GTA | GAT | TTG | GAA | AAT | GGT | ACT | TGC | AGT | CAT | CCA | TTA | ATT | CCT | 1055 |
| Ser | Gly | Val | Asp | Leu | Glu | Asn | Gly | Thr | Cys | Ser | His | Pro | Leu | Ile | Pro |      |
|     |     |     |     | 340 |     |     |     |     | 345 |     |     |     |     | 350 |     |      |
| GAT | AAA | GCC | TCT | CCT | CTT | TTA | CCT | GCA | AAT | CAT | GTG | ACC | ATG | GCA | AAA | 1103 |
| Asp | Lys | Ala | Ser | Pro | Leu | Leu | Pro | Ala | Asn | His | Val | Thr | Met | Ala | Lys |      |
|     |     |     | 355 |     |     |     |     | 360 |     |     |     |     | 365 |     |     |      |
| GGA | ACG | GGA | TTG | GTT | CAC | ACA | GCC | CCA | GCT | CAT | GGT | ATG | GAA | GAC | TAC | 1151 |
| Gly | Thr | Gly | Leu | Val | His | Thr | Ala | Pro | Ala | His | Gly | Met | Glu | Asp | Tyr |      |
|     |     | 370 |     |     |     |     | 375 |     |     |     |     | 380 |     |     |     |      |
| GGT | GTA | GCG | TCT | CAG | CAC | AAC | CTG | CCC | ATG | GAT | TGT | CTA | GTG | GAC | GAA | 1199 |
| Gly | Val | Ala | Ser | Gln | His | Asn | Leu | Pro | Met | Asp | Cys | Leu | Val | Asp | Glu |      |
|     | 385 |     |     |     |     | 390 |     |     |     |     | 395 |     |     |     |     |      |
| GAT | GGA | GTT | TTC | ACA | GAT | GTT | GCA | GGT | CCT | GAA | CTT | CAA | AAC | AAG | GCT | 1247 |
| Asp | Gly | Val | Phe | Thr | Asp | Val | Ala | Gly | Pro | Glu | Leu | Gln | Asn | Lys | Ala |      |
| 400 |     |     |     |     | 405 |     |     |     |     | 410 |     |     |     |     | 415 |      |
| GTC | CTT | GAA | GAG | GGA | ACT | GAT | GTG | GTT | ATA | AAG | ATG | CTT | CAG | ACT | GCA | 1295 |
| Val | Leu | Glu | Glu | Gly | Thr | Asp | Val | Val | Ile | Lys | Met | Leu | Gln | Thr | Ala |      |
|     |     |     |     | 420 |     |     |     |     | 425 |     |     |     |     | 430 |     |      |
| AAG | AAT | TTG | TTG | AAA | GAG | GAG | AAA | TTG | GTG | CAT | AGC | TAT | CCG | TAT | GAC | 1343 |
| Lys | Asn | Leu | Leu | Lys | Glu | Glu | Lys | Leu | Val | His | Ser | Tyr | Pro | Tyr | Asp |      |
|     |     |     | 435 |     |     |     |     | 440 |     |     |     |     | 445 |     |     |      |
| TGG | AGG | ACC | AAG | AAA | CCT | GTG | GTT | ATT | CGT | GCC | AGC | AAG | CAG | TGG | TTT | 1391 |
| Trp | Arg | Thr | Lys | Lys | Pro | Val | Val | Ile | Arg | Ala | Ser | Lys | Gln | Trp | Phe |      |
|     |     | 450 |     |     |     |     | 455 |     |     |     |     | 460 |     |     |     |      |
| ATA | AAC | ATC | ACG | GAT | ATT | AAG | ACT | GCA | GCC | AAG | GAA | TTG | TTA | AAA | AAG | 1439 |
| Ile | Asn | Ile | Thr | Asp | Ile | Lys | Thr | Ala | Ala | Lys | Glu | Leu | Leu | Lys | Lys |      |
|     | 465 |     |     |     |     | 470 |     |     |     |     | 475 |     |     |     |     |      |
| GTG | AAA | TTT | ATT | CCT | GGA | TCA | GCA | CTG | AAT | GGC | ATG | GTT | GAA | ATG | ATG | 1487 |
| Val | Lys | Phe | Ile | Pro | Gly | Ser | Ala | Leu | Asn | Gly | Met | Val | Glu | Met | Met |      |
| 480 |     |     |     |     | 485 |     |     |     |     | 490 |     |     |     |     | 495 |      |
| GAC | AGG | CGG | CCA | TAT | TGG | TGT | ATA | TCA | AGG | CAA | AGA | GTT | TGG | GGT | GTT | 1535 |
| Asp | Arg | Arg | Pro | Tyr | Trp | Cys | Ile | Ser | Arg | Gln | Arg | Val | Trp | Gly | Val |      |
|     |     |     |     | 500 |     |     |     |     | 505 |     |     |     |     | 510 |     |      |
| CCA | ATT | CCT | GTG | TTT | CAT | CAT | AAG | ACC | AAG | GAT | GAA | TAC | TTG | ATC | AAC | 1583 |
| Pro | Ile | Pro | Val | Phe | His | His | Lys | Thr | Lys | Asp | Glu | Tyr | Leu | Ile | Asn |      |
|     |     |     | 515 |     |     |     |     | 520 |     |     |     |     | 525 |     |     |      |
| AGC | CAA | ACC | ACT | GAG | CAT | ATT | GTT | AAA | CTA | GTG | GAA | CAA | CAC | GGC | AGT | 1631 |
| Ser | Gln | Thr | Thr | Glu | His | Ile | Val | Lys | Leu | Val | Glu | Gln | His | Gly | Ser |      |
|     |     | 530 |     |     |     |     | 535 |     |     |     |     | 540 |     |     |     |      |
| GAT | ATC | TGG | TGG | ACT | CTT | CCC | CCT | GAA | CAA | CTT | CTT | CCA | AAA | GAA | GTC | 1679 |
| Asp | Ile | Trp | Trp | Thr | Leu | Pro | Pro | Glu | Gln | Leu | Leu | Pro | Lys | Glu | Val |      |
|     | 545 |     |     |     |     | 550 |     |     |     |     | 555 |     |     |     |     |      |
| TTA | TCT | GAG | GTT | GGT | GGC | CCT | GAT | GCC | TTG | GAA | TAT | GTG | CCA | GGT | CAG | 1727 |
| Leu | Ser | Glu | Val | Gly | Gly | Pro | Asp | Ala | Leu | Glu | Tyr | Val | Pro | Gly | Gln |      |
| 560 |     |     |     |     | 565 |     |     |     |     | 570 |     |     |     |     | 575 |      |
| GAT | ATT | TTG | GAC | ATC | TGG | TTT | GAT | AGC | GGA | ACT | TCA | TGG | TCT | TAT | GTT | 1775 |
| Asp | Ile | Leu | Asp | Ile | Trp | Phe | Asp | Ser | Gly | Thr | Ser | Trp | Ser | Tyr | Val |      |
|     |     |     |     | 580 |     |     |     |     | 585 |     |     |     |     | 590 |     |      |
| CTT | CCA | GGT | CCT | GAC | CAA | AGA | GCA | GAT | TTG | TAT | TTG | GAA | GGA | AAA | GAC | 1823 |
| Leu | Pro | Gly | Pro | Asp | Gln | Arg | Ala | Asp | Leu | Tyr | Leu | Glu | Gly | Lys | Asp |      |
|     |     |     | 595 |     |     |     |     | 600 |     |     |     |     | 605 |     |     |      |
| CAG | CTC | GGG | GGT | TGG | TTT | CAG | TCA | TCC | TTA | TTA | ACA | AGT | GTG | GCA | GCA | 1871 |
| Gln | Leu | Gly | Gly | Trp | Phe | Gln | Ser | Ser | Leu | Leu | Thr | Ser | Val | Ala | Ala |      |
|     |     | 610 |     |     |     |     | 615 |     |     |     |     | 620 |     |     |     |      |
| AGG | AAG | AGA | GCA | CCT | TAT | AAG | ACA | GTG | ATT | GTT | CAT | GGA | TTT | ACC | CTT | 1919 |
| Arg | Lys | Arg | Ala | Pro | Tyr | Lys | Thr | Val | Ile | Val | His | Gly | Phe | Thr | Leu |      |

| | | | | | | | | | | | | | | | | |
|---|---|---|---|---|---|---|---|---|---|---|---|---|---|---|---|---|
| | | 625 | | | | | 630 | | | | | 635 | | | | |
| GGA Gly 640 | GAA Glu | AAG Lys | GGA Gly | GAA Glu | AAG Lys 645 | ATG Met | TCC Ser | AAG Lys | TCT Ser | CTT Leu 650 | GGG Gly | AAT Asn | GTC Val | ATT Ile | CAT His 655 | 1967 |
| CCT Pro | GAT Asp | GTT Val | GTC Val | GTT Val 660 | AAT Asn | GGA Gly | GGA Gly | CAA Gln | GAT Asp 665 | CAA Gln | AGC Ser | AAA Lys | GAG Glu | CCT Pro 670 | CCG Pro | 2015 |
| TAT Tyr | GGT Gly | GCT Ala | GAT Asp 675 | GTC Val | CTT Leu | CGC Arg | TGG Trp | TGG Trp 680 | GTA Val | GCT Ala | GAT Asp | TCC Ser | AAT Asn 685 | GTC Val | TTC Phe | 2063 |
| ACC Thr | GAA Glu | GTT Val 690 | GCA Ala | ATT Ile | GGC Gly | CCA Pro | TCC Ser 695 | GTG Val | CTC Leu | AAT Asn | GCT Ala | GCC Ala 700 | AGA Arg | GAT Asp | GAT Asp | 2111 |
| ATT Ile | AGC Ser 705 | AAG Lys | CTT Leu | AGG Arg | AAT Asn | ACA Thr 710 | CTT Leu | CGC Arg | TTT Phe | CTT Leu | TTG Leu 715 | GGA Gly | AAT Asn | GTG Val | GCT Ala | 2159 |
| GAT Asp 720 | TTC Phe | AAC Asn | CCA Pro | GAA Glu | ACA Thr 725 | GAT Asp | TCC Ser | ATC Ile | CCT Pro | GTA Val 730 | AAC Asn | GAT Asp | ATG Met | TAT Tyr | GTC Val 735 | 2207 |
| ATA Ile | GAC Asp | CAG Gln | TAC Tyr | ATG Met 740 | CTA Leu | CAC His | TTA Leu | CTG Leu | CAG Gln 745 | GAT Asp | TTG Leu | GCA Ala | AAC Asn | AAG Lys 750 | ATT Ile | 2255 |
| ACC Thr | GAA Glu | TTA Leu | TAC Tyr 755 | AAA Lys | CAA Gln | TAT Tyr | GAT Asp | TTT Phe 760 | GGA Gly | AAA Lys | GTT Val | GTT Val | CGG Arg 765 | CTG Leu | TTA Leu | 2303 |
| CGG Arg | ACG Thr | TTT Phe 770 | TAT Tyr | ACC Thr | AGA Arg | GAG Glu | CTC Leu 775 | TCT Ser | AAC Asn | TTT Phe | TAT Tyr | TTC Phe 780 | AGT Ser | ATA Ile | ATC Ile | 2351 |
| AAA Lys | GAT Asp 785 | AGG Arg | CTC Leu | TAT Tyr | TGT Cys | GAA Glu 790 | AAG Lys | GAA Glu | AAT Asn | GAC Asp | CCC Pro 795 | AAA Lys | CGA Arg | CGC Arg | TCT Ser | 2399 |
| TGT Cys 800 | CAG Gln | ACT Thr | GCA Ala | TTA Leu | GTT Val 805 | GAA Glu | ATT Ile | TTG Leu | GAT Asp | GTA Val 810 | ATA Ile | GTT Val | CGT Arg | TCT Ser | TTT Phe 815 | 2447 |
| GCT Ala | CCC Pro | ATT Ile | CTT Leu | CCT Pro 820 | CAC His | CTG Leu | GCT Ala | GAA Glu | GAG Glu 825 | GTG Val | TTC Phe | CAG Gln | CAC His | ATA Ile 830 | CCT Pro | 2495 |
| TAT Tyr | ATT Ile | AAA Lys | GAG Glu 835 | CCC Pro | AAG Lys | AGT Ser | GTT Val | TTC Phe 840 | CGT Arg | ACT Thr | GGG Gly | TGG Trp | ATT Ile 845 | AGT Ser | ACT Thr | 2543 |
| AGT Ser | TCT Ser | ATC Ile 850 | TGG Trp | AAA Lys | AAG Lys | CCC Pro | GGG Gly 855 | TTG Leu | GAA Glu | GAA Glu | GCT Ala | GTG Val 860 | GAG Glu | AGT Ser | GCG Ala | 2591 |
| TGT Cys | GCA Ala 865 | ATG Met | CGA Arg | GAC Asp | TCA Ser | TTT Phe 870 | CTT Leu | GGA Gly | AGC Ser | ATC Ile | CCT Pro 875 | GGC Gly | AAA Lys | AAT Asn | GCA Ala | 2639 |
| GCT Ala 880 | GAG Glu | TAC Tyr | AAG Lys | GTT Val | ATC Ile 885 | ACT Thr | GTG Val | ATA Ile | GAA Glu | CCT Pro 890 | GGA Gly | CTG Leu | CTT Leu | TTT Phe | GAG Glu 895 | 2687 |
| ATA Ile | ATA Ile | GAG Glu | ATG Met | CTG Leu 900 | CAG Gln | TCT Ser | GAA Glu | GAG Glu | ACT Thr 905 | TCC Ser | AGC Ser | ACC Thr | TCT Ser | CAG Gln 910 | TTG Leu | 2735 |
| AAT Asn | GAA Glu | TTA Leu | ATG Met | ATG Met 915 | GCT Ala | TCT Ser | GAG Glu | TCA Ser | ACT Thr 920 | TTA Leu | CTG Leu | GCT Ala | CAG Gln | GAA Glu 925 | CCA Pro | 2783 |
| CGA Arg | GAG Glu | ATG Met 930 | ACT Thr | GCA Ala | GAT Asp | GTA Val | ATC Ile 935 | GAG Glu | CTT Leu | AAA Lys | GGG Gly | AAA Lys 940 | TTC Phe | CTC Leu | ATC Ile | 2831 |
| AAC Asn | TTA Leu | GAA Glu | GGT Gly | GGT Gly | GAT Asp | ATT Ile | CGT Arg | GAA Glu | GAG Glu | TCT Ser | TCC Ser | TAT Tyr | AAA Lys | GTA Val | ATT Ile | 2879 |

|     |     |     |     | 945 |     |     |     | 950 |     |     |     | 955 |     |     |     |      |
| --- | --- | --- | --- | --- | --- | --- | --- | --- | --- | --- | --- | --- | --- | --- | --- | ---- |
| GTC | ATG | CCG | ACT | ACG | AAA | GAA | AAA | TGC | CCC | CGT | TGT | TGG | AAG | TAT | ACA | 2927 |
| Val | Met | Pro | Thr | Thr | Lys | Glu | Lys | Cys | Pro | Arg | Cys | Trp | Lys | Tyr | Thr |      |
| 960 |     |     |     |     | 965 |     |     |     |     | 970 |     |     |     |     | 975 |      |

| GCG | GAG | TCT | TCA | GAT | ACA | CTG | TGT | CCT | CGA | TGT | GCA | GAA | GTT | GTC | AGT | 2975 |
| --- | --- | --- | --- | --- | --- | --- | --- | --- | --- | --- | --- | --- | --- | --- | --- | ---- |
| Ala | Glu | Ser | Ser | Asp | Thr | Leu | Cys | Pro | Arg | Cys | Ala | Glu | Val | Val | Ser |      |
|     |     |     |     | 980 |     |     |     |     | 985 |     |     |     |     | 990 |     |      |

| GGA | AAA | TAGTATTAAC | AGCTCACTCG | AGCAAGAACC | CTCCTGACAG | TACTGGCTGG | 3031 |
| --- | --- | ---------- | ---------- | ---------- | ---------- | ---------- | ---- |
| Gly | Lys |            |            |            |            |            |      |

| AAGTTTGGAT | GGATTATTTA | CAATATAGGA | AAGAAAGCCA | AGATTTAGGT | AATGAGTGGA | 3091 |
| TGAGTAAATG | GTGGAGGATG | GGAGTCAAAA | TCAGAATTAT | AGAAGAAGTA | TTTCCTGTAA | 3151 |
| CTATAGAAAG | AATTATGTAT | ATATACATGC | AGAAATATAT | ATGTGTGTGT | GTATCTGTGG | 3211 |
| ATGGATATAT | GTATATCTCT | TCCTATATAT | ATCCATAGTG | GACTTATTCA | GAACATAGAT | 3271 |
| ATGTATTCAG | CTTGTCTTCA | AATACGGCCA | AGCAGAAAAT | GTTTATATT  | TTATAAATCA | 3331 |
| TCTTTTGACT | CTGTATTTAA | ATTCTATGAT | ACTGAAAATA | AAGGCATTCT | GGAAAA     | 3387 |

( 2 ) INFORMATION FOR SEQ ID NO:2:

( i ) SEQUENCE CHARACTERISTICS:
        ( A ) LENGTH: 993 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| Ser | Leu | Trp | Gly | Thr | Pro | Arg | Leu | Pro | Cys | Ser | Pro | Gly | Trp | Gln | Gly |
| --- | --- | --- | --- | --- | --- | --- | --- | --- | --- | --- | --- | --- | --- | --- | --- |
| 1   |     |     |     | 5   |     |     |     |     | 10  |     |     |     |     | 15  |     |
| Ala | Thr | Lys | Arg | Leu | Leu | Val | Arg | Ser | Val | Ser | Gly | Ala | Ser | Asn | His |
|     |     |     | 20  |     |     |     |     | 25  |     |     |     |     | 30  |     |     |
| Gln | Pro | Asn | Ser | Asn | Ser | Gly | Arg | Tyr | Arg | Asp | Thr | Val | Leu | Leu | Pro |
|     |     |     | 35  |     |     |     | 40  |     |     |     |     | 45  |     |     |     |
| Gln | Thr | Ser | Phe | Pro | Met | Lys | Leu | Leu | Gly | Arg | Gln | Gln | Pro | Asp | Thr |
|     | 50  |     |     |     |     | 55  |     |     |     |     | 60  |     |     |     |     |
| Glu | Leu | Glu | Ile | Gln | Gln | Lys | Cys | Gly | Phe | Ser | Glu | Leu | Tyr | Ser | Trp |
| 65  |     |     |     |     | 70  |     |     |     |     | 75  |     |     |     |     | 80  |
| Gln | Arg | Glu | Arg | Lys | Val | Lys | Thr | Glu | Phe | Cys | Leu | His | Asp | Gly | Pro |
|     |     |     |     | 85  |     |     |     |     | 90  |     |     |     |     | 95  |     |
| Pro | Tyr | Ala | Asn | Gly | Asp | Pro | His | Val | Gly | His | Ala | Leu | Asn | Lys | Ile |
|     |     |     |     | 100 |     |     |     | 105 |     |     |     |     | 110 |     |     |
| Leu | Lys | Asp | Ile | Ala | Asn | Arg | Phe | His | Met | Met | Asn | Gly | Ser | Lys | Ile |
|     |     |     | 115 |     |     |     |     | 120 |     |     |     |     | 125 |     |     |
| His | Phe | Val | Pro | Gly | Trp | Asp | Cys | His | Gly | Leu | Pro | Ile | Glu | Ile | Lys |
|     | 130 |     |     |     |     | 135 |     |     |     |     | 140 |     |     |     |     |
| Val | Leu | Ser | Glu | Leu | Gly | Arg | Glu | Ala | Gln | Asn | Leu | Ser | Ala | Met | Glu |
| 145 |     |     |     |     | 150 |     |     |     |     | 155 |     |     |     |     | 160 |
| Ile | Arg | Lys | Lys | Ala | Arg | Ser | Phe | Ala | Lys | Ala | Ala | Ile | Glu | Lys | Gln |
|     |     |     |     | 165 |     |     |     |     | 170 |     |     |     |     | 175 |     |
| Lys | Ser | Ala | Phe | Ile | Arg | Trp | Gly | Ile | Met | Ala | Asp | Trp | Asn | Asn | Cys |
|     |     |     | 180 |     |     |     |     | 185 |     |     |     |     | 190 |     |     |
| Tyr | Tyr | Thr | Phe | Asp | Gly | Lys | Tyr | Glu | Ala | Lys | Gln | Leu | Arg | Thr | Phe |
|     |     | 195 |     |     |     |     | 200 |     |     |     |     | 205 |     |     |     |
| Tyr | Gln | Met | Tyr | Asp | Lys | Gly | Leu | Val | Tyr | Arg | Ser | Tyr | Lys | Pro | Val |
|     | 210 |     |     |     |     | 215 |     |     |     |     | 220 |     |     |     |     |
| Phe | Trp | Ser | Pro | Ser | Ser | Arg | Thr | Ala | Leu | Ala | Glu | Ala | Glu | Leu | Glu |

|     225                    |                    230                    |                    235                    |                    240 |
|---|---|---|---|

Tyr Asn Pro Glu His Val Ser Arg Ser Ile Tyr Val Lys Phe Pro Leu
                245                 250                 255

Leu Lys Pro Ser Pro Lys Leu Ala Ser Leu Ile Asp Gly Ser Ser Pro
                260                 265                 270

Val Ser Ile Leu Val Trp Thr Thr Gln Pro Trp Thr Ile Pro Ala Asn
            275                 280                 285

Glu Ala Val Cys Tyr Met Pro Glu Ser Lys Tyr Ala Val Val Lys Cys
        290                 295                 300

Ser Lys Ser Gly Asp Leu Tyr Val Leu Ala Ala Asp Lys Val Ala Ser
305                 310                 315                 320

Val Ala Ser Thr Leu Glu Thr Thr Phe Glu Thr Ile Ser Thr Leu Ser
                325                 330                 335

Gly Val Asp Leu Glu Asn Gly Thr Cys Ser His Pro Leu Ile Pro Asp
                340                 345                 350

Lys Ala Ser Pro Leu Leu Pro Ala Asn His Val Thr Met Ala Lys Gly
                355                 360                 365

Thr Gly Leu Val His Thr Ala Pro Ala His Gly Met Glu Asp Tyr Gly
        370                 375                 380

Val Ala Ser Gln His Asn Leu Pro Met Asp Cys Leu Val Asp Glu Asp
385                 390                 395                 400

Gly Val Phe Thr Asp Val Ala Gly Pro Glu Leu Gln Asn Lys Ala Val
                405                 410                 415

Leu Glu Glu Gly Thr Asp Val Val Ile Lys Met Leu Gln Thr Ala Lys
                420                 425                 430

Asn Leu Leu Lys Glu Glu Lys Leu Val His Ser Tyr Pro Tyr Asp Trp
                435                 440                 445

Arg Thr Lys Lys Pro Val Val Ile Arg Ala Ser Lys Gln Trp Phe Ile
        450                 455                 460

Asn Ile Thr Asp Ile Lys Thr Ala Ala Lys Glu Leu Leu Lys Lys Val
465                 470                 475                 480

Lys Phe Ile Pro Gly Ser Ala Leu Asn Gly Met Val Glu Met Met Asp
                485                 490                 495

Arg Arg Pro Tyr Trp Cys Ile Ser Arg Gln Arg Val Trp Gly Val Pro
            500                 505                 510

Ile Pro Val Phe His His Lys Thr Lys Asp Glu Tyr Leu Ile Asn Ser
        515                 520                 525

Gln Thr Thr Glu His Ile Val Lys Leu Val Glu Gln His Gly Ser Asp
        530                 535                 540

Ile Trp Trp Thr Leu Pro Pro Glu Gln Leu Leu Pro Lys Glu Val Leu
545                 550                 555                 560

Ser Glu Val Gly Gly Pro Asp Ala Leu Glu Tyr Val Pro Gly Gln Asp
                565                 570                 575

Ile Leu Asp Ile Trp Phe Asp Ser Gly Thr Ser Trp Ser Tyr Val Leu
            580                 585                 590

Pro Gly Pro Asp Gln Arg Ala Asp Leu Tyr Leu Glu Gly Lys Asp Gln
        595                 600                 605

Leu Gly Gly Trp Phe Gln Ser Ser Leu Leu Thr Ser Val Ala Ala Arg
        610                 615                 620

Lys Arg Ala Pro Tyr Lys Thr Val Ile Val His Gly Phe Thr Leu Gly
625                 630                 635                 640

Glu Lys Gly Glu Lys Met Ser Lys Ser Leu Gly Asn Val Ile His Pro
                645                 650                 655

| | | | | | | | | | | | | | | |
|---|---|---|---|---|---|---|---|---|---|---|---|---|---|---|
| Asp | Val | Val | Val 660 | Asn | Gly | Gly | Gln 665 | Gln | Ser | Lys | Glu | Pro 670 | Pro | Tyr |
| Gly | Ala | Asp 675 | Val | Leu | Arg | Trp 680 | Trp | Val | Ala | Asp | Ser | Asn 685 | Val | Phe | Thr |
| Glu | Val 690 | Ala | Ile | Gly | Pro | Ser 695 | Val | Leu | Asn | Ala | Ala 700 | Arg | Asp | Asp | Ile |
| Ser 705 | Lys | Leu | Arg | Asn | Thr 710 | Leu | Arg | Phe | Leu | Leu 715 | Gly | Asn | Val | Ala | Asp 720 |
| Phe | Asn | Pro | Glu | Thr 725 | Asp | Ser | Ile | Pro | Val 730 | Asn | Asp | Met | Tyr | Val 735 | Ile |
| Asp | Gln | Tyr | Met 740 | Leu | His | Leu | Leu | Gln 745 | Asp | Leu | Ala | Asn | Lys 750 | Ile | Thr |
| Glu | Leu | Tyr 755 | Lys | Gln | Tyr | Asp | Phe 760 | Gly | Lys | Val | Val | Arg 765 | Leu | Leu | Arg |
| Thr | Phe 770 | Tyr | Thr | Arg | Glu | Leu 775 | Ser | Asn | Phe | Tyr | Phe 780 | Ser | Ile | Ile | Lys |
| Asp 785 | Arg | Leu | Tyr | Cys | Glu 790 | Lys | Glu | Asn | Asp | Pro 795 | Lys | Arg | Arg | Ser | Cys 800 |
| Gln | Thr | Ala | Leu | Val 805 | Glu | Ile | Leu | Asp | Val 810 | Ile | Val | Arg | Ser | Phe 815 | Ala |
| Pro | Ile | Leu | Pro 820 | His | Leu | Ala | Glu | Glu 825 | Val | Phe | Gln | His | Ile 830 | Pro | Tyr |
| Ile | Lys | Glu 835 | Pro | Lys | Ser | Val | Phe 840 | Arg | Thr | Gly | Trp | Ile 845 | Ser | Thr | Ser |
| Ser | Ile 850 | Trp | Lys | Lys | Pro | Gly 855 | Leu | Glu | Glu | Ala | Val 860 | Glu | Ser | Ala | Cys |
| Ala 865 | Met | Arg | Asp | Ser | Phe 870 | Leu | Gly | Ser | Ile | Pro 875 | Gly | Lys | Asn | Ala | Ala 880 |
| Glu | Tyr | Lys | Val | Ile 885 | Thr | Val | Ile | Glu | Pro 890 | Gly | Leu | Leu | Phe | Glu 895 | Ile |
| Ile | Glu | Met | Leu 900 | Gln | Ser | Glu | Glu | Thr 905 | Ser | Ser | Thr | Ser | Gln 910 | Leu | Asn |
| Glu | Leu | Met 915 | Met | Ala | Ser | Glu | Ser 920 | Thr | Leu | Leu | Ala | Gln 925 | Glu | Pro | Arg |
| Glu | Met 930 | Thr | Ala | Asp | Val | Ile 935 | Glu | Leu | Lys | Gly | Lys 940 | Phe | Leu | Ile | Asn |
| Leu 945 | Glu | Gly | Gly | Asp | Ile 950 | Arg | Glu | Glu | Ser | Ser 955 | Tyr | Lys | Val | Ile | Val 960 |
| Met | Pro | Thr | Thr | Lys 965 | Glu | Lys | Cys | Pro | Arg 970 | Cys | Trp | Lys | Tyr | Thr 975 | Ala |
| Glu | Ser | Ser | Asp 980 | Thr | Leu | Cys | Pro | Arg 985 | Cys | Ala | Glu | Val | Val 990 | Ser | Gly |
| Lys | | | | | | | | | | | | | | | |

( 2 ) INFORMATION FOR SEQ ID NO:3:

( i ) SEQUENCE CHARACTERISTICS:
        ( A ) LENGTH: 4500 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 230..4027

( x i ) SEQUENCE DESCRIPTION: SEQ ID NO:3:

```
GCCGGATGAG TTGCTTTTAG GCTTGCTGGC CCGCGGGGCT GTCCAGGCAC GCGAGGCCCC        60

TCAGGTACGC CCTCTCTTCC CTGCAGGATC CGGCCCTCAA AGACGAGGGT CACGCACGCG       120

TTACAACCCC GAAACAGTAG CACAAGATTT AATTTTAAA AGAGCGTGTT TCTTCGGGGC        180

TTGCCGTTCG TTCGTTTCCA GCCTCAGGAA TTTATGGTCG CCTTTTTGA ATG AGC           235
                                                      Met Ser
                                                        1
```

| AAC | AAA | ATG | CTT | CAA | CAA | GTT | CCA | GAA | AAC | ATA | AAT | TTT | CCT | GCT | GAA | 283 |
|-----|-----|-----|-----|-----|-----|-----|-----|-----|-----|-----|-----|-----|-----|-----|-----|-----|
| Asn | Lys | Met | Leu | Gln | Gln | Val | Pro | Glu | Asn | Ile | Asn | Phe | Pro | Ala | Glu | |
| | | 5 | | | | | 10 | | | | | 15 | | | | |

| GAA | GAG | AAA | ATC | TTG | GAG | TTT | TGG | ACT | GAA | TTT | AAT | TGT | TTT | CAG | GAA | 331 |
|-----|-----|-----|-----|-----|-----|-----|-----|-----|-----|-----|-----|-----|-----|-----|-----|-----|
| Glu | Glu | Lys | Ile | Leu | Glu | Phe | Trp | Thr | Glu | Phe | Asn | Cys | Phe | Gln | Glu | |
| | 20 | | | | | 25 | | | | | 30 | | | | | |

| TGC | TTA | AAG | CAA | TCA | AAA | CAT | AAA | CCA | AAA | TTT | ACC | TTC | TAT | GAT | GGT | 379 |
|-----|-----|-----|-----|-----|-----|-----|-----|-----|-----|-----|-----|-----|-----|-----|-----|-----|
| Cys | Leu | Lys | Gln | Ser | Lys | His | Lys | Pro | Lys | Phe | Thr | Phe | Tyr | Asp | Gly | |
| 35 | | | | 40 | | | | | 45 | | | | | | 50 | |

| CCT | CCT | TTT | GCA | ACT | GGA | CTG | CCT | CAC | TAT | GGA | CAT | ATA | CTT | GCG | GGT | 427 |
|-----|-----|-----|-----|-----|-----|-----|-----|-----|-----|-----|-----|-----|-----|-----|-----|-----|
| Pro | Pro | Phe | Ala | Thr | Gly | Leu | Pro | His | Tyr | Gly | His | Ile | Leu | Ala | Gly | |
| | | | | 55 | | | | | 60 | | | | | | 65 | |

| ACA | ATT | AAA | GAT | ATA | GTT | ACA | AGA | TAT | GCT | CAC | CAG | AGT | GGG | TTT | CAT | 475 |
|-----|-----|-----|-----|-----|-----|-----|-----|-----|-----|-----|-----|-----|-----|-----|-----|-----|
| Thr | Ile | Lys | Asp | Ile | Val | Thr | Arg | Tyr | Ala | His | Gln | Ser | Gly | Phe | His | |
| | | | 70 | | | | | 75 | | | | | 80 | | | |

| GTT | GAC | AGA | AGA | TTT | GGA | TGG | GAT | TGC | CAT | GGC | TTA | CCT | GTG | GAA | TAT | 523 |
|-----|-----|-----|-----|-----|-----|-----|-----|-----|-----|-----|-----|-----|-----|-----|-----|-----|
| Val | Asp | Arg | Arg | Phe | Gly | Trp | Asp | Cys | His | Gly | Leu | Pro | Val | Glu | Tyr | |
| | | 85 | | | | | 90 | | | | | 95 | | | | |

| GAA | ATT | GAT | AAG | ACA | CTG | GGA | ATC | AGA | GGA | CCA | GAG | GAT | GTG | GCC | AAA | 571 |
|-----|-----|-----|-----|-----|-----|-----|-----|-----|-----|-----|-----|-----|-----|-----|-----|-----|
| Glu | Ile | Asp | Lys | Thr | Leu | Gly | Ile | Arg | Gly | Pro | Glu | Asp | Val | Ala | Lys | |
| 100 | | | | | 105 | | | | | 110 | | | | | | |

| ATG | GGG | ATT | ACA | GAG | TAT | AAC | AAT | CAG | TGC | CGA | GCA | ATT | GTG | ATG | AGA | 619 |
|-----|-----|-----|-----|-----|-----|-----|-----|-----|-----|-----|-----|-----|-----|-----|-----|-----|
| Met | Gly | Ile | Thr | Glu | Tyr | Asn | Asn | Gln | Cys | Arg | Ala | Ile | Val | Met | Arg | |
| 115 | | | | | 120 | | | | | 125 | | | | | 130 | |

| TAT | TCT | GCT | GAG | TGG | AAG | TCT | ACT | GTT | AGC | AGA | CTT | GGC | CGA | TGG | ATT | 667 |
|-----|-----|-----|-----|-----|-----|-----|-----|-----|-----|-----|-----|-----|-----|-----|-----|-----|
| Tyr | Ser | Ala | Glu | Trp | Lys | Ser | Thr | Val | Ser | Arg | Leu | Gly | Arg | Trp | Ile | |
| | | | | 135 | | | | | 140 | | | | | 145 | | |

| GAC | TTT | GAC | AAT | GAC | TAT | AAA | ACT | CTG | TAT | CCA | CAA | TTC | ATG | GAA | TCA | 715 |
|-----|-----|-----|-----|-----|-----|-----|-----|-----|-----|-----|-----|-----|-----|-----|-----|-----|
| Asp | Phe | Asp | Asn | Asp | Tyr | Lys | Thr | Leu | Tyr | Pro | Gln | Phe | Met | Glu | Ser | |
| | | | 150 | | | | | 155 | | | | | 160 | | | |

| GTC | TGG | TGG | GTC | TTC | AAA | CAA | CTC | TAT | GAT | AAA | GGC | CTT | GTT | TAT | AGA | 763 |
|-----|-----|-----|-----|-----|-----|-----|-----|-----|-----|-----|-----|-----|-----|-----|-----|-----|
| Val | Trp | Trp | Val | Phe | Lys | Gln | Leu | Tyr | Asp | Lys | Gly | Leu | Val | Tyr | Arg | |
| | | 165 | | | | | 170 | | | | | 175 | | | | |

| GGT | GTG | AAA | GTC | ATG | CCC | TTC | TCT | ACG | GCA | TGT | AAC | ACT | CCA | CTT | TCC | 811 |
|-----|-----|-----|-----|-----|-----|-----|-----|-----|-----|-----|-----|-----|-----|-----|-----|-----|
| Gly | Val | Lys | Val | Met | Pro | Phe | Ser | Thr | Ala | Cys | Asn | Thr | Pro | Leu | Ser | |
| | 180 | | | | | 185 | | | | | 190 | | | | | |

| AAC | TTC | GAG | TCA | CAC | CAG | AAT | TAT | AAG | GAT | GTT | CAA | GAT | CCT | TCA | GTA | 859 |
|-----|-----|-----|-----|-----|-----|-----|-----|-----|-----|-----|-----|-----|-----|-----|-----|-----|
| Asn | Phe | Glu | Ser | His | Gln | Asn | Tyr | Lys | Asp | Val | Gln | Asp | Pro | Ser | Val | |
| 195 | | | | | 200 | | | | | 205 | | | | | 210 | |

| TTT | GTA | ACT | TTC | CCT | TTG | GAA | GAA | GAT | GAA | ACT | GTA | TCT | TTA | GTT | GCT | 907 |
|-----|-----|-----|-----|-----|-----|-----|-----|-----|-----|-----|-----|-----|-----|-----|-----|-----|
| Phe | Val | Thr | Phe | Pro | Leu | Glu | Glu | Asp | Glu | Thr | Val | Ser | Leu | Val | Ala | |
| | | | | 215 | | | | | 220 | | | | | 225 | | |

| TGG | ACA | ACC | ACT | CCC | TGG | ACT | CTA | CCT | AGT | AAC | CTT | GCT | GTG | TGT | GTT | 955 |
|-----|-----|-----|-----|-----|-----|-----|-----|-----|-----|-----|-----|-----|-----|-----|-----|-----|
| Trp | Thr | Thr | Thr | Pro | Trp | Thr | Leu | Pro | Ser | Asn | Leu | Ala | Val | Cys | Val | |
| | | | 230 | | | | | 235 | | | | | 240 | | | |

| AAT | CCA | GAA | ATG | CAA | TAT | GTG | AAA | ATT | AAA | GAT | GTT | GCC | AGA | GGA | CGA | 1003 |
|-----|-----|-----|-----|-----|-----|-----|-----|-----|-----|-----|-----|-----|-----|-----|-----|------|
| Asn | Pro | Glu | Met | Gln | Tyr | Val | Lys | Ile | Lys | Asp | Val | Ala | Arg | Gly | Arg | |
| | | 245 | | | | | 250 | | | | | 255 | | | | |

| TTA | CTC | ATT | TTA | ATG | GAA | GCC | AGA | TTG | TCA | GCC | CTC | TAT | AAA | TTG | GAG | 1051 |
|-----|-----|-----|-----|-----|-----|-----|-----|-----|-----|-----|-----|-----|-----|-----|-----|------|
| Leu | Leu | Ile | Leu | Met | Glu | Ala | Arg | Leu | Ser | Ala | Leu | Tyr | Lys | Leu | Glu | |
| | 260 | | | | | 265 | | | | | 270 | | | | | |

| | | | | | | | | | | | | | | | | |
|---|---|---|---|---|---|---|---|---|---|---|---|---|---|---|---|---|
| AGT | GAC | TAT | GAG | ATC | CTT | GAA | AGA | TTT | CCT | GGT | GCC | TAT | CTT | AAA | GGC | 1099 |
| Ser 275 | Asp | Tyr | Glu | Ile 280 | Leu | Glu | Arg | Phe | Pro 285 | Gly | Ala | Tyr | Leu | Lys 290 | Gly | |
| AAG | AAG | TAC | AGG | CCC | CTG | TTT | GAC | TAT | TTC | CTG | AAG | TGT | AAA | GAG | AAT | 1147 |
| Lys | Lys | Tyr | Arg | Pro 295 | Leu | Phe | Asp | Tyr | Phe 300 | Leu | Lys | Cys | Lys | Glu 305 | Asn | |
| GGC | GCT | TTC | ACT | GTG | CTT | GTT | GAC | AAC | TAT | GTG | AAG | GAA | GAA | GAA | GGC | 1195 |
| Gly | Ala | Phe | Thr 310 | Val | Leu | Val | Asp | Asn | Tyr 315 | Val | Lys | Glu | Glu | Glu 320 | Gly | |
| ACA | GGG | GTT | GTC | CAC | CAA | GCT | CCT | TAC | TTC | GGT | GCT | GAG | GAC | TAT | CGG | 1243 |
| Thr | Gly | Val 325 | Val | His | Gln | Ala | Pro 330 | Tyr | Phe | Gly | Ala | Glu 335 | Asp | Tyr | Arg | |
| GTC | TGT | ATG | GAC | TTT | AAC | ATT | ATT | CGG | AAA | GAC | TCA | CTC | CCT | GTT | TGC | 1291 |
| Val | Cys 340 | Met | Asp | Phe | Asn | Ile 345 | Ile | Arg | Lys | Asp | Ser 350 | Leu | Pro | Val | Cys | |
| CCT | GTG | GAT | GCT | TCA | GGC | TGC | TTC | ACA | ACG | GAG | GTG | ACA | GAT | TTC | GCA | 1339 |
| Pro 355 | Val | Asp | Ala | Ser | Gly 360 | Cys | Phe | Thr | Thr | Glu 365 | Val | Thr | Asp | Phe | Ala 370 | |
| GGA | CAG | TAT | GTG | AAG | GAT | GCT | GAC | AAA | AGT | ATC | ATC | AGG | ACT | TTG | AAG | 1387 |
| Gly | Gln | Tyr | Val | Lys 375 | Asp | Ala | Asp | Lys | Ser 380 | Ile | Ile | Arg | Thr | Leu 385 | Lys | |
| GAA | CAA | GGC | CGA | CTT | CTG | GTT | GCC | ACC | ACC | TTC | ACT | CAC | AGC | TAC | CCT | 1435 |
| Glu | Gln | Gly | Arg 390 | Leu | Leu | Val | Ala | Thr 395 | Thr | Phe | Thr | His | Ser 400 | Tyr | Pro | |
| TTT | TGC | TGG | AGA | TCA | GAC | ACT | CCT | CTA | ATT | TAC | AAA | GCA | GTG | CCC | AGC | 1483 |
| Phe | Cys | Trp 405 | Arg | Ser | Asp | Thr | Pro 410 | Leu | Ile | Tyr | Lys | Ala 415 | Val | Pro | Ser | |
| TGG | TTT | GTG | CGA | GTG | GAG | AAC | ATG | GTG | GAC | CAG | CTC | CTA | AGG | AAC | AAT | 1531 |
| Trp | Phe 420 | Val | Arg | Val | Glu | Asn 425 | Met | Val | Asp | Gln | Leu 430 | Leu | Arg | Asn | Asn | |
| GAC | CTG | TGC | TAC | TGG | GTC | CCA | GAG | TTG | GTA | CGA | GAA | AAA | CGA | TTT | GGA | 1579 |
| Asp 435 | Leu | Cys | Tyr | Trp | Val 440 | Pro | Glu | Leu | Val | Arg 445 | Glu | Lys | Arg | Phe | Gly 450 | |
| AAT | TGG | CTG | AAA | GAT | GCA | CGT | GAC | TGG | ACA | ATT | TCC | AGA | AAC | AGA | TAC | 1627 |
| Asn | Trp | Leu | Lys | Asp 455 | Ala | Arg | Asp | Trp | Thr 460 | Ile | Ser | Arg | Asn | Arg 465 | Tyr | |
| TGG | GGC | ACC | CCC | ATC | CCA | CTG | TGG | GTC | AGC | GAT | GAC | TTT | GAG | GAG | GTG | 1675 |
| Trp | Gly | Thr | Pro 470 | Ile | Pro | Leu | Trp | Val 475 | Ser | Asp | Asp | Phe | Glu 480 | Glu | Val | |
| GTA | TGC | ATT | GGG | TCA | GTG | GCG | GAA | CTT | GAA | GAA | CTG | TCA | GGA | GCA | AAG | 1723 |
| Val | Cys | Ile 485 | Gly | Ser | Val | Ala | Glu 490 | Leu | Glu | Glu | Leu | Ser 495 | Gly | Ala | Lys | |
| ATC | TCA | GAT | CTC | CAC | AGA | GAG | AGT | GTT | GAC | CAC | CTG | ACC | ATT | CCT | TCA | 1771 |
| Ile | Ser | Asp | Leu | His 500 | Arg | Glu | Ser | Val | Asp 505 | His | Leu | Thr | Ile | Pro 510 | Ser | |
| CGC | TGT | GGG | AAG | GGA | TCC | TTG | CAC | CGC | ATC | TCT | GAA | GTG | TTT | GAC | TGT | 1819 |
| Arg 515 | Cys | Gly | Lys | Gly | Ser 520 | Leu | His | Arg | Ile | Ser 525 | Glu | Val | Phe | Asp | Cys 530 | |
| TGG | TTT | GAG | AGT | GGC | AGC | ATG | CCC | TAT | GCT | CAG | GTT | CAT | TAC | CCG | TTT | 1867 |
| Trp | Phe | Glu | Ser | Gly 535 | Ser | Met | Pro | Tyr | Ala 540 | Gln | Val | His | Tyr | Pro 545 | Phe | |
| GAA | AAC | AAG | AGG | GAG | TTT | GAG | GAT | GCT | TTT | CCT | GCA | GAT | TTC | ATT | GCC | 1915 |
| Glu | Asn | Lys | Arg 550 | Glu | Phe | Glu | Asp | Ala 555 | Phe | Pro | Ala | Asp | Phe 560 | Ile | Ala | |
| GAG | GGC | ATC | GAC | CAA | ACC | AGA | GGA | TGG | TTT | TAT | ACC | CTG | CTG | GTG | CTG | 1963 |
| Glu | Gly | Ile | Asp | Gln 565 | Thr | Arg | Gly | Trp | Phe 570 | Tyr | Thr | Leu | Leu | Val 575 | Leu | |
| GCC | ACG | GCC | CTC | TTT | GGA | CAA | CCG | CCT | TTC | AAG | AAC | GTA | ATT | GTG | AAT | 2011 |
| Ala | Thr 580 | Ala | Leu | Phe | Gly | Gln 585 | Pro | Pro | Phe | Lys | Asn 590 | Val | Ile | Val | Asn | |

```
GGG CTT GTC CTG GCA AGT GAT GGC CAA AAA ATG AGC AAA CGG AAA AAG        2059
Gly Leu Val Leu Ala Ser Asp Gly Gln Lys Met Ser Lys Arg Lys Lys
595                 600                 605                 610

AAT TAT CCA GAT CCA GTT TCC ATC ATC CAG AAG TAT GGT GCT GAT GCC        2107
Asn Tyr Pro Asp Pro Val Ser Ile Ile Gln Lys Tyr Gly Ala Asp Ala
            615                 620                     625

CTC AGA TTA TAT CTG ATT AAC TCC CCT GTG GTG AGA GCA GAA AAC CTC        2155
Leu Arg Leu Tyr Leu Ile Asn Ser Pro Val Val Arg Ala Glu Asn Leu
                630                 635                 640

CGC TTT AAA GAA GAG GGT GTG CGG GAC GTC CTT AAG GAT GTA CTG CTC        2203
Arg Phe Lys Glu Glu Gly Val Arg Asp Val Leu Lys Asp Val Leu Leu
            645                 650                 655

CCA TGG TAC AAT GCC TAT CGC TTC TTA ATC CAG AAC GTT CTG AGG CTC        2251
Pro Trp Tyr Asn Ala Tyr Arg Phe Leu Ile Gln Asn Val Leu Arg Leu
        660                 665                 670

CAG AAG GAG GAA GAA ATA GAA TTT CTC TAC AAT GAG AAC ACG GTT AGA        2299
Gln Lys Glu Glu Glu Ile Glu Phe Leu Tyr Asn Glu Asn Thr Val Arg
675                 680                 685                 690

GAA AGC CCC AAC ATT ACA GAC CGG TGG ATC CTG TCC TTC ATG CAG TCT        2347
Glu Ser Pro Asn Ile Thr Asp Arg Trp Ile Leu Ser Phe Met Gln Ser
            695                 700                 705

CTC ATT GGC TTC TTT GAG ACT GAA ATG GCA GCT TAT AGG CTT TAT ACT        2395
Leu Ile Gly Phe Phe Glu Thr Glu Met Ala Ala Tyr Arg Leu Tyr Thr
                710                 715                 720

GTG GTG CCT CGC CTG GTC AAG TTT GTA GAT ATT CTG ACC AAT TGG TAT        2443
Val Val Pro Arg Leu Val Lys Phe Val Asp Ile Leu Thr Asn Trp Tyr
            725                 730                 735

GTT AGA ATG AAC CGC AGA AGA TTA AAG GGT GAA AAT GGG ATG GAG GAT        2491
Val Arg Met Asn Arg Arg Arg Leu Lys Gly Glu Asn Gly Met Glu Asp
    740                 745                 750

TGT GTC ATG GCC CTA GAA ACC TTG TTT AGT GTT CTG CTT TCT CTT TGC        2539
Cys Val Met Ala Leu Glu Thr Leu Phe Ser Val Leu Leu Ser Leu Cys
755                 760                 765                 770

AGA CTT ATG GCT CCC TAC ACA CCT TTT CTC ACT GAA TTG ATG TAC CAG        2587
Arg Leu Met Ala Pro Tyr Thr Pro Phe Leu Thr Glu Leu Met Tyr Gln
            775                 780                 785

AAT CTA AAG GTG CTG ATT GAC CCT GTT TCT GTT CAG GAC AAG GAC ACA        2635
Asn Leu Lys Val Leu Ile Asp Pro Val Ser Val Gln Asp Lys Asp Thr
                790                 795                 800

CTC AGC ATT CAC TAC CTC ATG CTG CCC CGT GTT CGA GAA GAA TTG ATT        2683
Leu Ser Ile His Tyr Leu Met Leu Pro Arg Val Arg Glu Glu Leu Ile
            805                 810                 815

GAC AAG AAA ACA GAG AGT GCA GTA TCT CAG ATG CAG TCT GTG ATT GAA        2731
Asp Lys Lys Thr Glu Ser Ala Val Ser Gln Met Gln Ser Val Ile Glu
    820                 825                 830

CTT GGA AGA GTG ATC AGA GAC CGA AAA ACT ATT CCC ATA AAG TAT CCT        2779
Leu Gly Arg Val Ile Arg Asp Arg Lys Thr Ile Pro Ile Lys Tyr Pro
835                 840                 845                 850

TTG AAA GAA ATT GTG GTT ATC CAT CAA GAT CCA GAA GCT CTT AAA GAT        2827
Leu Lys Glu Ile Val Val Ile His Gln Asp Pro Glu Ala Leu Lys Asp
            855                 860                 865

ATC AAG TCT TTG GAG AAG TAT ATC ATT GAG GAA CTC AAT GTT CGA AAA        2875
Ile Lys Ser Leu Glu Lys Tyr Ile Ile Glu Glu Leu Asn Val Arg Lys
                870                 875                 880

GTT ACA CTG TCT ACA GAT AAA AAC AAG TAT GGC ATT CGG CTA AGG GCA        2923
Val Thr Leu Ser Thr Asp Lys Asn Lys Tyr Gly Ile Arg Leu Arg Ala
            885                 890                 895

GAA CCA GAT CAC ATG GTC CTG GGG AAG CGT CTG AAG GGA GCC TTT AAG        2971
Glu Pro Asp His Met Val Leu Gly Lys Arg Leu Lys Gly Ala Phe Lys
        900                 905                 910
```

| | | | | | | | | | | | | | | | | |
|---|---|---|---|---|---|---|---|---|---|---|---|---|---|---|---|---|
| GCA | GTG | ATG | ACG | TCC | ATC | AAG | CAG | TTG | AGC | AGT | GAG | GAG | CTG | GAG | CAG | 3019 |
| Ala 915 | Val | Met | Thr | Ser | Ile 920 | Lys | Gln | Leu | Ser | Ser 925 | Glu | Glu | Leu | Glu | Gln 930 | |
| TTC | CAG | AAG | ACT | GGG | ACC | ATT | GTT | GTG | GAA | GGC | CAT | GAA | TTG | CAC | GAT | 3067 |
| Phe | Gln | Lys | Thr | Gly 935 | Thr | Ile | Val | Val | Glu 940 | Gly | His | Glu | Leu | His 945 | Asp | |
| GAA | GAC | ATC | CGC | CTC | ATG | TAC | ACC | TTT | GAT | CAG | GCC | ACA | GGT | GGG | ACT | 3115 |
| Glu | Asp | Ile | Arg 950 | Leu | Met | Tyr | Thr | Phe 955 | Asp | Gln | Ala | Thr | Gly 960 | Gly | Thr | |
| GCG | CAA | TTT | GAA | GCA | CAC | TCA | GAT | GCT | CAG | GCT | TTG | GTC | CTC | TTA | GAT | 3163 |
| Ala | Gln | Phe 965 | Glu | Ala | His | Ser | Asp 970 | Ala | Gln | Ala | Leu | Val 975 | Leu | Leu | Asp | |
| GTC | ACT | CCT | GAC | CAG | TCA | ATG | GTA | GAT | GAA | GGA | ATG | GCT | CGG | GAA | GTC | 3211 |
| Val | Thr | Pro | Asp 980 | Gln | Ser | Met | Val 985 | Asp | Glu | Gly | Met 990 | Ala | Arg | Glu | Val | |
| ATC | AAT | CGC | ATA | CAG | AAA | CTT | CGC | AAA | AAG | TGC | AAT | CTG | GTT | CCA | ACT | 3259 |
| Ile 995 | Asn | Arg | Ile | Gln 1000 | Lys | Leu | Arg | Lys | Lys 1005 | Cys | Asn | Leu | Val | Pro 1010 | Thr | |
| GAT | GAA | ATC | ACA | GTG | TAC | TAT | AAA | GCA | AAG | TCT | GAA | GGA | ACA | TAT | CTG | 3307 |
| Asp | Glu | Ile | Thr | Val 1015 | Tyr | Tyr | Lys | Ala | Lys 1020 | Ser | Glu | Gly | Thr | Tyr 1025 | Leu | |
| AAT | AGT | GTT | ATT | GAA | AGC | CAC | ACA | GAG | TTC | ATA | TTT | ACC | ACC | ATA | AAG | 3355 |
| Asn | Ser | Val | Ile 1030 | Glu | Ser | His | Thr | Glu 1035 | Phe | Ile | Phe | Thr | Thr 1040 | Ile | Lys | |
| GCT | CCC | TTG | AAA | CCA | TAT | CCA | GTT | TCT | CCA | TCG | GAT | AAA | GTC | CTT | ATT | 3403 |
| Ala | Pro | Leu | Lys 1045 | Pro | Tyr | Pro | Val | Ser 1050 | Pro | Ser | Asp | Lys | Val 1055 | Leu | Ile | |
| CAA | GAA | AAA | ACA | CAG | TTG | AAG | GGA | TCT | GAA | CTG | GAA | ATT | ACA | CTC | ACC | 3451 |
| Gln | Glu | Lys | Thr 1060 | Gln | Leu | Lys | Gly | Ser 1065 | Glu | Leu | Glu | Ile | Thr 1070 | Leu | Thr | |
| AGA | GGA | TCT | TCC | CTT | CCT | GGT | CCT | GCT | TGT | GCA | TAT | GTC | AAT | CTT | AAC | 3499 |
| Arg 1075 | Gly | Ser | Ser | Leu | Pro 1080 | Gly | Pro | Ala | Cys | Ala 1085 | Tyr | Val | Asn | Leu | Asn 1090 | |
| ATT | TGT | GCA | AAT | GGC | AGT | GAA | CAA | GGT | GGA | GTA | TTG | CTC | CTG | GAA | AAT | 3547 |
| Ile | Cys | Ala | Asn | Gly 1095 | Ser | Glu | Gln | Gly | Gly 1100 | Val | Leu | Leu | Leu | Glu 1105 | Asn | |
| CCA | AAA | GGT | GAC | AAT | AGG | TTG | GAC | CTT | TTA | AAG | CTG | AAG | AGT | GTT | GTC | 3595 |
| Pro | Lys | Gly | Asp | Asn 1110 | Arg | Leu | Asp | Leu | Leu 1115 | Lys | Leu | Lys | Ser | Val 1120 | Val | |
| ACT | AGC | ATT | TTT | GGT | GTG | AAA | AAT | ACA | GAG | CTG | GCT | GTC | TTC | CAT | GAT | 3643 |
| Thr | Ser | Ile | Phe 1125 | Gly | Val | Lys | Asn | Thr 1130 | Glu | Leu | Ala | Val | Phe 1135 | His | Asp | |
| GAA | ACA | GAA | ATA | CAA | AAC | CAA | ACT | GAC | TTA | CTG | AGT | CTT | AGT | GGA | AAA | 3691 |
| Glu | Thr | Glu | Ile 1140 | Gln | Asn | Gln | Thr | Asp 1145 | Leu | Leu | Ser | Leu | Ser 1150 | Gly | Lys | |
| ACA | CTT | TGT | GTG | ACT | GCA | GGA | TCG | GCT | CCC | TCT | CTG | ATC | AAC | AGT | TCT | 3739 |
| Thr | Leu | Cys | Val 1155 | Thr | Ala | Gly | Ser | Ala 1160 | Pro | Ser | Leu | Ile | Asn 1165 | Ser | Ser 1170 | |
| AGT | ACT | CTT | CTT | TGT | CAG | TAT | ATC | AAC | CTA | CAG | CTC | CTG | AAT | GCA | AAG | 3787 |
| Ser | Thr | Leu | Leu | Cys 1175 | Gln | Tyr | Ile | Asn | Leu 1180 | Gln | Leu | Leu | Asn | Ala 1185 | Lys | |
| CCA | CAA | GAG | TGT | TTA | ATG | GGG | ACA | GTG | GGC | ACT | CTC | CTG | CTT | GAA | AAC | 3835 |
| Pro | Gln | Glu | Cys | Leu 1190 | Met | Gly | Thr | Val | Gly 1195 | Thr | Leu | Leu | Leu | Glu 1200 | Asn | |
| CCA | CTT | GGG | CAG | AAT | GGA | CTC | ACC | CAC | CAA | GGT | CTT | CTG | TAT | GAA | GCA | 3883 |
| Pro | Leu | Gly | Gln | Asn 1205 | Gly | Leu | Thr | His | Gln 1210 | Gly | Leu | Leu | Tyr | Glu 1215 | Ala | |
| GCC | AAG | GTG | TTT | GGC | CTT | CGG | AGC | AGG | AAG | CTA | AAG | CTG | TTT | CTG | AAT | 3931 |
| Ala | Lys | Val | Phe 1220 | Gly | Leu | Arg | Ser | Arg 1225 | Lys | Leu | Lys | Leu | Phe 1230 | Leu | Asn | |

-continued

```
GAG ACC CAA ACG CAG GAA ATT ACA GAA GAC ATC CCC GTG AAG ACT TTG     3979
Glu Thr Gln Thr Gln Glu Ile Thr Glu Asp Ile Pro Val Lys Thr Leu
1235                1240                1245                1250

AAT ATG AAG ACT GTG TAT GTT TCT GTG TTA CCA ACA ACA GCA GAC TTC     4027
Asn Met Lys Thr Val Tyr Val Ser Val Leu Pro Thr Thr Ala Asp Phe
            1255                1260                1265
```

| | |
|---|---:|
| TAGCATGTAC TTATCAATGT TGTTCGGTCA GCCCTTCCCT AATTACACCT ATCCCCTACA | 4087 |
| CATACATGCA CATAGACACA CACATGAACA CACTGAAGAT ATTTCCTTCA GGTGTGTGTA | 4147 |
| AAATATGCTG CTTGGATTGA AATTCAAATG GGATTGATTA GTCAAGTAAC TTGAGACCTC | 4207 |
| ACAGTAATCT TCACACTTAA CCTTAGACAC CTATGCAGTC ATGTTGGGAG CAGGTTACAA | 4267 |
| TGTTACTTCA GCCCACAGTT TATTTCTATA CTTGAGTTCT TAAGTACAGA AGATAGAAGT | 4327 |
| GATTTAAATG GCATAGTATA TATATCATTT TCTGGCCTTT TAAAATTTAT TTGAGACCTC | 4387 |
| TTGATGAAAT GGACATATTA TATATTTCTG CCACCTGGAT TTTCCTGGAT AATTTGATGG | 4447 |
| AATATTTTAA GTTCAGTAA ATCAGAACAA TAAACAAACT CAGATATAAA AAA | 4500 |

( 2 ) INFORMATION FOR SEQ ID NO:4:

( i ) SEQUENCE CHARACTERISTICS:
        ( A ) LENGTH: 1266 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met Ser Asn Lys Met Leu Gln Gln Val Pro Glu Asn Ile Asn Phe Pro
 1               5                  10                  15

Ala Glu Glu Glu Lys Ile Leu Glu Phe Trp Thr Glu Phe Asn Cys Phe
                20                  25                  30

Gln Glu Cys Leu Lys Gln Ser Lys His Lys Pro Lys Phe Thr Phe Tyr
            35                  40                  45

Asp Gly Pro Pro Phe Ala Thr Gly Leu Pro His Tyr His Ile Leu
        50                  55                  60

Ala Gly Thr Ile Lys Asp Ile Val Thr Arg Tyr Ala His Gln Ser Gly
65                  70                  75                  80

Phe His Val Asp Arg Arg Phe Gly Trp Asp Cys His Gly Leu Pro Val
                85                  90                  95

Glu Tyr Glu Ile Asp Lys Thr Leu Gly Ile Arg Gly Pro Glu Asp Val
            100                 105                 110

Ala Lys Met Gly Ile Thr Glu Tyr Asn Asn Gln Cys Arg Ala Ile Val
        115                 120                 125

Met Arg Tyr Ser Ala Glu Trp Lys Ser Thr Val Ser Arg Leu Gly Arg
    130                 135                 140

Trp Ile Asp Phe Asp Asn Asp Tyr Lys Thr Leu Tyr Pro Gln Phe Met
145                 150                 155                 160

Glu Ser Val Trp Trp Val Phe Lys Gln Leu Tyr Asp Lys Gly Leu Val
                165                 170                 175

Tyr Arg Gly Val Lys Val Met Pro Phe Ser Thr Ala Cys Asn Thr Pro
            180                 185                 190

Leu Ser Asn Phe Glu Ser His Gln Asn Tyr Lys Asp Val Gln Asp Pro
        195                 200                 205

Ser Val Phe Val Thr Phe Pro Leu Glu Glu Asp Glu Thr Val Ser Leu
    210                 215                 220

Val Ala Trp Thr Thr Thr Pro Trp Thr Leu Pro Ser Asn Leu Ala Val
225                 230                 235                 240
```

```
Cys Val Asn Pro Glu Met Gln Tyr Val Lys Ile Lys Asp Val Ala Arg
                245                 250                 255
Gly Arg Leu Leu Ile Leu Met Glu Ala Arg Leu Ser Ala Leu Tyr Lys
            260                 265             270
Leu Glu Ser Asp Tyr Glu Ile Leu Glu Arg Phe Pro Gly Ala Tyr Leu
        275                 280             285
Lys Gly Lys Lys Tyr Arg Pro Leu Phe Asp Tyr Phe Leu Lys Cys Lys
    290                 295             300
Glu Asn Gly Ala Phe Thr Val Leu Val Asp Asn Tyr Val Lys Glu Glu
305                 310                 315                 320
Glu Gly Thr Gly Val His Gln Ala Pro Tyr Phe Gly Ala Glu Asp
                325             330                 335
Tyr Arg Val Cys Met Asp Phe Asn Ile Ile Arg Lys Asp Ser Leu Pro
                340                 345             350
Val Cys Pro Val Asp Ala Ser Gly Cys Phe Thr Thr Glu Val Thr Asp
        355                 360             365
Phe Ala Gly Gln Tyr Val Lys Asp Ala Asp Lys Ser Ile Ile Arg Thr
    370                 375             380
Leu Lys Glu Gln Gly Arg Leu Leu Val Ala Thr Thr Phe Thr His Ser
385                 390                 395                 400
Tyr Pro Phe Cys Trp Arg Ser Asp Thr Pro Leu Ile Tyr Lys Ala Val
                405                 410             415
Pro Ser Trp Phe Val Arg Val Glu Asn Met Val Asp Gln Leu Leu Arg
            420                 425             430
Asn Asn Asp Leu Cys Tyr Trp Val Pro Glu Leu Val Arg Glu Lys Arg
            435                 440             445
Phe Gly Asn Trp Leu Lys Asp Ala Arg Asp Trp Thr Ile Ser Arg Asn
    450                 455             460
Arg Tyr Trp Gly Thr Pro Ile Pro Leu Trp Val Ser Asp Asp Phe Glu
465                 470                 475                 480
Glu Val Val Cys Ile Gly Ser Val Ala Glu Leu Glu Glu Leu Ser Gly
                485             490                 495
Ala Lys Ile Ser Asp Leu His Arg Glu Ser Val Asp His Leu Thr Ile
                500                 505             510
Pro Ser Arg Cys Gly Lys Gly Ser Leu His Arg Ile Ser Glu Val Phe
            515                 520             525
Asp Cys Trp Phe Glu Ser Gly Ser Met Pro Tyr Ala Gln Val His Tyr
        530                 535             540
Pro Phe Glu Asn Lys Arg Glu Phe Glu Asp Ala Phe Pro Ala Asp Phe
545                 550                 555                 560
Ile Ala Glu Gly Ile Asp Gln Thr Arg Gly Trp Phe Tyr Thr Leu Leu
                565                 570             575
Val Leu Ala Thr Ala Leu Phe Gly Gln Pro Pro Phe Lys Asn Val Ile
            580                 585             590
Val Asn Gly Leu Val Leu Ala Ser Asp Gly Gln Lys Met Ser Lys Arg
        595                 600             605
Lys Lys Asn Tyr Pro Asp Pro Val Ser Ile Ile Gln Lys Tyr Gly Ala
    610                 615             620
Asp Ala Leu Arg Leu Tyr Leu Ile Asn Ser Pro Val Val Arg Ala Glu
625                 630                 635                 640
Asn Leu Arg Phe Lys Glu Glu Gly Val Arg Asp Val Leu Lys Asp Val
                645                 650             655
Leu Leu Pro Trp Tyr Asn Ala Tyr Arg Phe Leu Ile Gln Asn Val Leu
```

|     |     |     |     |     |     |     |     |     |     |     |     |     |     |     |
| --- | --- | --- | --- | --- | --- | --- | --- | --- | --- | --- | --- | --- | --- | --- |
| Arg | Leu | Gln 675 | Lys | Glu | Glu | Ile 680 | Glu | Phe | Leu | Tyr | Asn 685 | Glu | Asn | Thr |
| Val | Arg 690 | Glu | Ser | Pro | Asn 695 | Thr | Asp | Arg | Trp 700 | Ile | Leu | Ser | Phe | Met |
| Gln 705 | Ser | Leu | Ile | Gly | Phe 710 | Phe | Glu | Thr | Glu | Met 715 | Ala | Ala | Tyr | Arg | Leu 720 |
| Tyr | Thr | Val | Val | Pro 725 | Arg | Leu | Val | Lys | Phe 730 | Val | Asp | Ile | Leu | Thr 735 | Asn |
| Trp | Tyr | Val | Arg 740 | Met | Asn | Arg | Arg | Arg 745 | Leu | Lys | Gly | Glu | Asn 750 | Gly | Met |
| Glu | Asp | Cys 755 | Val | Met | Ala | Leu | Glu 760 | Thr | Leu | Phe | Ser | Val 765 | Leu | Leu | Ser |
| Leu | Cys 770 | Arg | Leu | Met | Ala | Pro 775 | Tyr | Thr | Pro | Phe | Leu 780 | Thr | Glu | Leu | Met |
| Tyr 785 | Gln | Asn | Leu | Lys | Val 790 | Leu | Ile | Asp | Pro | Val 795 | Ser | Val | Gln | Asp | Lys 800 |
| Asp | Thr | Leu | Ser | Ile 805 | His | Tyr | Leu | Met | Leu 810 | Pro | Arg | Val | Arg | Glu 815 | Glu |
| Leu | Ile | Asp | Lys 820 | Lys | Thr | Glu | Ser | Ala 825 | Val | Ser | Gln | Met | Gln 830 | Ser | Val |
| Ile | Glu | Leu 835 | Gly | Arg | Val | Ile | Arg 840 | Asp | Arg | Lys | Thr | Ile 845 | Pro | Ile | Lys |
| Tyr | Pro 850 | Leu | Lys | Glu | Ile | Val 855 | Val | Ile | His | Gln | Asp 860 | Pro | Glu | Ala | Leu |
| Lys 865 | Asp | Ile | Lys | Ser | Leu 870 | Glu | Lys | Tyr | Ile | Ile 875 | Glu | Glu | Leu | Asn | Val 880 |
| Arg | Lys | Val | Thr | Leu 885 | Ser | Thr | Asp | Lys | Asn 890 | Lys | Tyr | Gly | Ile | Arg 895 | Leu |
| Arg | Ala | Glu | Pro 900 | Asp | His | Met | Val | Leu 905 | Gly | Lys | Arg | Leu | Lys 910 | Gly | Ala |
| Phe | Lys | Ala 915 | Val | Met | Thr | Ser | Ile 920 | Lys | Gln | Leu | Ser | Ser 925 | Glu | Glu | Leu |
| Glu | Gln 930 | Phe | Gln | Lys | Thr | Gly 935 | Thr | Ile | Val | Val | Glu 940 | Gly | His | Glu | Leu |
| His 945 | Asp | Glu | Asp | Ile | Arg 950 | Leu | Met | Tyr | Thr | Phe 955 | Asp | Gln | Ala | Thr | Gly 960 |
| Gly | Thr | Ala | Gln | Phe 965 | Glu | Ala | His | Ser | Asp 970 | Ala | Gln | Ala | Leu | Val 975 | Leu |
| Leu | Asp | Val | Thr 980 | Pro | Asp | Gln | Ser | Met 985 | Val | Asp | Glu | Gly | Met 990 | Ala | Arg |
| Glu | Val | Ile 995 | Asn | Arg | Ile | Gln | Lys 1000 | Leu | Arg | Lys | Lys | Cys 1005 | Asn | Leu | Val |
| Pro | Thr 1010 | Asp | Glu | Ile | Thr | Val 1015 | Tyr | Tyr | Lys | Ala | Lys 1020 | Ser | Glu | Gly | Thr |
| Tyr 1025 | Leu | Asn | Ser | Val | Ile 1030 | Glu | Ser | His | Thr | Glu 1035 | Phe | Ile | Phe | Thr | Thr 1040 |
| Ile | Lys | Ala | Pro | Leu 1045 | Lys | Pro | Tyr | Pro | Val 1050 | Ser | Pro | Ser | Asp | Lys 1055 | Val |
| Leu | Ile | Gln | Glu 1060 | Lys | Thr | Gln | Leu | Lys 1065 | Gly | Ser | Glu | Leu | Glu 1070 | Ile | Thr |
| Leu | Thr | Arg 1075 | Gly | Ser | Ser | Leu | Pro 1080 | Gly | Pro | Ala | Cys | Ala 1085 | Tyr | Val | Asn |

| | | | | | | | | | | | | | |
|---|---|---|---|---|---|---|---|---|---|---|---|---|---|
| Leu | Asn | Ile | Cys | Ala | Asn | Gly | Ser | Glu | Gln | Gly | Gly | Val | Leu Leu Leu |
| | 1090 | | | | 1095 | | | | | 1100 | | | |
| Glu | Asn | Pro | Lys | Gly | Asp | Asn | Arg | Leu | Asp | Leu | Leu | Lys | Leu Lys Ser |
| 1105 | | | | | 1110 | | | | 1115 | | | | 1120 |
| Val | Val | Thr | Ser | Ile | Phe | Gly | Val | Lys | Asn | Thr | Glu | Leu | Ala Val Phe |
| | | | | 1125 | | | | | 1130 | | | | 1135 |
| His | Asp | Glu | Thr | Glu | Ile | Gln | Asn | Gln | Thr | Asp | Leu | Leu | Ser Leu Ser |
| | | | 1140 | | | | | 1145 | | | | 1150 | |
| Gly | Lys | Thr | Leu | Cys | Val | Thr | Ala | Gly | Ser | Ala | Pro | Ser | Leu Ile Asn |
| | | | 1155 | | | | 1160 | | | | | 1165 | |
| Ser | Ser | Ser | Thr | Leu | Leu | Cys | Gln | Tyr | Ile | Asn | Leu | Gln | Leu Leu Asn |
| | 1170 | | | | | 1175 | | | | | 1180 | | |
| Ala | Lys | Pro | Gln | Glu | Cys | Leu | Met | Gly | Thr | Val | Gly | Thr | Leu Leu Leu |
| 1185 | | | | | 1190 | | | | | 1195 | | | 1200 |
| Glu | Asn | Pro | Leu | Gly | Gln | Asn | Gly | Leu | Thr | His | Gln | Gly | Leu Leu Tyr |
| | | | | 1205 | | | | | 1210 | | | | 1215 |
| Glu | Ala | Ala | Lys | Val | Phe | Gly | Leu | Arg | Ser | Arg | Lys | Leu | Lys Leu Phe |
| | | | 1220 | | | | | 1225 | | | | 1230 | |
| Leu | Asn | Glu | Thr | Gln | Thr | Gln | Glu | Ile | Thr | Glu | Asp | Ile | Pro Val Lys |
| | | | 1235 | | | | | 1240 | | | | 1245 | |
| Thr | Leu | Asn | Met | Lys | Thr | Val | Tyr | Val | Ser | Val | Leu | Pro | Thr Thr Ala |
| | 1250 | | | | | 1255 | | | | | 1260 | | |
| Asp | Phe | | | | | | | | | | | | |
| 1265 | | | | | | | | | | | | | |

( 2 ) INFORMATION FOR SEQ ID NO:5:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:5:

CCCTCAGCAA CCATATCCTC CAACAAGTTC CAGAAA        36

( 2 ) INFORMATION FOR SEQ ID NO:6:

( i ) SEQUENCE CHARACTERISTICS:
        ( A ) LENGTH: 8 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:6:

Gly Trp Asp Thr His Gly Xaa Pro
    1                5

( 2 ) INFORMATION FOR SEQ ID NO:7:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="PCR primer"

( i x ) FEATURE:

(A) NAME/KEY: modified_base
(B) LOCATION: 11
(D) OTHER INFORMATION: /mod_base=i (ix) FEATURE:
(A) NAME/KEY: modified_base
(B) LOCATION: 20
(D) OTHER INFORMATION: /mod_base=i (ix) FEATURE:
(A) NAME/KEY: modified_base
(B) LOCATION: 26
(D) OTHER INFORMATION: /mod_base=i (ix) FEATURE:
(A) NAME/KEY: modified_base
(B) LOCATION: 29
(D) OTHER INFORMATION: /mod_base=i (xi) SEQUENCE DESCRIPTION: SEQ ID NO:7:

GCGAATTCGG NTGGGAYACN CAYGGNSTNC C    31

(2) INFORMATION FOR SEQ ID NO:8:

(i) SEQUENCE CHARACTERISTICS:
(A) LENGTH: 8 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:8:

Gly Trp Asp Cys His Gly Leu Pro
1               5

(2) INFORMATION FOR SEQ ID NO:9:

(i) SEQUENCE CHARACTERISTICS:
(A) LENGTH: 31 base pairs
(B) TYPE: nucleic acid
(C) STRANDEDNESS: single
(D) TOPOLOGY: linear (ii) MOLECULE TYPE: other nucleic acid
(A) DESCRIPTION: /desc ="PCR primer"

(ix) FEATURE:
(A) NAME/KEY: modified_base
(B) LOCATION: 11
(D) OTHER INFORMATION: /mod_base=i (ix) FEATURE:
(A) NAME/KEY: modified_base
(B) LOCATION: 26
(D) OTHER INFORMATION: /mod_base=i (ix) FEATURE:
(A) NAME/KEY: modified_base
(B) LOCATION: 29
(D) OTHER INFORMATION: /mod_base=i (xi) SEQUENCE DESCRIPTION: SEQ ID NO:9:

GCGAATTCGG NTGGGAYTGY CAYGGNCTNC C    31

(2) INFORMATION FOR SEQ ID NO:10:

(i) SEQUENCE CHARACTERISTICS:
(A) LENGTH: 11 amino acids
(B) TYPE: amino acid
(C) STRANDEDNESS:
(D) TOPOLOGY: linear (ii) MOLECULE TYPE: peptide ( x i ) SEQUENCE DESCRIPTION: SEQ ID NO:10:

Xaa Xaa Glu Ser Xaa Trp Trp Xaa Xaa Lys Gln
1               5                       10

( 2 ) INFORMATION FOR SEQ ID NO:11:

( i ) SEQUENCE CHARACTERISTICS:
          ( A ) LENGTH: 32 base pairs
          ( B ) TYPE: nucleic acid
          ( C ) STRANDEDNESS: single
          ( D ) TOPOLOGY: linear ( i i ) MOLECULE TYPE: other nucleic acid
          ( A ) DESCRIPTION: /desc ="PCR primer"

( i x ) FEATURE:
          ( A ) NAME/KEY: modified_base
          ( B ) LOCATION: 12
          ( D ) OTHER INFORMATION: /mod_base=i ( i x ) FEATURE:
          ( A ) NAME/KEY: modified_base
          ( B ) LOCATION: 15
          ( D ) OTHER INFORMATION: /mod_base=i ( i x ) FEATURE:
          ( A ) NAME/KEY: modified_base
          ( B ) LOCATION: 24
          ( D ) OTHER INFORMATION: /mod_base=i ( i x ) FEATURE:
          ( A ) NAME/KEY: modified_base
          ( B ) LOCATION: 27
          ( D ) OTHER INFORMATION: /mod_base=i ( x i ) SEQUENCE DESCRIPTION: SEQ ID NO:11:

TWYATGGART CNACNTGGTG GGYNTTNAAR CA                          3 2

( 2 ) INFORMATION FOR SEQ ID NO:12:

( i ) SEQUENCE CHARACTERISTICS:
          ( A ) LENGTH: 9 amino acids
          ( B ) TYPE: amino acid
          ( C ) STRANDEDNESS:
          ( D ) TOPOLOGY: linear ( i i ) MOLECULE TYPE: peptide ( x i ) SEQUENCE DESCRIPTION: SEQ ID NO:12:

Arg Gln Arg Xaa Trp Gly Xaa Pro Xaa
1               5

( 2 ) INFORMATION FOR SEQ ID NO:13:

( i ) SEQUENCE CHARACTERISTICS:
          ( A ) LENGTH: 33 base pairs
          ( B ) TYPE: nucleic acid
          ( C ) STRANDEDNESS: single
          ( D ) TOPOLOGY: linear ( i i ) MOLECULE TYPE: other nucleic acid
          ( A ) DESCRIPTION: /desc ="PCR primer"

( i x ) FEATURE:
          ( A ) NAME/KEY: modified_base
          ( B ) LOCATION: 10
          ( D ) OTHER INFORMATION: /mod_base=i ( i x ) FEATURE:
          ( A ) NAME/KEY: modified_base
          ( B ) LOCATION: 16
          ( D ) OTHER INFORMATION: /mod_base=i (i x) FEATURE:
    (A) NAME/KEY: modified_base
    (B) LOCATION: 25
    (D) OTHER INFORMATION: /mod_base=i (i x) FEATURE:
    (A) NAME/KEY: modified_base
    (B) LOCATION: 28
    (D) OTHER INFORMATION: /mod_base=i (i x) FEATURE:
    (A) NAME/KEY: modified_base
    (B) LOCATION: 31
    (D) OTHER INFORMATION: /mod_base=i (x i) SEQUENCE DESCRIPTION: SEQ ID NO:13:

GCGAATTCGN CARCGNTAYT GGGGNRTNCC NAT    33

(2) INFORMATION FOR SEQ ID NO:14:

(i) SEQUENCE CHARACTERISTICS:
    (A) LENGTH: 9 amino acids
    (B) TYPE: amino acid
    (C) STRANDEDNESS:
    (D) TOPOLOGY: linear (i i) MOLECULE TYPE: peptide (x i) SEQUENCE DESCRIPTION: SEQ ID NO:14:

Arg Xaa Arg Xaa Trp Gly Xaa Pro Xaa
 1               5

(2) INFORMATION FOR SEQ ID NO:15:

(i) SEQUENCE CHARACTERISTICS:
    (A) LENGTH: 33 base pairs
    (B) TYPE: nucleic acid
    (C) STRANDEDNESS: single
    (D) TOPOLOGY: linear (i i) MOLECULE TYPE: other nucleic acid
    (A) DESCRIPTION: /desc ="PCR primer"

(i x) FEATURE:
    (A) NAME/KEY: modified_base
    (B) LOCATION: 10
    (D) OTHER INFORMATION: /mod_base=i (i x) FEATURE:
    (A) NAME/KEY: modified_base
    (B) LOCATION: 16
    (D) OTHER INFORMATION: /mod_base=i (i x) FEATURE:
    (A) NAME/KEY: modified_base
    (B) LOCATION: 25
    (D) OTHER INFORMATION: /mod_base=i (i x) FEATURE:
    (A) NAME/KEY: modified_base
    (B) LOCATION: 28
    (D) OTHER INFORMATION: /mod_base=i (i x) FEATURE:
    (A) NAME/KEY: modified_base
    (B) LOCATION: 31
    (D) OTHER INFORMATION: /mod_base=i (x i) SEQUENCE DESCRIPTION: SEQ ID NO:15:

GCGAATTCGN AAYCGNTWYT GGGGNACNCC NMT    33

(2) INFORMATION FOR SEQ ID NO:16:

(i) SEQUENCE CHARACTERISTICS:

(A) LENGTH: 10 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:16:

Glu Gly Xaa Asp Gln Xaa Arg Gly Trp Phe
    1               5                   10

(2) INFORMATION FOR SEQ ID NO:17:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc ="PCR primer"

(ix) FEATURE:
        (A) NAME/KEY: modified_base
        (B) LOCATION: 15
        (D) OTHER INFORMATION: /mod_base=i (ix) FEATURE:
        (A) NAME/KEY: modified_base
        (B) LOCATION: 18
        (D) OTHER INFORMATION: /mod_base=i (ix) FEATURE:
        (A) NAME/KEY: modified_base
        (B) LOCATION: 21
        (D) OTHER INFORMATION: /mod_base=i (ix) FEATURE:
        (A) NAME/KEY: modified_base
        (B) LOCATION: 30
        (D) OTHER INFORMATION: /mod_base=i (ix) FEATURE:
        (A) NAME/KEY: modified_base
        (B) LOCATION: 33
        (D) OTHER INFORMATION: /mod_base=i (xi) SEQUENCE DESCRIPTION: SEQ ID NO:17:

GCGAATTCRA ACCANCCNCG NGTYTGRTCN WWNCCYTC                            38

(2) INFORMATION FOR SEQ ID NO:18:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc ="PCR primer"

(xi) SEQUENCE DESCRIPTION: SEQ ID NO:18:

CCGTTTGCAT AAGGAGGTCC A                                              21

(2) INFORMATION FOR SEQ ID NO:19:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc ="PCR primer"

( x i ) SEQUENCE DESCRIPTION: SEQ ID NO:19:

CATCATGAAG GCAAAATTCT GTCTT 25

( 2 ) INFORMATION FOR SEQ ID NO:20:

( i ) SEQUENCE CHARACTERISTICS:
    ( A ) LENGTH: 25 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc ="PCR primer"

( x i ) SEQUENCE DESCRIPTION: SEQ ID NO:20:

ACGCCCCGCC TTCCCTGCAG CCCGG 25

( 2 ) INFORMATION FOR SEQ ID NO:21:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc ="PCR primer"

( x i ) SEQUENCE DESCRIPTION: SEQ ID NO:21:

TCTTTCTAAT TTCCATAGCT G 21

( 2 ) INFORMATION FOR SEQ ID NO:22:

( i ) SEQUENCE CHARACTERISTICS:
    ( A ) LENGTH: 33 base pairs
    ( B ) TYPE: nucleic acid
    ( C ) STRANDEDNESS: single
    ( D ) TOPOLOGY: linear ( i i ) MOLECULE TYPE: other nucleic acid ( x i ) SEQUENCE DESCRIPTION: SEQ ID NO:22:

CACCCGAACT CGCATATGGG CAGATACCGG GAC 33

( 2 ) INFORMATION FOR SEQ ID NO:23:

( i ) SEQUENCE CHARACTERISTICS:
    ( A ) LENGTH: 32 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc ="PCR primer"

( x i ) SEQUENCE DESCRIPTION: SEQ ID NO:23:

CCAAGAAGCT TGAAGTAATA ATAGGCGCAT GC 32

( 2 ) INFORMATION FOR SEQ ID NO:24:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc ="PCR primer"

( x i ) SEQUENCE DESCRIPTION: SEQ ID NO:24:

CGTACTGCAG GATTGTATGC TTGGTATAGC                    30

( 2 ) INFORMATION FOR SEQ ID NO:25:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc ="PCR primer"

( x i ) SEQUENCE DESCRIPTION: SEQ ID NO:25:

GGAATTCTGA AAACAACTCA TATAAATACG                    30

( 2 ) INFORMATION FOR SEQ ID NO:26:

( i ) SEQUENCE CHARACTERISTICS:
    ( A ) LENGTH: 32 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc ="PCR primer"

( x i ) SEQUENCE DESCRIPTION: SEQ ID NO:26:

GAGGCGCCCT CTTATCAATC CCTCCTCAA CC                  32

HUMAN ISOLEUCYL-TRNA SYNTHETASE PROTEINS, NUCLEIC ACIDS AND TESTER STRAINS COMPRISING SAME

RELATED APPLICATIONS

This application is a continuation-in-part of U.S. Pat. Ser. No. 08/250,852, filed May 27, 1994 now abondoned, the teachings of which are incorporated herein by reference in their entirety.

BACKGROUND OF THE INVENTION

The aminoacyl-tRNA synthetases are enzymes with the common general function of catalyzing the following reaction:

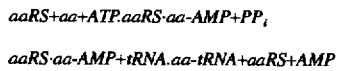

$$aaRS+aa+ATP.aaRS\cdot aa\text{-}AMP+PP_i$$

$$aaRS\cdot aa\text{-}AMP+tRNA.aa\text{-}tRNA+aaRS+AMP$$

(aaRS = aminoacyl-tRNA synthetase; aa = amino acid; ATP = adenosine 5'-triphosphate; AMP = adenosine 5'-monophosphate; $PP_i$ = inorganic pyrophosphate). The second (aminoacylation) step is often referred to as "charging" the tRNA.

Generally, in each eucaryotic organism, there are 20 different cytoplasmic aaRSs, one specific for each amino acid. Eucaryotic organisms also generally encode a separate set of mitochondrial aaRSs. It is known that in the yeast *Saccharomyces cerevisiae*, for example, the cytoplasmic and mitochondrial enzymes are encoded by separate nuclear genes, with the exception of histidyl- and valyl-tRNA synthetases (Natsoulis, G., et al. *Cell* 46:235–243 (1986); Chatton, B. et al., *J. Biol. Chem.* 263:52–57 (1988)). Each aminoacyl-tRNA synthetase enzyme recognizes and reacts with a specific amino acid and one or more tRNAs that recognize the codons specific for that amino acid (cognate tRNAs). To a first approximation, the specificity of the aaRS for the amino acid is determined by proteinamino acid interactions, and the specificity of the aaRS for the tRNA is determined by protein-tRNA interactions, using different sites on the aaRS.

About 25–30% of patients suffering from one or both of the autoimmune inflammatory myopathies polymyositis and dermatomyositis have been found to produce antibodies against their own essential aminoacyl-tRNA synthetase enzymes. The resulting "antisynthetase syndrome" is characterized by a number of clinical presentations, including interstitial lung disease, arthritis, Raynaud's phenomenon and fevers, along with the muscle weakness, dyspnea and dysphagia of myositis. (See, for example, Targoff, I.N. et al., *J. Clin. Invest.* 91:2556–2564 (1993)).

Without sufficiently purified human aminoacyl-tRNA synthetases, the process of diagnosing the "antisynthetase syndrome" and identifying the particular antigenic aminoacyl-tRNA synthetase has been cumbersome. One semiquantitative method available to measure anti-tRNA synthetase antibody in patient serum has been to measure the inhibition of an aminoacylation reaction, testing each one of 20 radioactively labeled amino acids to identify the type of tRNA synthetase. Improved assays would be desirable.

SUMMARY OF THE INVENTION

Because the amino acid sequences of the tRNA synthetases have diverged over evolutionary time, significant differences exist between the structures of the tRNA synthetases of humans and of human pathogens. These differences can be exploited by finding inhibitors of aaRS activity which specifically target a tRNA synthetase of a pathogenic organism. By selectively inactivating one or more aminoacyl-tRNA synthetases of a pathogenic organism with a therapeutic substance that minimally affects the corresponding human enzyme, infections by pathogenic organisms can be controlled.

The invention relates to isolated and/or recombinant nucleic acids which encode isoleucyl-tRNA synthetase (IleRS) of human origin. (Generically, the aminoacyl-tRNA synthetases are the aaRSs; in particular, they are, for example, IleRS.) The invention also relates to recombinant DNA constructs and vectors containing DNA having a sequence which encodes an isoleucyl-tRNA synthetase of human origin, or portions of the enzyme. These nucleic acids and DNA constructs can be employed to produce recombinant isoleucyl-tRNA synthetase of human origin in host cells constructed for this purpose.

A further embodiment of the invention is antisense nucleic acid which can hybridize to the nucleic acid which encodes the amino acid sequence of isoleucyl-tRNA synthetase of humans. In cells, antisense nucleic acid can inhibit the function of an RNA which encodes the isoleucyl-tRNA synthetase.

The invention also relates to proteins or polypeptides which are referred to herein as isolated and/or recombinant human isoleucyl-tRNA synthetases, including functional portions of the tRNA synthetase and fusion proteins comprising a human IleRS or a portion thereof. Isolated, recombinant human isoleucyl-tRNA synthetase can be used in enzymatic activity and other biochemical assays to test substances found to inhibit the isoleucyl-tRNA synthetase or other tRNA synthetase of a pathogenic organism. Isolated, recombinant isoleucyl-tRNA synthetase can also be used in further studies to model substances with inhibitory activity specific for a tRNA synthetase of a pathogen.

These enzymes can be used in the diagnosis and/or monitoring of patients suffering from autoimmune disorders associated with the production of autoantibodies against human isoleucyl-tRNA synthetase. These enzymes are also useful in biochemical separations of isoleucine and quantitations of isoleucine and ATP. Antibodies which bind to these enzymes can be made and can be used in the purification and study of the enzyme, for example in mapping antigenic epitopes of the enzyme. The antibodies can also be used as controls in assays for autoantibodies against human isoleucyl-tRNA synthetase found in samples from patients, such as sera.

Recombinant aminoacyl-tRNA synthetases can be produced in host cells, using cells and methods described herein. Tester strains, which are cells engineered to rely on the function of the tRNA synthetase encoded by an introduced cloned gene, instead of on the endogenous tRNA synthetase gene of the host, are also an embodiment of the invention. Tester strains can be used to test the effectiveness of drug candidates in the inhibition of the essential tRNA synthetase enzyme encoded by an introduced cloned gene, where the introduced cloned gene is from either a pathogen or from an animal (or humans) infected by a pathogen. In this way, potential inhibitors of a tRNA synthetase from a pathogen can be tested for toxicity specifically caused by the inhibition of the corresponding (specific for the same amino acid) animal or human tRNA synthetase enzyme. More specifically, a tester strain can be used to isolate the in vivo effect of a substance administered to the cells on a human isoleucyl-tRNA synthetase; that is, to assess by growth rates and other tests whether the substance has any toxicity by its effect specifically on a human isoleucyl-tRNA synthetase.

DETAILED DESCRIPTION OF THE INVENTION

Nucleic Acids, Constructs and Vectors

Figure 1:
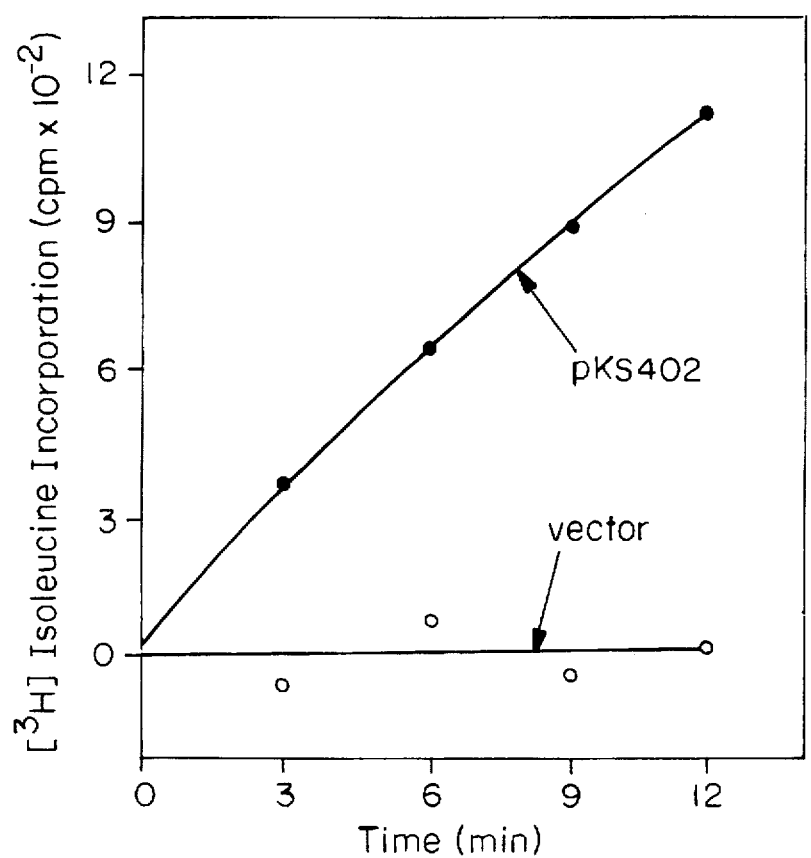
FIG. 1 is a graph of the results of a time course assay for isoleucine charging activity of a human cytoplasmic isoleucyl-tRNA synthetase protein (consisting of amino acid residues 6–1085 of SEQ ID NO:4) using bovine tRNA as substrate (Example 7).

The present invention relates to isolated and/or recombinant (including, e.g., essentially pure) nucleic acids having sequences which encode a human isoleucyl-tRNA synthetase or a portion of a human isoleucyl-tRNA synthetase. In one embodiment, the nucleic acid or portion thereof encodes a protein or polypeptide having at least one function characteristic of a human aminoacyl-tRNA synthetase specific for isoleucine, such as a catalytic activity (e.g., catalysis of aminoacyl-adenylate formation, catalysis of aminoacylation of a tRNA with isoleucine) and/or binding function (e.g., tRNA-, amino acid-, or ATP-binding), an antigenic property characteristic of a human isoleucyl-tRNA synthetase and/or oligomerization function. (Oligomerization activity is the ability of a protein subunit or protein fragment to bind together with one or more other protein subunits or protein fragments, thus altering the quaternary structure of the resulting complex. In one embodiment, the resulting complex has a new or enhanced activity of a type other than oligomerization, compared to the separate components of the complex. For example, "adhesive" fragments with oligomerization activity can bind to another fragment with no catalytic activity of its own to restore or partially restore catalytic activity (Jasin, M., et al., U.S. Pat. No. 4,952,501)).

The present invention also relates more specifically to isolated and/or recombinant nucleic acids having sequences SEQ ID NO:1 and SEQ ID NO:3, or portions thereof. The invention further relates to isolated and/or recombinant nucleic acids that are characterized by (1) their ability to hybridize to (a) a nucleic acid encoding a human isoleucyl-tRNA synthetase such as that having the sequence in SEQ ID NO:1 or SEQ ID NO:3 (b) their complements, or (c) to a portion of any of the foregoing (e.g., a portion comprising the coding region) or (2) by their ability to encode a polypeptide of the amino acid sequence of the enzyme, such as SEQ ID NO:2, SEQ ID NO:4 or functional equivalents thereof (e.g., a polypeptide which aminoacylates isoaccepting cognate tRNA$^{Ile}$ of humans), or (3) by both characteristics. In one embodiment, the percent amino acid sequence similarity between SEQ ID NO:2 and functional equivalents thereof is at least about 70%. In a preferred embodiment, functional equivalents of SEQ ID NO:2 share at least about 75% sequence similarity with SEQ ID NO:2. More preferably, the percent amino acid sequence similarity between SEQ ID NO:2 and functional equivalents thereof is at least about 80%, and still more preferably, at least about 85%. In another embodiment, the percent amino acid sequence similarity between SEQ ID NO:4 and functional equivalents thereof is at least about 80%. In a preferred embodiment, functional equivalents of SEQ ID NO:4 share at least about 85% sequence similarity with SEQ ID NO:4. More preferably, the percent amino acid sequence similarity between SEQ ID NO:4 and functional equivalents thereof is at least about 90%, and still more preferably, at least about 95%. Isolated and/or recombinant nucleic acids meeting these criteria comprise nucleic acids having sequences identical to sequences of naturally occurring human isoleucyl-tRNA synthetase and portions thereof, or variants of the naturally occurring sequences. Such variants include mutants differing by the addition, deletion or substitution of one or more residues, modified nucleic acids in which one or more residues are modified (e.g., DNA or RNA analogs), and mutants comprising one or more modified residues.

Such nucleic acids can be detected and isolated under high stringency conditions or moderate stringency conditions, for example. "High stringency conditions" and "moderate stringency conditions" for nucleic acid hybridizations are explained on pages 2.10.1–2.10.16 (see particularly 2.10.8–11) and pages 6.3.1–6 in *Current Protocols in Molecular Biology* (Ausubel, F. M. et al., eds., Vol. 1, Suppl. 26, 1991), the teachings of which are hereby incorporated by reference. Factors such as probe length, base composition, percent mismatch between the hybridizing sequences, temperature and ionic strength influence the stability of nucleic acid hybrids. Thus, high or moderate stringency conditions can be determined empirically, depending in part upon the characteristics of the known DNA to which other unknown nucleic acids are being compared for sequence similarity.

Isolated and/or recombinant nucleic acids that are characterized by their ability to hybridize to a nucleic acid encoding a human isoleucyl-tRNA synthetase or a portion thereof, or to their complements (e.g. under high or moderate stringency conditions) may further encode a protein or polypeptide having at least one function characteristic of a human tRNA synthetase specific for isoleucine, such as a catalytic activity (e.g., aminoacyl-adenylate formation, aminoacylation of a tRNA with isoleucine), binding function (e.g., tRNA-, amino acid-, or ATP-binding), an antigenic property characteristic of a human isoleucyl-tRNA synthetase, such as the ability to bind antibodies that also bind to naturally-occurring human isoleucyl-tRNA synthetase, and/or oligomerization function. The catalytic or binding function of a protein or polypeptide encoded by hybridizing nucleic acid may be detected by standard enzymatic assays for activity or binding (e.g., assays which monitor aminoacyl-adenylate formation, aminoacylation of tRNA). Functions characteristic of an isoleucyl-tRNA synthetase may also be assessed by in vivo complementation activity or other suitable methods. Enzymatic assays, complementation tests, or other suitable methods can also be used in procedures for the identification and/or isolation of nucleic acids which encode a polypeptide such as a polypeptide of the amino acid sequence SEQ ID NO:4 or functional equivalents thereof. The antigenic properties of proteins or polypeptides encoded by hybridizing nucleic acids can be determined by immunological methods employing antibodies that bind to a human isoleucyl-tRNA synthetase, such as by immunoblot, immunoprecipitation and radioimmunoassay.

Nucleic acids of the present invention can be used in the production of proteins or polypeptides. For example, DNA containing all or part of the coding sequence for human isoleucyl-tRNA synthetase, or DNA which hybridizes to the sequence SEQ ID NO:3, or to its complement, can be incorporated into various constructs and vectors created for further manipulation of sequences or for production of the encoded polypeptide in suitable host cells.

Nucleic acids referred to herein as "isolated" are nucleic acids separated away from the nucleic acids of the genomic DNA or cellular RNA of their source of origin (e.g., as it exists in cells or in a mixture of nucleic acids such as a library), and may have undergone further processing. "Isolated" nucleic acids include nucleic acids obtained by methods described herein, similar methods or other suitable methods, including essentially pure nucleic acids, nucleic acids produced by chemical synthesis, by combinations of biological and chemical methods, and recombinant nucleic acids which are isolated from cells. Nucleic acids referred to herein as "recombinant" are nucleic acids which have been produced by recombinant DNA methodology, including those nucleic acids that are generated by procedures which rely upon a method of artificial recombination or amplification, such as the polymerase chain reaction (PCR) and/or cloning into a vector using restriction enzymes. "Recombinant" nucleic acids are also those that result from recombination events that occur through the natural mechanisms of cells, but are selected for after the introduction to the cells of nucleic acids designed to allow and make probable a desired recombination event.

Portions of the isolated nucleic acids which code for polypeptides having a certain function can be identified and isolated by, for example, the method of Jasin, M., et al., U.S. Pat. No. 4,952,501. The aminoacyl-tRNA synthetases are known to have different quaternary structures, including both monomeric and multimeric structures (e.g., homodimers, tetramers and heteromultimeric $\alpha_2\beta_2$ forms). The aminoacyl-tRNA synthetases are also recognized as having distinct domains or subunits. Thus, as used herein, a nucleic acid which encodes a portion of a human isoleucyl-tRNA synthetase can also refer to one of two or more distinct domains or subunits of said isoleucyl-tRNA synthetase.

A further embodiment of the invention is antisense nucleic acid, which is complementary, in whole or in part, to a target molecule comprising a sense strand, and can hybridize with the target molecule. The target can be DNA, or its RNA counterpart (i.e., wherein T residues of the DNA are U residues in the RNA counterpart). When introduced into a cell, antisense nucleic acid can inhibit the expression of the gene encoded by the sense strand. Antisense nucleic acids can be produced by standard techniques.

In one embodiment, the antisense nucleic acid is wholly or partially complementary to and can hybridize with a target nucleic acid, wherein the target nucleic acid can hybridize to a nucleic acid having the sequence of the complement of the sequence shown in SEQ ID NO:3. For example, antisense nucleic acid can be complementary to a target nucleic acid having the sequence shown in SEQ ID NO:3 or to a portion thereof sufficient to allow hybridization. In another embodiment, the antisense nucleic acid is wholly or partially complementary to and can hybridize with a target nucleic acid which encodes a human isoleucyl-tRNA synthetase.

Proteins

The invention also relates to proteins or polypeptides encoded by nucleic acids of the present invention. The proteins and polypeptides of the present invention can be isolated and/or recombinant. Proteins or polypeptides referred to herein as "isolated" are proteins or polypeptides purified to a state beyond that in which they exist in cells. "Isolated" proteins or polypeptides include proteins or polypeptides obtained by methods described herein, similar methods or other suitable methods, including essentially pure proteins or polypeptides, proteins or polypeptides produced by chemical synthesis, or by combinations of biological and chemical methods, and recombinant proteins or polypeptides which are isolated. Proteins or polypeptides referred to herein as "recombinant" are proteins or polypeptides produced by the expression of recombinant nucleic acids.

In a preferred embodiment, the protein or portion thereof has at least one function characteristic of human isoleucyl-tRNA synthetase, for example, antigenic function (e.g., binding of antibodies that also bind to nonrecombinant human isoleucyl-tRNA synthetase), catalytic activity (e.g., catalysis of aminoacyl-adenylate formation, catalysis of aminoacylation of a tRNA with amino acid), binding function (e.g., tRNA-, amino acid-, or ATP-binding) and/or oligomerization function.

As such, these proteins are referred to as isoleucyl-tRNA synthetases of human origin or human isoleucyl-tRNA synthetases, and include, for example, naturally occurring human isoleucyl-tRNA synthetases, variants (e.g., mutants) of those proteins and/or portions thereof. Such variants include mutants differing by the addition, deletion or substitution of one or more amino acid residues, or modified polypeptides in which one or more residues are modified, and mutants comprising one or more modified residues.

In a particularly preferred embodiment, like naturally occurring human isoleucyl-tRNA synthetases, isolated and/or recombinant human isoleucyl-tRNA synthetases of the present invention aminoacylate the isoaccepting cognate tRNAs of humans with isoleucine in a two-step reaction. In the first step, the isoleucyl-tRNA synthetase catalyzes the covalent linkage of isoleucine to ATP to form an aminoacyl-adenylate complex (isoleucyl-adenylate) with the release of pyrophosphate. In a second step, the isoleucyl-tRNA synthetase catalyzes the covalent linkage of isoleucine to a specific tRNA recognized by the enzyme, releasing AMP.

The invention further relates to fusion proteins, comprising a human isoleucyl-tRNA synthetase (as described above) as a first moiety, linked to a second moiety not occurring in the enzyme as found in nature. Thus, the second moiety can be a single amino acid, peptide or polypeptide. The first moiety can be in an N-terminal location, C-terminal location or internal to the fusion protein. In one embodiment, the fusion protein comprises a human isoleucyl-tRNA synthetase as the first moiety, and a second moiety comprising a linker sequence and affinity ligand.

Fusion proteins can be produced by a variety of methods. For example, some embodiments can be produced by the insertion of a human isoleucyl-tRNA synthetase gene or portion thereof into a suitable expression vector, such as Bluescript SK +/− (Stratagene), pGEX-5X-1 (Pharmacia) or pET-15b (Novagen). The resulting construct is then introduced into a suitable host cell for expression. Upon expression, fusion protein can be purified from a cell lysate by means of a suitable affinity matrix (see e.g., *Current Protocols in Molecular Biology* (Ausubel, F. M. et al., eds., Vol. 2, Suppl. 26, pp. 16.4.1–16.7.8 (1991)).

The invention also relates to isolated and/or recombinant portions of an isoleucyl-tRNA synthetase of human origin. Portions of the enzyme can be made which have full or partial function on their own, or which when mixed together (though fully, partially, or nonfunctional alone), spontaneously assemble with one or more other polypeptides to reconstitute a functional protein having at least one function characteristic of an isoleucyl-tRNA synthetase.

Deletion studies of the *E. coli* alanyl-tRNA synthetase (Jasin, M. et al., U.S. Pat. No. 4,952,501) showed that a large portion (over 400 C-terminal amino acid residues out of a protein 875 amino acid residues long) were unnecessary for specific aminoacylation activity. Large internal deletions also did not destroy enzymatic activity. Internal deletions within the N-terminal region of the alanyl-tRNA synthetase were able to complement a mutant monomeric polypeptide encoded by the alaS5 allele, possibly by the formation of hybrid quaternary structures in which activity of the N-terminal catalytic core is restored.

Based on this type of analysis, conducted in a scheme analogous to that used to study *E. coli* alanyl-tRNA synthetase, portions of a human IleRS enzyme can be made which have at least one function characteristic of a human isoleucyl-tRNA synthetase, such as catalytic, binding function, antigenic function and/or oligomerization function. Studies on the structure and function of the aaRSs provide the basis for being able to divide the aaRS enzymes into functional domains (Schimmel, P., *Current Biology* 1:811–816 (1991)).

The sequences and structures of the catalytic domain of tRNA synthetases already purified and studied are the basis for dividing them into two distinct classes of ten enzymes each, class I and class II (Schimmel, P., *Ann. Rev. Biochem.* 56:125–158 (1987); Webster, T. A., et al., *Science* 226:1315–1317 (1984); Eriani, G. et al., *Nature* 347:203–206 (1990) and Cusack, S., et al., *Nature* 347:249–255 (1990)).

The five members of the subgoup of tRNA synthetases to which human cytoplasmic isoleucyl-tRNA synthetase belongs, like all class I enzymes, have a well-conserved N-terminal nucleotide binding fold responsible for amino acid binding, aminoacyl-adenylate formation, and tRNA acceptor helix docking. The N-terminal nucleotide binding fold is comprised of alternating β-strands and α-helices and a C-terminal domain that is rich in α-helices and that contains residues needed for interactions with the parts of the tRNA distal to the amino acid attachment site (Shepard, A., et al., *Proc. Natl. Acad. Sci. U.S.A.* 89:9964–9968 (1992); Hou, Y.-M., et al., *Proc. Natl. Acad. Sci. U.S.A.* 88:976–980 (1991)). Five enzymes—cysteinyl-, isoleucyl-, leucyl-, methionyl-, and valyl-tRNA synthetases—have been grouped together because they are more closely related in sequence and arrangement of their domains to each other than to the other five members of class I (Hou, Y.-M., et al., *Proc. Natl. Acad. Sci. U.S.A.* 88:976–980 (1991); Eriani, G., et al., *Nucleic Acids Res.* 19:265–269 (1991)). Furthermore, the C-terminal domains of isoleucyl-, leucyl-, methionyl-, cysteinyl- and valyl-tRNA synthetases appear to have a common origin, which is distinct from the C-terminal domain found in other class I enzymes (Shiba, K., et al., *Proc. Natl. Acad. Sci. USA* 89:1880–1884 (1992); Shepard, A., et al., *Proc. Natl. Acad. Sci. U.S.A.* 89:9964–9968 (1992)). In *E. coli*, these five enzymes of class I vary in size from 461 to 951 amino acids and are active as monomers. The size variation is in large part explained by the variability in the lengths of the two insertions designated connective polypeptide 1 (CP1), which is inserted between the second α-helix and third β-strand of the nucleotide binding fold, and CP2, which is placed between the third α-helix and fourth β-strand (Starzyk, R. M., et al., *Science* 237:1614–1618 (1987)). In all of these enzymes, CP1 is the larger of the two insertions and varies in *E. coli* from 61 in cysteinyl-tRNA synthetase to 300 amino acids in isoleucyl-tRNA synthetase (Hou, Y.-M., et al., *Proc. Natl. Acad. Sci. USA* 88:976–980 (1991)). While a portion of CP1 may be deleted from isoleucyl-tRNA synthetase without loss of function (Starzyk, R. M., et al., *Science* 237:1614–1618 (1987)), this insertion is known to facilitate acceptor helix interactions in the related glutaminyl-tRNA synthetase whose three dimensional structure in complex with $tRNA^{Gln}$ has been determined by X-ray crystallography (Rould, M. A. et al., *Science* 246:1135–1142 (1989)). In some tRNA synthetases, this second domain interacts directly with the anticodon (Rould, M. A. et al., *Science* 246:1135–1142 (1989) and Cavarelli, J., et al., *Nature* 362:181–184 (1993)), while in other enzymes there is no contact made between the second domain and the anticodon (Biou, V., et al., *Science* 263:1404–1410 (1994)). To a first approximation, the two domains in class I tRNA synthetases interact with the two distinct domains of the L-shaped tRNA structure. Thus, the recognition elements of the tRNA synthetase and of the tRNA which are needed for the operational RNA code are segregated into discrete protein and RNA domains.

Method of Producing Recombinant aaRSs

Another aspect of the invention relates to a method of producing a human isoleucyl-tRNA synthetase or a portion thereof and to expression systems and host cells containing a vector appropriate for expression of a human isoleucyl-tRNA synthetase.

Cells that express a recombinant aminoacyl-tRNA synthetase or a portion thereof can be made and grown in culture to produce the enzyme for isolation and purification. These cells can be procaryotic or eucaryotic. Examples of procaryotic cells that can be used to express a human isoleucyl-tRNA synthetase include *Escherichia coli*, *Bacillus subtilis* and other bacteria. Examples of eucaryotic cells that can be used to express a human isoleucyl-tRNA synthetase include yeasts such as *Saccharomyces cerevisiae* and *Pichia pastoris*, and other lower eucaryotic cells, and cells of higher eucaryotes such as those from insects and mammals. (See, e.g., Ausubel, F. M. et al., eds. *Current Protocols in Molecular Biology*, Greene Publishing Associates and John Wiley & Sons Inc., (1993)).

To make host cells that produce a recombinant human isoleucyl-tRNA synthetase protein or portion thereof for isolation and purification, as a first step the gene encoding the enzyme can be inserted into a nucleic acid vector, e.g., a DNA vector, such as a plasmid, virus or other suitable replicon, which can be present in a single copy or multiple copies, or the gene can be integrated in a host cell chromosome. Such a suitable replicon contains all or part of the coding sequence for a human isoleucyl-tRNA synthetase, and has the coding sequence under the control of transcription signals and linked to appropriate translation signals to permit translation of the IleRS, portion thereof, or of a fusion protein comprising IleRS or portion thereof. As a second step, the vector can then be introduced into cells by a method appropriate to the type of host cells (e.g., transformation, electroporation, infection). In a third step, for expression from the IleRS gene, the host cells can be maintained under appropriate conditions, e.g., in the presence of inducer, normal growth conditions, etc.).

As a particular example of the above approach to producing recombinant human isoleucyl-tRNA synthetase, a gene encoding a human isoleucyl-tRNA synthetase can be integrated into the genome of a virus that enters the host cells. By infection of the host cells, the components of a system which permits the transcription and translation of a human isoleucyl-tRNA synthetase gene are present in the host cells. Alternatively, an RNA polymerase gene, inducer, or other component required to complete such a gene expression system may be introduced into the host cells already containing the human isoleucyl-tRNA synthetase gene, for example, by means of a virus that enters the host cells and contains the required component. The isoleucyl-tRNA synthetase gene can be under the control of an inducible or constitutive promoter. The promoter can be one that is recognized by the host cell RNA polymerase. The promoter can, alternatively, be one that is recognized by a viral RNA polymerase and is transcribed following infection of the host cells with a virus.

Applications for Human Isoleucyl-tRNA Synthetase Protein

Antibodies directed to human aminoacyl-tRNA synthetases have been found in sera from patients with connective tissue disease, especially patients with idiopathic inflammatory myopathies, diseases such as polymyositis and dermatomyositis, characterized by elevated levels of muscle enzymes and by muscle weakness and wasting. In patients producing these antibodies, there is a significantly higher frequency of intersitial lung disease than in myositis patients not producing these antibodies (Targoff, I.N. and Arnett, F. C., *Am. J. Med.* 88:241–251 (1990)).

Different groups of patients have been studied who make antibodies that bind to alanyl-, histidyl-, threonyl-, glycyl-, or isoleucyl-tRNA synthetase (Targoff, I. N. et al., *J. Clin. Invest.* 91:2556–2564 (1993)). Alanyl-tRNA synthetase, along with histidyl-, threonyl-, and glycyl- tRNA synthetases, exist free in the cytoplasm of human cells tested. In contrast, isoleucyl-tRNA synthetase is a component of a stable, multi-enzyme complex containing at least seven tRNA synthetases (Mirande, M. et al., *Prog. Nucleic Acid Res. Mol. Biol.* 40:95–142 (1991)).

The etiology of the diseases associated with autoantibodies to tRNA synthetases is not understood. One hypothesis postulates that binding of the tRNA synthetase to infecting viral RNA enhances the immunogenicity of the synthetase, when the complex is released from cells damaged in viral infection (Mathews, M. B. and Bernstein, R. M. *Nature* 304:177–179 (1983)). This is in agreement with some studies supporting the theory that the target auto-antigen itself initiates, selects and sustains autoantibody synthesis (Miller, F. W. et al., *Proc. Natl. Acad. Sci. USA* 87:9933–9937 (1990)). An alternative hypothesis for the etiology of autoimmune disorders in general is that immunogenic components of pathogenic organisms, especially parasitic organisms, elicit the production of antibodies that cross-react with similar components of the host (See, for example, Meilof, J. F. et al., *J. Immunol.* 151:5800–5809 "Autoimmunity and Filariasis: Autoantibodies Against Cytoplasmic Cellular Proteins in Sera of Patients with Onchocerciasis" (1993)).

Isolated (e.g., purified), recombinant human isoleucyl-tRNA synthetase can be used in methods to detect anti-isoleucyl-tRNA synthetase antibodies in samples from patients who show the symptoms associated with the autoimmune diseases of antisynthetase syndrome. These methods can be useful not only to diagnose disease, but also to follow the severity of myositis disease activity.

Such methods of detecting anti-isoleucyl-tRNA synthetase antibodies can include biochemical assays. For instance, a sample (e.g., serum) obtained from a patient can be tested for an inhibitory effect on isolated, recombinant human isoleucyl-tRNA synthetase in a suitable assay, (e.g., aminoacylation assay, assay for aminoacyladenylate formation).

Such methods of detecting and monitoring disease can also include immunological methods such as immunodiffusion, enzyme-linked immunosorbent assay (ELISA), radioimmunoassay (RIA), Western blot, counter-immunoelectrophoresis, various antibody capture assays, immunodiffusion, particularly Ouchterlony double immunodiffusion, or various combinations of these methods and detection systems (See, e.g., for standard methods: *Antibodies: A Laboratory Manual* Harlow, E. and Lane, D., Cold Spring Harbor Laboratory Press, Cold Spring Harbor, N.Y., 1988).

For example, an antibody capture assay involves binding purified or partially purified IleRS protein directly to a solid substrate, such as a microtiter plate. Alternatively, the IleRS protein can be bound to the solid substrate indirectly, for example through antibodies that have been made specifically to IleRS, in a two-antibody assay. Sites on the bound IleRS protein that bind other proteins nonspecifically are saturated using a blocking buffer, typically containing bovine serum albumin. Excess blocking buffer is removed by one or more washing steps. The sample (e.g., serum) or dilution thereof to be tested for the presence of anti-IleRS antibodies is added and maintained under conditions suitable for binding to the IleRS protein. Unbound antibodies and other components of the serum are removed by one or more washes. Bound antibodies can be detected using a variety of methods. For example, a labeled secondary reagent, such as enzymatically labeled or radioactively labeled anti-immunoglobulin antibodies or protein A can be used to detect bound antibody. Excess labeled secondary reagent is removed by one or more washes.

An ELISA method can be used to screen the sera of patients having symptoms of autoimmune and/or neuromuscular disease for the presence of antibodies to human isoleucyl-tRNA synthetase (see Biswas, T. et al., *J. Immunol. Methods* 98:243–248 (1987) for an example of a method to detect anti-Jo-1 antibodies to human histidyl-tRNA synthetase). For the ELISA, recombinant human isoleucyl-tRNA synthetase can be isolated and purifed from host cells. The purified enzyme can be used to coat microtiter plates, and goat serum can be added to block non-specific binding sites on the enzyme. Diluted patient serum can then be added to the wells. Dilute peroxidase-conjugated goat IgG F(ab')$_2$ antihuman IgG, and in a subsequent step, peroxidase substrate can be added to the wells to enable quantitation of bound antibody by reading the light absorbance at 492 nm.

The isolation of human isoleucyl-tRNA synthetase genes makes possible the production of relatively large amounts of a human IleRS enzyme in pure form, compared to amounts of the enzyme that can be produced from human cells or cell lines. Co-purification of a host enzyme with the human enzyme is less likely when the human enzyme is expressed in a host organism not closely related to humans (*Pichia pastoris*, for instance, as demonstrated in examples herein). A further advantage of being able to efficiently produce the human isoleucyl-tRNA synthetase in cells constructed for the production of this foreign protein is that a radioactive label can be incorporated into the human IleRS protein during the growth of the cells in culture, facilitating various assays such as immunological assays, and the quantitation and location of the human isoleucyl-tRNA synthetase.

Antibodies

The invention further relates to antibodies that bind to an isolated and/or recombinant human isoleucyl-tRNA synthetase, including portions thereof (e.g., a peptide), which can specifically recognize and bind to the enzyme. These can be used in methods to purify the protein or portion thereof by various methods of immunoaffinity chromatography, or to selectively inactivate one of the enzyme's active sites, or to study other aspects of the enzyme's structure, for example. The antibodies can be used to map the antigenic determinants on a human isoleucyl-tRNA synthetase to which anti-isoleucyl tRNA synthetase autoantibodies react. They can also be used as control antibodies in assays to detect and quantitate anti-isoleucyl-tRNA synthetase antibodies present in the body fluids of patients with certain idiopathic inflammatory myopathies, such as myositis, polymyositis and dermatomyositis. The antibodies may also be useful to detect the presence of human isoleucyl-tRNA synthetase in serum or other tissue samples, as a measure of cell damage.

The antibodies of the present invention can be polyclonal or monoclonal, and the term antibody is intended to encompass both polyclonal (e.g., raised in a suitable animal other than a human) and monoclonal antibodies. Antibodies of the present invention can be raised against an appropriate immunogen, including proteins or polypeptides of the present invention, such as an isolated and/or recombinant human isoleucyl-tRNA synthetase or a portion thereof, or synthetic molecules, such as synthetic peptides.

The term antibody is also intended to encompass single chain antibodies, chimeric, humanized or primatized (CDR-grafted) antibodies, as well as chimeric or CDR-grafted single chain antibodies, comprising portions derived from more than one species. The various portions of these antibodies can be joined together chemically by conventional techniques, or can be prepared as a contiguous protein using genetic engineering techniques. For example, nucleic acids encoding a chimeric or humanized chain can be expressed to produce a contiguous protein. See, e.g., Cabilly et al., U.S. Pat. No. 4,816,567; Cabilly et al., European Patent No. 0,125,023 B1; Boss et al., U.S. Pat. No. 4,816,397; Boss et al., European Patent No. 0,120,694 B1; Neuberger, M. S. et al., WO 86/01533; Neuberger, M. S. et al., European Patent No. 0,194,276 B1; Winter, U.S. Pat. No. 5,225,539; and Winter, European Patent No. 0,239,400 B1. See also, Newman, R. et al., *BioTechnology*, 10: 1455–1460 (1992), regarding primatized antibody, and Ladner et al., U.S. Pat. No. 4,946,778 and Bird, R. E. et al., *Science*, 242:423–426 (1988)) regarding single chain antibodies.

In addition, functional fragments of antibodies, including fragments of chimeric, humanized, primatized or single chain antibodies, can also be produced. Functional fragments of the foregoing antibodies retain at least one binding function and/or modulation function of the full-length antibody from which they are derived. For example, antibody fragments capable of binding to human isoleucyl-tRNA synthetase or a portion thereof, including, but not limited to, Fv, Fab, Fab' and F(ab')$_2$ fragments are encompassed by the invention. Such fragments can be produced, for example, by enzymatic cleavage or by recombinant techniques. For instance, papain or pepsin cleavage can generate Fab or F(ab')$_2$ fragments, respectively. Alternatively, antibodies can be produced in a variety of truncated forms using antibody genes in which one or more stop codons have been introduced upstream of the natural stop site. For example, a chimeric gene encoding an F(ab')$_2$ heavy chain portion can be designed to include DNA sequences encoding the CH$_1$ domain and hinge region of the heavy chain.

Preparation of immunizing antigen, and polyclonal and monoclonal antibody production can be performed using any suitable technique. A variety of methods have been described (see e.g., Kohler et al., *Nature*, 256: 495–497 (1975) and *Eur. J. Immunol.* 6: 511–519 (1976); Milstein et al., *Nature* 266: 550–552 (1977); Koprowski et al., U.S. Pat. No. 4,172,124; Harlow, E. and D. Lane, 1988, *Antibodies: A Laboratory Manual*, (Cold Spring Harbor Laboratory: Cold Spring Harbor, N.Y.); *Current Protocols In Molecular Biology*, Vol. 2 (Supplement 27, Summer '94), Ausubel, F. M. et al., Eds., (John Wiley & Sons: New York, N.Y.), Chapter 11, (1991)). Generally, a hybridoma is produced by fusing a suitable immortal cell line (e.g., a myeloma cell line such as SP2/0) with antibody producing cells. The antibody producing cell, preferably obtained from the spleen or lymph nodes, are obtained from animals immunized with the antigen of interest. The fused cells (hybridomas) are isolated using selective culture conditions, and cloned by limiting dilution. Cells which produce antibodies with the desired specificity are selected by a suitable assay (e.g., ELISA).

Assays for Inhibitors and Tester Strains

The enzymatic assays, binding assays, and construction of tester strains described below, can be used, alone or in combination with each other or other suitable methods, to identify inhibitors of one or more aminoacyl-tRNA synthetases of an organism of interest, such as a pathogenic organism. Such inhibitors can be tested further for the specific inhibition of a particular aminoacyl-tRNA synthetase of a particular pathogen. The inhibitors can be further tested for their possible effects on a specific aminoacyl-tRNA synthetase of humans or of other animals in which the inhibitor might be used as an antimicrobial agent.

Pathogenic organisms are characterized by their ability to cause an undesired infection in a human or animal, and are not limited to those organisms known to cause a characterized or named disease or condition. Pathogens include, for example, *Mycobacterium tuberculosis*, *Pneumocystis carinii*, *Candida albicans*, *Staphylococcus aureus*, and *Helicobacter pylori*.

Enzyme Assay

Because the amino acid sequences of the tRNA synthetases have diverged over evolution, significant differences exist between the structure of the enzymes from mammals (e.g., human, bovine) and from mammalian pathogens. The design of inhibitors can exploit the structural differences between the pathogen aaRS and the host (e.g., a mammalian host, such a human) aaRS to yield specific inhibitors, which may further have antimicrobial activity.

Upon the isolation of an IleRS gene from a pathogenic organism, the gene can be incorporated into an expression system for production of the IleRS or a fusion protein comprising an IleRS, followed by isolation and testing of the enzyme in vitro. Information from assays and structural studies of a purified human enzyme, combined with information from assays and structural studies of the corresponding (i.e., specific for the same amino acid) pathogen enzyme intended as the target of an inhibitor, can be used to model inhibitors of one or more pathogen enzymes that minimally affect the corresponding human enzyme(s). In tests for toxicity, the isolated aminoacyl-tRNA synthetases of the intended host or of a related species can be assessed for any effect the inhibitors might specifically have on them. An isolated, recombinant human isoleucyl-tRNA synthetase can be tested for the effects of an inhibitor using methods that parallel those methods used to test an isolated isoleucyl-tRNA synthetase or other aminoacyl-tRNA synthetase of a pathogen.

Isolated, active IleRSs of pathogens can be used in an in vitro method of screening for inhibitors of isoleucyl-tRNA synthetase activity in which the inhibitory effect of a compound is assessed by monitoring IleRS activity according to standard techniques. For example, inhibitors of the activity of isolated, recombinant *M. tuberculosis* IleRS can be identified by the method, and these inhibitors of *M. tuberculosis* IleRS can be also tested for an inhibitory effect upon a human IleRS according to a similar method.

In one embodiment, the isolated IleRS enzyme is maintained under conditions suitable for isoleucyl-adenylate formation, the enzyme is contacted with a compound to be tested, and formation of isoleucyl-adenylate is monitored by standard assay. A reduction in the activity measured in the presence of compound, as compared with the activity in the absence of compound, is indicative of inhibition of isoleucyl-tRNA synthetase activity by the compound.

For example, the extent of isoleucyl-adenylate formation catalyzed by purified IleRS can be measured using an ATP-pyrophosphate exchange assay in the presence and in the absence of a candidate inhibitor (Calendar, R. and P. Berg, *Biochemistry*, 5:1690–1695 (1966)). In this reaction, the enzymatic synthesis of ATP from AMP and pyrophosphate in the absence of tRNA is monitored. A candidate inhibitor can be added to a suitable reaction mixture (e.g., 100 mM TrisCl, pH 7.5/5 mM $MgCl_2$/10 mM 2-mercaptoethanol/10 mM KF/2 mM ATP/2 mM $[^{32}P]$-pyrophosphate/1 mM isoleucine), and the mixture is incubated at 25° C. IleRS (to a final concentration of ~10 nM) is added to initiate the reaction. Aliquots of the reaction are removed at various times and quenched in 7% (vol/vol) cold perchloric acid, followed by the addition of 3% (wt/vol) charcoal suspended in 0.5% HCl. The ATP adsorbed to charcoal is filtered onto glass fiber pads (Schleicher & Schuell), and formation of $[^{32}P]$-ATP is quantified by liquid scintillation counting in Hydrofluor (National Diagnostics, Manville, N.J.). The enzyme activity measured in the presence of the compound is compared with the activity in the absence of the compound to assess inhibition.

Alternatively, a candidate inhibitor can be preincubated with enzyme under suitable conditions. Preincubation in the absence of substrate provides a more sensitive assay for the detection of inhibition (e.g., detects slow binding inhibitors). For example, the compound can be added to a mixture containing ~10 nM isoleucyl-tRNA synthetase in 100 mM TrisCl, pH 7.5/5 mM $MgCl_2$/10 mM 2-mercaptoethanol/10 mM KF, and preincubated at 25° C. for 20 minutes. To initiate the reaction, ATP, $[^{32}P]$-pyrophosphate and isoleucine are added to final concentrations of 2 mM, 2 mM and 1 mM, respectively. The reaction is monitored as described above, and the activity measured in the presence of compound is compared with the activity in the absence of compound to assess inhibition.

In another embodiment, formation of the aminoacylated tRNA is monitored in a standard aminoacylation assay. Inhibitors identified by enzymatic assay can be further assessed for antimicrobial activity using tester strains as described herein, or using other suitable assays. For example, the extent of aminoacylation of tRNA with isoleucine catalyzed by IleRS (e.g., a GST fusion) can be measured by monitoring the incorporation of $[^3H]$-isoleucine into trichloroacetic acid-precipitable $[^3H]$-isoleucyl-tRNA in the presence of a candidate inhibitor, as compared with activity in the absence inhibitor. Appropriately diluted IleRS (~0.4 nM) can be preincubated for 20 minutes at 25° C. in, for example, 50 mM HEPES, pH 7.5/0.1 mg/ml BSA (bovine serum albumin)/10 mM $MgCl_2$/10 mM 2-mercaptoethanol/20 mM KCl/1–20% DMSO (preferably about 1%) in the presence or absence of a compound to be tested. The preincubation mixture can be supplemented with ATP, $[^3H]$-isoleucine and tRNA to final concentrations of, for example, 4 mM ATP/20 µM $[^3H]$-isoleucine (0.6 µCi), and 90 µM crude or 2 µM specific $tRNA^{Ile}$. The reaction can be maintained at 25° C., and aliquots are removed at specific times, and applied to filter paper discs (3 MM, Whatman) that have been presoaked with 5% (wt/vol) trichloroacetic acid. Filters are washed for three 10-minute periods in 5% trichloroacetic acid, rinsed in 95% ethanol and 100% ether, and the incorporation of $[^3H]$-isoleucine into tRNA (formation of $[^3H]$-Ile-tRNA) is measured in Betafluor by liquid scintillation counting. The aminoacylation assay can also be performed without preincubation under suitable conditions (e.g., using ~0.4 nM IleRS in a reaction mixture containing 50 mM HEPES, pH 7.5/0.1 mg/ml BSA (bovine serum albumin)/10 mM $MgCl_2$/10 mM 2-mercaptoethanol/20 mM KCl/1–20% DMSO/4 mM ATP/20 µM $[^3H]$-isoleucine (0.6 µCi), and 90 µM crude or 2 µM specific $tRNA^{Ile}$) in the presence or absence of test compound. An $IC_{50}$ value (the concentration of inhibitor causing 50% inhibition of enzyme activity) for a known amount of active IleRS can be determined.

Tester Strains

A substance to be used as a therapeutic agent preferably inhibits a pathogen aaRS without significantly inhibiting the corresponding aaRS of its host, e.g., a human or animal. Nucleic acids of the present invention can be used in constructing tester strains for in vivo assays of the effect on the activity of the pathogen enzyme of a substance which is added to tester strain cells. Complementation of a particular defective host cell aaRS gene by an aaRS gene of origin in a different species from the host cell aaRS gene is a threshold requirement for a tester strain.

A first type of tester strain comprises a host cell having a defect in an endogenous gene encoding an aaRS, and a heterologous pathogen aaRS gene which complements the defect in the host cell gene.

A second type of tester strain serves as a control for the first type of tester strain. This second type of tester strain also comprises a host cell having a defect in an endogenous gene encoding an aaRS, and also carries a heterologous gene encoding an aaRS, wherein the heterologous gene complements the defect in the host cell gene. However, in this case, the heterologous gene has its origin in a human or other animal, for example an animal that can be infected by the pathogen whose aaRS is tested in the first type of tester strain. Alternatively, the heterologous gene can be from a different animal species whose aaRS is closely related in structure to the aaRS of the susceptible animal (or human). This second type of tester strain allows the assessment of an inhibitory or toxic effect of a substance administered to the tester strain cells, due specifically to the interaction of the substance with the heterologous aaRS.

Because the aaRS genes are essential, the heterologous gene can be introduced into the host cell simultaneously with inactivation of the host cell gene to preserve viability.

Alternatively, the heterologous gene can be introduced into the host cell before inactivation or loss of the host cell gene. In this case, to test for complementation, the host cell is then subjected to some change in conditions (e.g., a change in temperature, growth medium, selection conditions) which causes inactivation or loss of either the host aaRS gene or gene product, or both.

Temperature sensitive alleles are examples of genes encoding conditionally inactivatable tRNA synthetases. For example, temperature-sensitive alleles of the genes encoding cytoplasmic IleRS (ils1-1) and MetRS (mes1-1) have been described in *S. cerevisiae* (Hartwell, L. H., and McLaughlin, C. S., *J. Bacteriol.* 96:1664–1671 (1968); McLaughlin, C. S., and Hartwell, L. H. *Genetics* 61:557–566 (1969)), and are available from the Yeast Genetic Stock Center (University of California-Berkeley; catalog nos. 341 and 19:3:4, respectively). Temperature sensitive strains of *E. coli* having a defect in the tyrs gene encoding TyrRS (see, e.g., Bedouelle, H. and G. Winter, *Nature* 320:371–373 (1986)); and temperature-sensitive serS strains of *E. coli* have also been described (Low, B., et al., *J. Bacteriol.* 108:742–750 (1971); Clarke, S. J. et al., *J. Bacteriol.* 113:1096–1103 (1973)).

The gene (ILS1) encoding the cytoplasmic isoleucyl-tRNA synthetase of *S. cerevisiae* has been cloned into a shuttle vector and sequenced (Englisch, U., et al., *Biol. Chem. Hoppe-Seyler* 368:971–979 (1987)). The gene encoding isoleucyl-tRNA synthetase in *E. coli* has also been isolated and characterized (Webster, T. et al., *Science* 226:1315–1317 (1984)). (For additional cloned and sequenced isoleucyl-tRNA synthetases, see Meinnel, T. et al., "Aminoacyl-tRNA Synthetases: Occurrence, Structure and Function," Chapter 14, pp. 251–292. In *tRNA: Structure, Biosynthesis and Function*, S611, D. and U. RajBhandary, Eds., (American Society for Microbiology, Washington, D.C., 1995), the teachings of which are incorporated herein by reference.)

If the heterologous gene complements the inactivated host cell gene, such a cell can be used in a test of whether a substance can interact specifically with the pathogen tRNA synthetase (or a component in the pathway of tRNA synthetase gene expression) introduced for testing, to cause loss of function of the tested pathogen tRNA synthetase in those host cells. Thus, such cells are "tester strains." Successful cross-species complementation has been described already, for example, for yeast seryl-tRNA synthetase and for yeast isoleucyl-tRNA synthetase in *E. coli* (Weygand-Durasevic, I., et al., *Eur. J. Biochem* 214:869–877 (1993); Racher, K. I., et al., *J. Biol. Chem.* 266:17158–17164 (1991)). Cross-species complementation within the genus of the pathogen can also serve as the basis for testing in some cases.

In tester cells to be used in an assay for chemical substances that can inhibit the function of a specific aaRS, the gene for the aminoacyl-tRNA synthetase can, for example, physically replace the host cell aaRS gene or can be present in addition to a host aaRS gene that does not produce a functional product, and the heterologous gene whose gene product is to be tested complements the host gene. A substance to be tested is administered to the tester cells, and the viability or growth of such cells can be compared with that of cells of a suitable control.

As a tester strain can comprise a host cell comprising a heterologous aaRS gene (that is, one from a heterologous or foreign species, specifically from a pathogen in the case of the first type of tester strain, and from a human or animal typically infected by the pathogen, in the case of the second type of tester strain), a suitable host cell is heterologous with respect to the species from which the gene to be tested is isolated. It will be understood that similar methods of strain construction can be used to produce a first type of tester strain (for specifically testing the sensitivity of a pathogen aaRS to a potential inhibitor of the aaRS activity) and to produce a second type of tester strain (for use as a control to evaluate the potential inhibitor of the pathogen aaRS for its specific effect on the corresponding human or animal aaRS of similar aminoacylation activity).

Species which are suitable for use as hosts for the construction of tester strains are *E. coli, S. cerevisiae*, and *B. subtilis*, for example. These species are especially amenable to genetic manipulation because of their history of extensive study.

Suitable host cells having a genotype useful for the construction of a tester strain can be constructed or selected using known methods. For example, both in *E. coli* and in *S. cerevisiae*, a first plasmid which contains a functional copy of a host chromosomal aaRS gene which is to be inactivated later, along with some selectable marker gene, can be constructed and introduced into cells. Then, an inactivating mutation can be caused in the chromosomal copy of the aaRS gene. One way to do this is by causing or selecting for a double crossover event which creates a deletion and insertion. This can be done by introducing into the cells double-stranded DNA having regions of homology to the DNA flanking the target aaRS gene, and having between these regions a gene encoding a selectable marker, either on a suitable vector or as a DNA fragment, as appropriate (Jasin et al., U.S. Pat. 4,713,337; Schimmel, P., U.S. Pat. No. 4,963,487; Toth, M. J. and Schimmel, P., *J. Biol. Chem.* 261(15):6643–6646 (1986); Rothstein, R., *Methods in Enzymology* 194:281–301 (1991)). Such an approach simultaneously inserts a selectable marker and results in a deletion of the endogenous gene between the flanking sequences provided. Where needed to maintain viability, a compatible maintenance plasmid is provided encoding an endogenous or complementing aaRS. A test plasmid which is compatible with the maintenance plasmid, and which contains the aaRS gene to be tested for complementation, can be introduced into the host cells. If the first plasmid has been constructed to have a mechanism to allow for inhibition of its replication (for example, a temperature sensitive replicon) or to have a mechanism by which cells containing the first plasmid can be selected against (by, for example, the use of 5-fluoroorotic acid (5-FOA) to select against *S. cerevisiae* cells which have a first plasmid containing the URA3 gene), cells which survive by virtue of having a complementing aaRS gene on the second plasmid can be selected (Sikorsky, R. S. and Boeke, J. D., *Methods in Enzymology* 194:302–318 (1991)).

A number of *E. coli* strains already exist in which an aaRS gene has been inactivated by some method, in whole or in part, yielding an observable phenotypic defect which can be detectably complemented by a cloned aaRS gene. For example, null strains in which the gene encoding MetRS has been inactivated, and a mutant strain of *E. coli* in which the gene encoding MetRS has been conditionally inactivated, have been described (see Kim, et al., *Proc. Natl. Acad. Sci. USA* 90:10046–10050 (1993), describing a metG null strain of *E. coli* carrying a maintenance plasmid, MN9261/pRMS615); and Barker, D. G. et al. *Eur. J. Biochem.* 127:449–457 (1982) and Starzyk, R. M. et al., *Biochemistry*, 28:8479–8484 (1989), regarding a mutant strain having a methionine auxotrophy because the $K_m$ for methionine of the enzyme encoded by the chromosomal metG allele is elevated). A null strain in which the gene encoding AlaRS has been inactivated has been described (see Jasin, M. et al., *Cell* 36:1089–1095 (1984), for an alas null strain of *E. coli* bearing a maintenance plasmid with alaS).

As particular examples of strains for testing IleRS genes for complementation, a null strain in which the gene encoding IleRS has been inactivated by deletion and insertion of a selectable marker, and a mutant strain designated MI1 in which the gene encoding IleRS has been conditionally inactivated by a point mutation, have been described (Shiba, K. and Schimmel, P., *Proc. Natl. Acad. Sci. USA*, 89:1880–1884 (1992); Shepard, A., et al, *Proc. Natl. Acad. Sci. USA*, 89:9964–9968 (1992); and Shiba, K. and P. Schimmel, *J. Biol. Chem.*, 267:22703–22706 (1992), each describing ΔileS203::kan *E. coli* strains; see also Iaccarino, M. and Berg, P., *J. Bacteriol.* 105:527–537 (1971) and Schmidt, E. and Schimmel, P. *Science* 264:265–267 (1994), each describing *E. coli* strain MI1 having an isoleucine auxotrophy due to an elevated $K_m$ for isoleucine of IleRS encoded by the IleS gene).

Causing or selecting for a double crossover event which creates a deletion and insertion can be used in itself as a one-step method of constructing a tester strain in which an endogenous aaRS gene is replaced by the corresponding gene whose gene product is to be tested. Endogenous recombination mechanisms have been used to advantage previously in *E. coli*, *B. subtilis*, and *S. cerevisiae*, among other organisms. This method depends on the ability of the heterologous (i.e., pathogen or human, for example) gene to be tested, to complement the endogenous corresponding aaRS gene. This can be done by introducing into the cells double-stranded DNA having regions of homology to the DNA flanking the target endogenous aaRS gene, and having between these regions a gene encoding a selectable marker as well as the heterologous aaRS gene intended to replace the native aaRS gene. The survival of cells expressing the selectable marker is indicative of expression of the introduced heterologous aaRS gene and complementation of the defect in the endogenous synthetase.

For example, a tester strain, useful for testing the effect of a compound on the function of IleRS expressed by an inserted heterologous gene, can be constructed in a one-step method. Optional positive and negative controls for this cross-species transformation can be used to show that the resulting strain depends on the IleRS gene from the heterologous source for growth and that this recombination event is not lethal. For example, *B. subtilis* cells made competent for transformation (Dubnau, D. and Davidoff-Abelson, R., *J. Mol. Biol.* 56:206–221 (1971)) can be transformed with a suitable construct,such as a linearized plasmid containing an insert. Generally, the construct includes a selectable marker gene for antibiotic resistance, or some other suitable selectable marker. In one embodiment, a linearized plasmid which contains the heterologous IleRS gene and an antibiotic resistance gene, situated between sequences homologous to the flanking sequences of the endogenous IleRS gene of the host cells, is used to transform the host cell. For a positive control, the linearized plasmid can be constructed in a similar fashion, except that the native *B. subtilis* IleRS gene replaces the heterologous gene, such that a normal *B. subtilis* IleRS gene is located adjacent to the antibiotic resistance marker in the insert. As a negative control, the insert can be designed to contain only the flanking sequences and the antibiotic resistance marker, for example. Antibiotic resistant transformants are not expected upon transformation with the negative control construct, as homologous recombination with the construct results in deletion of the endogenous IleRS gene. Successful construction of a tester strain can also be confirmed by Southern analysis.

The yeast *S. cerevisiae* offers additional possibilities for genetic manipulations to create tester strains, relative to bacteria. For example, one-step gene disruptions can be performed in diploid cells using a yeast integrating plasmid or DNA fragment comprising a copy of an aaRS gene containing an insertion of a selectable marker in the aaRS gene. Optionally, a fragment comprising a copy of an aaRS gene containing a deletion and an insertion of a selectable marker can be constructed. A suitable fragment can be introduced into a diploid cell to disrupt a chromosomal copy of the yeast gene. Successful integration of the disrupted aaRS gene can be confirmed by Southern blotting and by tetrad analysis of the sporulated diploid cells. The diploid cells heterozygous for the disrupted aaRS gene provide a diploid host strain which can be transformed with a plasmid containing the heterologous aaRS gene. These cells can be sporulated and the haploid spores analyzed for rescue of the defective chromosomal aaRS by the heterologous aaRS gene.

Alternatively, those diploid cells that are found to contain one copy of the disrupted chromosomal aaRS gene, as well as one functional copy, can be transformed with a maintenance plasmid which contains a gene which complements the disruption, such as the corresponding wild type yeast aaRS gene, and which also provides for a mechanism to select against survival of the cells containing this plasmid. These cells can then be made to sporulate to obtain a haploid null strain containing the disrupted chromosomal aaRS gene and the wild type gene on the maintenance plasmid. This haploid host strain can then be transformed with a test plasmid which expresses a heterologous aaRS gene, and the maintenance plasmid can be selected against by growing this strain under appropriate conditions.

To construct a maintenance plasmid or a test plasmid carrying a heterologous gene, a suitable vector, such as a yeast centromere plasmid (CEN; single-copy) or 2μ vector (high copy) can be used. A heterologous gene to be tested can also be incorporated into the chromosome, using an integrating plasmid, for example, which lacks a yeast origin of replication. Examples of convenient yeast vectors for cloning include vectors such as those in the pRS series (integrating, CEN, or 2μ plasmids differing in the selectable marker (HIS3, TRP1, LEU2, URA3); see Christianson, T.W., et al., *Gene*, 110:119–122 (1992) regarding 2μ vectors; see Sikorski, R. S. and Hieter, P. *Genetics*, 122:19–27 (1989) regarding integrating and CEN plasmids which are available from Stratagene, La Jolla) and shuttle vectors (integrating, CEN or 2μ vectors) which contain the multiple cloning site of pUC19 (Gietz, R. D. and Sugino, A., *Gene*, 74:527–534 (1988)). Examples of expression vectors include pEG (Mitchell, D. A. et al., *Yeast*, 9:715–723 (1993)) and pDAD1 and pDAD2, which contain a GAL1 promoter (Davis, L. I. and Fink, G. R., *Cell* 61:965–978 (1990)).

A variety of promoters are suitable for expression. Available yeast vectors offer a choice of promoters. In one embodiment, the inducible GAL1 promoter is used. In another embodiment, the constitutive ADH1 promoter (alcohol dehyrogenase; Bennetzen, J. L. and Hall, B. D., *J. Biol. Chem.*, 257:3026–3031 (1982)) can be used to express an inserted gene on glucose-containing media. For example plasmid pMC4 carries the ADH (alcohol dehydrogenase) promoter of *S. cerevisiae* and the coding sequence for cytochrome oxidase IV targeting signal peptide, downstream from the promoter (Hurt, E. C. et al., *J. Biol. Chem.* 262:1420–1424 (1987)). Derivatives of plasmid pMC4 can be made which lack the coding sequence for the targeting signal peptide (that directs proteins for import into mitochondria) downstream from the ADH promoter. Such derivatives of plasmid pMC4 allow a coding sequence inserted downstream from the ADH promoter to cause the biosynthesis of a protein directed to the cytoplasm (unless the inserted coding sequence carries its own mitochondrial targeting signal). These derivatives can be engineered by cloning fragments derived from pMC4 into the vectors listed above, for example.

In another embodiment, a eucaryotic host cell is used to construct a mitochondrial tester strain. For example, in yeast, each of the mitochondrial tRNA synthetases is essential for growth on non-fermentable carbon sources (e.g., glycerol). Thus, complementation tests can be conducted in mitochondrial tester strains. As the genes encoding mitochondrial aminoacyl-tRNA synthetases are typically nuclear-encoded, the procedures described above can be modified to construct mitochondrial tester strains having a defect in a mitochondrial aminoacyl-tRNA synthetase. Modification is necessitated by the fact that yeast strains with a defect in mitochondrial protein synthesis, such as a defective aminoacyl-tRNA synthetase, lose their mitochondrial DNA, rapidly becoming rho-. As a result, these strains are unable to grow on non-fermentable carbon sources even if a complementing gene is introduced into the strain. Therefore, a haploid strain having a defect in, for example, the yeast mitochondrial isoleucyl-tRNA synthetase gene (e.g., a gene disruption with a cosegregating selectable marker constructed as indicated above) can be crossed with a rho$^+$ strain having a wild-type mitochondrial isoleucyl-tRNA synthetase gene to restore the mitochondrial DNA. The resulting rho$^+$ diploid can then be transformed with a plasmid which encodes the wild-type yeast mitochondrial isoleucyl-tRNA synthetase (i.e., a maintenance plasmid) and a second selectable marker. Following sporulation, progeny spores which carry the defective mitochondrial IleRS, identified by the presence of the cosegregating selectable marker, and the maintenance plasmid, identified by the presence of the second selectable marker, and which are rho$^+$, can be isolated (e.g., by tetrad analysis). Strains constructed in this manner would be suitable for complementation assays using heterologous aminoacyl-tRNA synthetase genes.

For instance, a plasmid encoding a heterologous isoleucyl-tRNA synthetase gene can be introduced into such a yeast strain on a second plasmid having a third selectable marker. As indicated above, the maintenance plasmid can be selected against (e.g., where the selectable marker is URA3, selection on growth medium containing 5-fluoroorotic acid leads to loss of the maintenance plasmid), and complementation by the heterologous gene can be monitored on a non-fermentable carbon source.

In another embodiment of tester strain construction, a mitochondrial isoleucyl-tRNA synthetase gene disruption with a cosegregating selectable marker can be constructed in a diploid rho$^+$ strain (see e.g., Edwards, H. and P. Schimmel, Cell 51:643–649 (1987) for an example of a mitochondrial tyrosyl-tRNA synthetase gene disruption). A plasmid encoding a heterologous isoleucyl-tRNA synthetase gene can be introduced on a plasmid having a second selectable marker. Sporulation of a resulting diploid yields two progeny spores carrying the yeast mitochondrial isoleucyl-tRNA synthetase gene disruption, identified by the presence of a cosegregating selectable marker, and two progeny spores carrying the corresponding wild-type gene. The presence of the plasmid can be monitored by the presence of the second selectable marker. Complementation by the heterologous gene on the introduced plasmid is indicated by growth on non-fermentable carbon sources of cells carrying the disrupted isoleucyl-tRNA synthetase gene.

In the case of a mitochondrial tester strain, a heterologous aminoacyl-tRNA synthetase can be imported into mitochondria to achieve complementation of the mitochondrial defect. When it is necessary to achieve import, or desirable to improve the efficiency of import of an aminoacyl-tRNA synthetase in the host cell, a gene fusion can be constructed using a sequence encoding a mitochondrial targeting sequence which functions in the host cell. For example, a mitochondrial targeting sequence can be introduced at the amino-terminal end of the heterologous aminoacyl-tRNA synthetase by an appropriate gene fusion. In one embodiment in yeast, the heterologous aaRS gene or a sufficient portion thereof is introduced into a vector in which it is placed under the control of the minimal alcohol dehydrogenase promoter and is fused to the yeast cytochrome oxidase IV targeting signal derived from plasmid pMC4 (Bibus et al., *J. Biol. Chem.*, 263:13097 (1988)). Expression of the construct yields a fusion protein with an N-terminally located cytochrome oxidase IV targeting signal joined to the aaRS protein of the heterologous organism.

If the construction methods described here are not successful initially, one or more natural or synthetic tRNA gene(s) of an organism other than the host cell (e.g., procaryotic, such as a bacterial, or eucaryotic, such as a mammalian or fungal) can be introduced into the host cell to provide one or more cognate tRNAs for the pathogen aaRS (or, the case of the second type of tester strain, for the human or animal aaRS). The tRNA genes of many species have been cloned and sequenced (Steinberg, S., et al. "Compilation of tRNA sequences and sequences of tRNA genes", *Nucleic Acids Res.* 21:3011–3015 (1993)). A method for constructing a strain of *Streptomyces lividans* in which an essential tRNA gene has been inactivated in the chromosome, and the gene is instead maintained on a plasmid, has been described (Cohen, S. N., WO 94/08033 (1994)).

Use of Tester Strains

Tester strains can be made to isolate the effect of a substance on a particular aaRS in vivo. The tester strains are ordinarily of two types: the first, dependent upon a heterologous aaRS gene of origin from a pathogenic microbe; the second, dependent upon a heterologous aaRS gene of origin from a host (animal or human) for a pathogenic microbe. Usually, the first type of tester strain is used to test for a desirable inhibitory effect of an antimicrobial agent upon a pathogenic aaRS. The second type of tester strain is used to test for an undesirable inhibitory effect of an antimicrobial agent, specifically upon the corresponding aaRS of a species of potential recipient of the antimicrobial agent, or of a related species. This second type of tester strain can be considered a type of control strain for the first type of tester strain (the first type is also referred to herein as a "pathogen tester" strain or cells).

To assess the inhibitory effect of a substance on a tester strain, the cells are maintained under conditions suitable for complementation of the host cell defect by the heterologous aaRS gene. These are conditons under which the tester strain depends on the function of the heterologous aaRS gene and its product (i.e., assay conditions). A substance to be tested is administered to the tester cells, and the viability or growth of the tester cells can be compared with that of cells of one or more suitable controls. A variety of control experiments can be designed to assess the inhibitory effect of a substance and/or the specificity of inhibition. The following examples are provided for purposes of illustration.

A preliminary test for inhibitory effect may be conducted where desired, using pathogen tester cells, that is, cells dependent upon the aaRS derived from a pathogenic organism. For example, a substance to be tested can be administered to pathogen tester cells maintained under assay conditions, and the viability or growth of the pathogen tester cells in the presence of the substance can be compared with that of pathogen tester cells maintained under the same conditions in the absence of the substance. If it is determined that the substance inhibits growth of the pathogen tester cells, a further assessment of the specificity of inhibition by the substance can be conducted as described below.

Alternatively, the inhibitory effect of a substance on tester cell growth and the specificity of inhibition can be determined without conducting the preliminary test for inhibitory activity. The following examples, in which the various cell types are in each case exposed to drug, are provided for purposes of illustration only.

To determine the specificity of inhibition, the viability or growth of the pathogen tester cells can be compared with that of cells of one or more suitable control strains maintained under the same conditions. In particular, tester strains and control strains are maintained under assay conditions, and exposed to the substance to be tested.

Strains which are similar to the tester strain, but lack the heterologous aminoacyl-tRNA synthetase gene present in the tester strain (i.e., the "test gene"), can serve as control strains. These control strains comprise a "control gene" which is an aminoacyl-tRNA synthetase gene other than the heterologous aaRS gene present in the tester strain (i.e., an aaRS gene from a different species, such as a procaryotic or eucaryotic species). The control gene can be a cytoplasmic or mitochondrial aaRS gene, and it encodes an aaRS specific for the same amino acid as the aaRS encoded by the test gene. Viability or growth of the control strain is dependent upon the control gene under the conditions of the assay.

In one embodiment, the strain used as a control (a second type of tester stain) can be a strain distinct from the pathogen tester strain, but is constructed in a manner which generally parallels that of the pathogen tester strain comprising the pathogen test gene, such that complementation of the host cell defect, which is also present in the control strain, is dependent upon the control gene under the assay conditions. In this embodiment, the control strain preferably comprises a host cell of the same species as the host cell used to construct the tester strain, and is closely related in genotype to the tester strain. These preferred control strains comprise a "control gene," which, as indicated above, is an aaRS gene other than the test gene (i.e., an aaRS gene from a different species, such as a heterologous procaryotic or eucaryotic species). Furthermore, the control gene, which can be cytoplasmic or mitochondrial, encodes an aaRS specific for the same amino acid (e.g., an isoleucyl-tRNA synthetase) as the test gene (e.g., an isoleucyl-tRNA synthetase).

Preferably, the control gene is selected from a species which is a host for the pathogen from which the test gene is derived, permitting the identification of specific inhibitors which selectively inhibit the pathogen aaRS (e.g., a human control gene for an *H. pylori* test gene). Alternatively, because the eucaryotic aminoacyl-tRNA synthetases are generally more closely related to each other than to procaryotic aminoacyl-tRNA synthetases, a control gene from another eucaryote (e.g., a different mammalian species) can be used in lieu of one selected from the host species (e.g., a rat or mouse control gene for a *P. carinii* test gene).

Typically, the control gene is a human gene and the second type of tester strain used as a control for the pathogen tester strain is a human tester strain. The term "human" is used below as an illustration of a second type of control strain.

For example, a strain isogenic with a pathogen tester strain except for the substitution of a human control gene, can serve as a control strain, called a human tester strain. Such a control strain can be constructed using the same methods and the same host cell used to construct the first type of tester strain, with the exception that a human control gene is introduced into the host cell in lieu of the pathogen aaRS gene present in the tester.

Under the conditions of this assay, growth or viability of the second type (e.g. human) tester strain is dependent upon the control aaRS gene, which complements the host cell aaRS defect in the second type of tester strain which is used as a control. Specific inhibition by a substance can be determined by comparing the viability or growth of the pathogen tester and second type of tester strain in the presence of the substance.

The use of a second type of tester strain as a control is particularly important for use in testing a substance intended for use as an antimicrobial agent. Where the antimicrobial agent is intended for use in humans, a human tester strain provides a method of determining the extent of any toxicity or inhibitory effect specifically caused by the interaction of the antimicrobial agent with the human aaRS. Pairs of pathogen and human tester strains constructed from the same parental strain may be particularly useful where it is desirable to test the specific effects of a substance on the in vivo activity of both the aaRSs heterologous to the parental strain, under similar conditions. An example of such a pair is a *S. cerevisiae* strain dependent upon the function of the cytoplasmic isoleucyl-tRNA synthetase of *Candida albicans* and a nearly isogenic *S. cerevisiae* strain dependent upon the function of the cytoplasmic isoleucyl-tRNA synthetase of humans.

In some cases, further controls may be desired to assess specific inhibition. For this purpose, one or more additional "comparison control" strains are used for purposes of comparison. These additional controls can be used to assess the relative effects of a substance upon growth of the tester and control strains in the presence of the substance.

Strains useful for this purpose include, for example, strains of the same species as the host cell used to construct the tester strain, which contain a wild type version of the aaRS gene which is inactivated in the tester strain. In one embodiment, where an *E. coli* host is used to construct a pathogen tester strain comprising a pathogen test gene, an *E. coli* strain comprising a wild-type *E. coli* aaRS gene can be used as a comparison control strain. In another embodiment, "parental-type" cells (e.g., parent host cells or a similar strain) are used as comparison controls. For example, the parent host cells of the first type tester strain can serve as a comparison control strain for the first type tester strain. Where the first and second types of tester strains have the same parent, a single strain can be used as the comparison control strain for both first and second types of tester strains.

For example, a parent host cell from which the pathogen tester and control (second type tester, e.g. human) strains were both constructed (e.g., by inactivation and replacement of the wild type host aaRS gene) can be used as a comparison control strain. This comparison control strain contains a wild type version of the aaRS gene which is inactivated in the tester strains, and the viability or growth of this comparison control strain is dependent upon the wild type aaRS under the conditions of the assay. Specific inhibition of the heterologous pathogen aaRS enzyme encoded by the heterologous pathogen gene (or a step in the expression of the heterologous gene) is indicated if, after administering the substance to both types of tester strains, growth of the pathogen tester strain is reduced as compared with an appropriate comparison control strain, and growth of the control (or second type tester) strain is not reduced, or is relatively less reduced, as compared with its appropriate comparison control strain.

Applications in Biochemistry

A human isoleucyl-tRNA synthetase or portions (e.g. stable subdomains) of such protein can be used in a method to separate isoleucine from a mixture of isoleucine and other compounds such as other amino acids, or to specifically isolate L-isoleucine from D-isoleucine. The isoleucyl-tRNA synthetase can be chemically attached to a solid support material packed in a column or other suitable container. Alternatively, a fusion protein such as a GST-Ile tRNA synthetase fusion can permit attachment to a suitable solid support which binds the GST (glutathione S-transferase) portion of the fusion protein. For example, a mixture of isoleucine and other compounds can be loaded onto the column under conditions in which isoleucine binds to isoleucyl-tRNA synthetase, while other compounds present in the mixture flow through the column. In a later step, isoleucine can be released from the enzyme by changing the conditions in the column, such as washing with a solution of high ionic strength to elute L-isoleucine, for example.

In a similar manner, a human isoleucyl-tRNA synthetase can be used in a method to isolate tRNA that specifically recognizes the isoleucyl-tRNA synthetase.

A human isoleucyl-tRNA synthetase can be used in the quantitative determination of isoleucine by its conversion to isoleucyl hydroxamate. An example of an appropriate assay is illustrated by the following series of reactions.

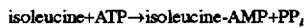

(in the presence of excess pyrophosphatase and ATP at pH 7.5, where pyrophosphatase catalyzes the conversion of the product inorganic pyrophospate ($PP_i$) to inorganic orthophospate ($P_i$); ATP is adenosine triphospate; AMP is adenosine monophosphate)

The resulting colored complex can be quantitated by spectrophotometric measurements of absorbance at 540 nm, and compared with a standard curve made using known concentrations of isoleucine. This assay is based on the reactions described by Stulberg and Novelli, *Methods in Enzymology* 5:703–707 (1962).

An isoleucyl-tRNA synthetase can also be used for the quantitative determination of ATP. In the presence of excess isoleucine, and in the presence of pyrophosphatase to convert the product $PP_i$ to $P_i$, the ATP is quantitatively converted to AMP and inorganic pyrophosphate by the isoleucyl-tRNA synthetase. For example,

$P_i$ can be quantitated by reaction with molybdate, measuring the absorbance at 580 nm and comparing to a standard curve made using known quantities of orthophosphate.

Isolation and Analysis of Human Isoleucyl tRNA Synthetase Genes

Two cloned genes of different length, both encoding a human cytoplasmic isoleucyl-tRNA synthetase, have been isolated and transformed into *E. coli*. A shortened cloned gene for human cytoplasmic isoleucyl-tRNA synthetase, when transformed into *E. col*, resulted in the production of a protein with amino acids 6-1085 of a naturally occurring enzyme in human cells. This enzyme was active in charging bovine crude tRNA with isoleucine.

The techniques used in cloning the genes encoding the human mitochondrial and cytoplasmic isoleucyl-tRNA synthetases were as follows.

Primer Design and PCR

Programs designed by the Genetics Computer Group (Madison, Wis.) were used to compare the available DNA and amino acid sequences of isoleucyl-tRNA synthetase genes to aid in choosing primers to use in making PCR fragments of the human ileRS genes. Multiple sequence alignments were performed using the PILEUP program which aligns multiple sequences based on the method of Needleman and Wunsch (*J. Mol. Biol.* 48:443–453, 1970). From the aligned sequences, the "distances" between any two selected sequences, the evolutionarily conserved residues, and the average similarity among all members at each position were calculated using the DISTANCE, the PRETTY and the PLOTSIMILARITY programs, respectively. These programs use the modified Dayhoff comparison table (Gribskov and Burgess, *Nucleic Acids Res.* 14:6745–6763 (1986)) for calculation.

One eubacterial (*E. coli*, Webster, T. A., et al., *Science* 226:1315–1317 (1984)), one archaebacterial (*Methanobacterium thermoautotrophicum*, Jenal, U., et al., *J. Biol. Chem.* 266:10570–10577 (1991)) and two lower eucaryotic (*S. cerevisiae*, Englisch, U., et al., *Biol. Chem. Hoppe-Seyler* 368:971–979 (1987); Martindale, D. W., et al., *Curr. Genet.* 15:99–106 (1989)) and *Tetrahymena thermophila* (Csank, C. and Martindale, D. W., *J. Biol. Chem.* 267:4592–4599 (1992)) isoleucyl-tRNA synthetase sequences have been reported. Multiple sequence alignment of these four sequences revealed several conserved regions. For designing PCR primers, four regions were chosen (Table 1). These regions are well conserved only in IleRS (except region 3, which is also conserved in LeuRS). Sets of degenerate primers were synthesized for these regions as shown in Table 1. In regions 1 and 3, the sequences were divided into two subgroups according to similarity and primers were designed separately for each subgroup.

TABLE 1

Strategy for design of oligonucleotide primers

| Amino Acid Sequence | SEQ ID NO: | Primer | SEQ ID NO: | Oligonucleotide Sequence |
|---|---|---|---|---|
| Region 1 | | | | |
| GWDTHG(Lv)P | 6 | KY-16 | 7 | GGITGGGAYACICAYGGISTICC |
| GWDCHGLP | 8 | KY-17 | 9 | GGITGGGAYTGYCAYGGICTICC |
| Region 2 | | | | |
| (FY)(Mi)ES(Tvc)WW(VA)(FL)KQ | 10 | KY-37 | 11 | TWYATGGARTCIACITGGTGGGYIT TIAARCA |
| Region 3 | | | | |
| RQR(Yt)WG(IV)P(IM) | 12 | KY-18 | 13 | CGICARCGITAYTGGGGIRTICCIAT |
| R(Ns)R(YF)WG(Tn)P(IL) | 14 | KY-19 | 15 | CGIAAYCGITWYTGGGGIACICCIMT |
| Region 4 | | | | |
| EG(ILsh)DQ(Th)RGWF | 16 | KY-20 | 17 | RAACCAICCICGIGTYTGRICIWWI CCYTC |

The one letter code for amino acids is used to give the amino acid sequence of four regions that are well conserved among *E. coli* (Webster, T.A., et al., Science 226:1315–1317 (1984)), *M. thermoautotrophicum* (Jenal, U., et al., J. Biol. Chem. 266:10570–10577 (1991)), *S. cerevisiae* (Englisch, U., et al., Biol. Chem. Hoppe-Seyler 368:971–979 (1987) and Martindale, D.W., et al., Curr. Genet. 15:99–106 (1989)), and *T. thermophila* (Csank, C., et al., J. Biol. Chem. 267:4592–4599 (1992)) and *T. thermophilus* isoleucyl-tRNA synthetases. Parentheses represent amino acid residue variations at the given position and lower case letters represent the amino acid residues whose coding sequence would not be detected by a corresponding degenerate primer.
For the oligonucleotide sequence,
S = C or G;
M = A or C;
Y = C or T;
R = A or G;
W = A or T;
I = inosine.
Primers KY-16, 17 and 20 have an additional GCGAATTC at the 5' end for cloning into the EcoRI site of a vector.
Primers KY-18 and KY-19 have an additional GCGATT at the 5' end.

Using these primers, segments of DNA were amplified by PCR, using human CDNA as template (Example 1). Primer KY-17 in combination with primer KY-20, and primer KY-37 in combination with primer KY-20, yielded amplified DNA fragments from the human CDNA. Sequence analysis showed that the two amplified fragments are distinct though they have high sequence similarity to other IleRSs. The former fragment was designated type A, and the latter type B.

cDNA Cloning and Sequencing

Using the type A and type B DNA fragments as probes, the corresponding cDNAS were isolated from a human T-cell cDNA library (Example 2). One clone containing a 3.2 kb insert was obtained from the type A probe and one clone containing a 4.3 kb insert was obtained using the type B probe. The 5' portions of both type A and type B cDNAs were each extended by 232 base pairs using modified RACE PCR (Dumas, J. B., et al., Nucleic Acids Res. 19:5227–5232 (1991)). DNA sequences of these clones were determined (Example 3).

The computer program PILEUP was used to align the amino acid sequences of IleRSs from several different species for comparison with the amino acid sequences of the type A and type B gene products. The species used in this comparison with type A and type B were *Saccharomyces cerevisiae*, *Tetrahymena thermophila*, *Methanobacterium thermoautotrophicum*, *Escherichia coli*, *Pseudomonas fluorescens* and *Enterobacter aerogenes*. Chemically and/or evolutionarily related residues were calculated by the PRETTY program with Dayhoff's relatedness odds matrix (Gribskov and Burgess, Nucleic Acids Res. 14:6745, 1986).

From this alignment, the first Met residue of the type B gene product was numbered +1. This ATG in the type B gene is preceded by an in-frame termination codon. For the type A gene product, the Ser residue that is aligned with the initiation codon of *E. coli* IleRS was numbered +1.

Both type A and type B gene products share sequence similarity to IleRSs from other organisms. The HIGH signature, the KMSKS pentapeptide motif (Burbaum, J. J., et al., Proteins 7:99–11 (1990)), the PXXP motif (Schimmel, P., et al., Protein Science 1:1387–1391 (1992)) and the anticodon binding determinant residue (Arg/Lys) ((Shepard, A., et al., Proc. Natl. Acad. Sci. USA 89:9964–9968 (1992)) are well conserved. Patterns of conserved residues, deletions and insertions, as well as amino acid sequence similarities shown as analyzed in Table 2 can be used to separate the six IleRSs of Table 2 into two subgroups. One group includes the *E. coli* and human type A enzymes, and the other group includes the cytoplasmic enzymes of lower eucaryotes, the enzyme of an archaebacterium, and the human type B enzyme.

TABLE 2

Similarity among IleRSs from different organisms.

| Enzyme | Ec-I | Hs-Ia | Hs-Ib | Sc-I | Tt-I | Mt-I |
|---|---|---|---|---|---|---|
| Ec-I | 1.0000 | 0.5915 | 0.4304 | 0.4497 | 0.4330 | 0.4980 |
| Hs-Ia | | 1.0000 | 0.4271 | 0.4304 | 0.4324 | 0.4954 |
| Hs-Ib | | | 1.0000 | 0.7263 | 0.7212 | 0.5424 |
| Sc-I | | | | 1.0000 | 0.7024 | 0.5424 |

TABLE 2-continued

| Similarity among IleRSs from different organisms. Similarity Values | | | | | | |
|---|---|---|---|---|---|---|
| Enzyme | Ec-I | Hs-Ia | Hs-Ib | Sc-I | Tt-I | Mt-I |
| Tt-I | | | | | 1.0000 | 0.5280 |
| Mt-I | | | | | | 1.0000 |

Sequence comparison was performed using DISTANCE which compares sequences using the modified Dayhoff comparison table (Gribskov and Burgess, Nucleic Acids Res. 14:6745 (1986)). In this comparison the C-terminal domain after the PXXP motif was omitted from each sequence. Each value was calculated by dividing the number of matches between each sequence pair by the length of shorter sequences without gaps.
Ec, *Escherichia coli* (Webster et al., Science 226:1315 (1984)).
Hs, *Homo sapiens*
Sc, *Saccharomyces cerevisiae* (Englisch et al., Biol. Chem. Hoppe-Seyler 368:971 (1987); Martindale et al., Curr. Genet. 15:99 (1989)).
Tt, *Tetrahymena thermophila* (Csank and Martindale, J. Biol. Chem. 267:4592 (1992)).
Mt, *Methanobacterium thermoautotrophicum* (Jenal et al., J. Biol. Chem. 266:10570 (1991)).

Divergence of the two groups is especially evident in the region C-terminal to the PXXP motif. The *E. coli* subgroup (includes partial C-terminal sequences from two other bacteria) is characterized by the presence of a zinc-finger-like sequence, KCpRCW and iCgRCv towards the end of the C-terminal region. The yeast cytoplasmic subgroup lacks this zinc-finger-like motif but some residues are highly conserved among four enzymes of this subgroup. From the sequence similarity analysis and other information discussed below, it was concluded that the type A gene and the type B gene are the human mitochondrial and cytoplasmic IleRS genes, respectively. The unique feature of the human type B enzyme is the presence of an additional extension domain composed of 190 amino acids at its C-terminal end. This domain is composed of two repeated units.

Two Types of Human Enzymes

It was concluded that the type A gene is the mitochondrial IleRS gene and the type B gene is the cytoplasmic IleRS gene for the following reasons.

1) Generally, the amino acid sequences of mitochondrial and chloroplast enzymes, although they are encoded by nuclear genes, are more similar to their eubacterial counterparts than they are to the amino acid sequences of the cytoplasmic enzymes, reflecting the endosymbiotic origin of these organelles (Martin W. and Cerff, R., Eur. J. Biochem. 159:323–331 (1986)). As shown in Table 2, the structure of the type A enzyme is related to that of *E. coli*, a eubacterial species.

2) Patients with the autoimmune disease polymyositis have been found to produce antibodies to human tRNA synthetases (Targoff, L. N., J. Immunol. 144:1737–1743 (1990)). One of the proteins that could be immunoprecipitated with patient serum containing anti-OJ antibodies has a molecular weight of 146 kD, which is close to the predicted molecular weight of the type B gene product. A later study showed that a human IleRS was the major antigen for most sera with autoantibodies that immunoprecipitated the multienzyme complex of aminoacyl-tRNA synthetases (Targoff, LN. et al., J. Clin. Invest. 91:2556–2564 (1993)).

3) The open reading frame shows the existence of an extra N-terminal domain in the type A IleRS which is absent from IleRSs of other organisms. This domain could function as a mitochondrial-matrix-targeting peptide. Enrichment of Arg and Ser residues in the N-terminal region of type A IleRS supports this possibility (von Heijne, G., et al., Eur. J. Biochem. 180:535–545 (1989)).

4) In mammalian cells, the cytoplasmic form of aminoacyl-tRNA synthetases for Asp, Glu, Ile, Lys, Leu, Met, Pro, Gln and Arg form high molecular weight multisynthetase complexes (Mirande, M., Progress in Nucleic Acid Research 40:95–142 (1991)). Newly evolved extra domains, such as the N-terminal 34-amino acid extension of human AspRS (Mirande, M. et al., Eur. J. Biochem. 203:459–466 (1992)), the internal three repeats of 75 amino acids of human Glu-ProRS (Cerini, C., et al., EMBO J. 10:4267–4277 (1991)), and the N-terminal 73-amino acid extension of rat ArgRS (Lazard M. and Mirande M., Gene 132:237–245 (1993)) have been proposed to be involved in multisynthetase complex formation. The C-terminal extension of 190 amino acids found in the human type B gene product, which is dispensable for enzyme activity, is a strong candidate for the domain responsible for multisynthetase complex formation of IleRS. The sequence of this extension domain does not have sequence similarity to any of the extra domains from AspRS, Glu-ProRS or ArgRS.

The human enzyme is 328 amino acids longer than its *E. coli* counterpart and virtually all of this additional length is found at the C-terminal end. Approximately two-thirds of this additional sequence is due to a repeated element of 95 amino acids which is not found in any of the other sequences. The sequence of this 190 amino acid extra domain is not similar to any sequence in other tRNA synthetases or in proteins compiled in the PIR database (National Biochemical Research Foundation, Protein Identification Resource, Release 39.0). The N-terminal 34 amino acid extension of human cytoplasmic aspartyl-tRNA synthetase (Mirande, M., et al., Eur. J. Biochem. 203:459–466 (1992)), the N-terminal 73 amino acid extension of rat cytoplasmic argininyl-tRNA synthetase (Lazard, M. et al., Gene 132:237–245 (1993)), and the three 75 amino acid internal repeats of the human cytoplasmic glutamyl-prolyl fusion tRNA synthetase (Cerini, C., et al., EMBO J. 10:4267–4277 (1991)) have all been proposed as motifs needed for assembly of the multi-synthetase tRNA complex (Mirande, M., Progress in Nucleic Acid Research 40:95–142 (1991)). If the repeated sequence in human cytoplasmic isoleucyl-tRNA synthestase is required for assembly into this complex, and if the unique additional sequences in the other mammalian sequences have the same function, then it would appear that the sequence for complex assembly and its location are idiosyncratic to the human enzyme.

Northern Blot Analysis

The sizes of poly(A)+ mRNAs that hybridize with type A and type B cDNA clones were determined by northern blot analysis (Example 4). A single transcript of 3900 nucleotides was observed to hybridize with the type A probe. Using the type B probe, a major transcript of 4500 nucleotides and minor transcripts of 8200 and 9500 nucleotides were observed. These unidentified minor transcripts could be products from the type B gene or transcripts from genes homologous to the type B gene.

Expression of Type B Core Enzyme in E. coli

A comparison of the RNA sequences of the isoacceptors of the *E. coli* tRNA$^{Ile}$ and mammalian cytoplasmic tRNA$^{Ile}$ (Sprinzl et al., Nucleic Acids Res. 17:r1–r172, 1989) shows that these sequences have diverged. Not all of the identity-determinant residues determined for *E. coli* tRNA$^{Ile-1}$ (Nureki et al., J. Mol. Biol. 236:710–724 (1994)) are conserved in mammalian cytoplasmic tRNA$^{Ile}$. For this reason, it was anticipated that the *E. coli* enzyme would not be able to charge the mammalian cytoplasmic isoleucyl-tRNAs. Expression of the human enzyme produced in *E. coli* cells could be tested by assaying these *E. coli* cell extracts for aminoacylation of mammalian tRNA with isoleucine. The nearly full length type B human enzyme (codons 6–1266) was cloned behind a T7 promoter (pKS395; Example 5). These cells were then infected with λ-phage CE6 (cI$^{857}$, Sam7) which carries the T7 phage polymerase gene under the $P_L$ and $P_I$ promoters (Studier et al., *Methods in Enzymology*, eds. Goeddel, pp.60–89, 1990) and soluble fractions were prepared. However, expression of the nearly full length human protein seemed to result in protein precipitation, and charging activity was not observed. A comparison of the crude cell extract with the supernatant after a centrifugation step (10,000 g for 30 min) on an SDS-polyacrylamide gel showed that the protein band thought to be the IleRS product was not present in the supernatant, although it was in the crude extract.

Alternatively, the core enzyme missing the repeated sequence at the C-terminal end, and comprising codons 6 to 1085, was cloned into the same vector, resulting in pKS402 (Example 5). Expression of this coding sequence resulted in detection of a new protein that had a molecular weight of 125 kilodaltons, when *E. coli* cell extracts (Example 6) were subjected to SDS gel electrophoresis. Extracts of cells containing the parent plasmid vector alone showed no aminoacylation activity on mammalian tRNA. In contrast, aminoacylation activity with isoleucine could be measured in extracts of cells expressing the truncated human cytoplasmic enzyme (See FIG. 1; Examples 6 and 7), although most of this enzyme was recovered in the insoluble fraction after sonication.

The present invention is more specifically illustrated in the following examples, which are not intended to be limiting in any way.

EXAMPLE 1

Reverse Transcriptase (RT)-PCR

Human fetal fibroblast cell strain TIG-2 (Ohashi et al. *Exp. Geront.* 15:121–133 (1980)) was cultured in Dulbecco's modified Eagle medium (GIBCO-BRL, New York) supplemented with 5% fetal bovine serum (Cell Culture Laboratories, Cleveland). Poly(A)$^+$ mRNA was isolated as described (Sambrook et al. *Molecular Cloning: A Laboratory Manual*, 1989). About 1 μg of poly(A)$^+$ mRNA was converted to cDNA using the cDNA Cycle Kit (Invitrogen, San Diego). Using 1/25th of this cDNA, PCR amplification was performed in 100 μl of 10 mM Tris HCl (pH 8.3), 1.5 mM MgCl$_2$, 50 mM KCl, 0.1 mg/ml gelatin, 50 μM of each dNTP, 100 pmole of each primer and 1.25 units of Taq DNA polymerase (Boehringer Mannheim, Mannheim). The reactions were run for 35 cycles with 2 min at 94° C., 2 min at 55° C. and 3 min at 72° C. for each cycle. The products were cloned into the EcoRI site or SmaI site of phagemid pTZ19R (Mead et al., *Protein Engineering* 1:67–74 (1986)). These cloned fragments could then be recovered by restriction digests of this phagemid for later labeling with $^{32}$P and use as probes in Example 2.

EXAMPLE 2

Screening the Human cDNA Library

A cDNA library was constructed from poly(A)$^+$ mRNA from the human T cell line KUT-2 (Zu, Y., et al., *Biochemistry* 29:8319–8324 (1990)), using the vector pSI4001 (Shigesada et al., *Gene* 53:163–172 (1987)). About 10$^6$ colonies were transferred from LB agar plates containing ampicillin to Duralon-UV membranes (Stratagene, La Jolla) and immobilized by alkaline denaturation and UV irradiation (Sambrook et al. *Molecular Cloning: A Laboratory Manual*, 1989). DNA probes ($^{32}$P labeled) were prepared with the Random Primer DNA Labeling Kit (Takara, Ohtsu). Hybridization and washing steps were done according to Sambrook et al. Autoradiography was performed to locate colonies containing cDNA clones positive for DNA homologous to the probes made by PCR in Example 1.

EXAMPLE 3

DNA Sequencing cDNA inserts in the positive clones from Example 2 were recloned into phagemid vector pTZ19R or pBluescript II and a unidirectional deletion was made using the Kilo-Sequence Deletion Kit (Takara, Ohtsu). Single stranded DNA was obtained by superinfection with helper M13 K07 phage (Mead et al., *Protein Engineering* 1:67–74 (1986)) and sequences were determined using an automated DNA Sequencer (Pharmacia). The 5' regions of types A and B cDNAs were extended by 219 and 232 nucleotides, respectively, with the modified Rapid Amplification of cDNA Ends (RACE)-PCR method (Dumas et al., *Nucleic Acids Res.* 19:5227–5232 (1991)), using 5'-RACE-Ready cDNA from human brain (Clontech, Palo Alto). The 5' region of the type A cDNA was extended an additional 13 nucleotides using a different CDNA library from human lung. The DNA sequences determined by these methods are SEQ ID NO:1 and SEQ ID NO:3.

EXAMPLE 4

Northern Blotting

Five μg of poly(A)$^+$ RNA isolated from the human HeLa-fibroblast hybrid cell line CGL-1 (Stanbridge et al. *Somat. Cell Genet.* 7:699, 1981; provided by Dr. Yudate) was fractionated through a 1% formaldehyde-agarose gel and transferred onto a Duralon-UV nylon membrane (Stratagene). A 1.8 kb BstEII-HindIII fragment (corresponding to codons 65 to 670) from the type A cDNA clone and a 1.7 kb NcoI-NcoI fragment (corresponding to codons 92–659) from the type B cDNA clone were labeled with [α-$^{32}$P]dCTP using the Random Primer DNA Labeling Kit (Takara, Ohtsu). The labeled fragments were used as probes in northern hybridization experiments (Sambrook et al. *Molecular Cloning: A Laboratory Manual*, 1989). The membrane was washed with 0.3 M NaCl, 0.03 M sodium citrate (pH 7.0) and 0.1% SDS at 65° C. after probe hybridization. Autoradiography of the dried membrane revealed mRNA bands as described in the Detailed Description.

EXAMPLE 5

Construction of pKS402

The original construct containing the type B cDNA insert (nucleotides 233–4500 of SEQ ID NO:3) in pSI4001 (Shigesada et al., *Gene* 53:163–172 (1987)) was called pIB1. From pIB1, an EcoRI site in the vector and the PstI site at nucleotide 1899 of the type B cDNA insert were used to generate a fragment which was then inserted into the EcoRI-PstI site of pTZ19R (Mead et al., *Protein Engineering* 1:67 (1986)) to make pIB1-2. The EcoRI-PstI fragment of pIB1-2 was cloned into the EcoRI-PstI site of pBluescript KS(+) to make pIB1-21. The EcoRI-PstI fragment of pIB1-21 was cloned into the EcoRI-PstI site of pBluescript KS(-) to construct pIB1-22. pIB1-22 DNA was mutagenized with oligonucleotide KY208 (SEQ ID NO:5) to introduce an NdeI site at the sixth codon of the coding sequence, which is a codon for methionine, using an Amersham in vitro mutagenesis kit. The resulting plasmid is pKS368.

pKS315 is a derivative of pTZ19R which contains a fusion gene consisting of the genes encoding bovine inositol monophosphatase and $E.\ coli$ IleRS. It was used in this construction because of its convenient restriction sites. The 1690 basepair (bp) NdeI-NotI fragment of pKS368 was ligated with the NdeI-NotI 2965 bp fragment of pKS315 to construct pKS371. The 577 bp HindIII-StuI fragment of pKS371 was cloned into the HindIII and StuI sites of pIB1 to construct pKS387.

pKS314 is a derivative of pET-3a (Studier, F. W., et al., In D. V. Goeddel (Ed.), Methods in Enzymology, pp. 60–89 (1990)) which contains an insertion of the gene encoding bovine inositol monophosphatase. It was used for its convenient restriction sites. The 4.5 kb XbaI-MluI fragment of pKS387 was cloned into the XbaI-MluI site of pKS314 to make pKS391.

pKS292 is a derivative of pET-3a which contains the suhB gene of $E.\ coli$ in the wrong orientation with respect to the T7 promoter. It was used for the convenient restriction sites in the insertion. pKS391 was partially digested with NdeI and the 6312 bp fragment was self-ligated to make pKS398. The 3460 bp XbaI-Asp718 fragment of pKS398 was cloned onto the XbaI-Asp718 fragment of pKS292 to construct pKS402. The plasmid pKS402 encodes a core region of the type B enzyme (amino acid residues 6 to 1086).

The 4.8 kb XbaI-Asp718 fragment of pKS391 was cloned onto the XbaI-Asp718 fragment of pKS292 to construct pKS395. The plasmid pKS395 encodes amino acid residues 6 to 1266 of the type B enzyme.

EXAMPLE 6

Expression of Type B Core Enzyme in $E.\ coli$

Recombinant plasmid pKS402 was introduced into $E.\ coli$ strain HMS174 (recA, hsdR, rpoB). The strain containing plasmid pKS402 was grown on 50 ml of LB broth (Sambrook et al. Molecular Cloning: A Laboratory Manual, 1989)) containing 50 µg/ml of carbenicillin (Sigma) and 0.04% maltose at 37° C. At $OD_{600}$=0.3, glucose (0.4%), $MgSO_4$ (10 mM) and λ phage CE6 ($3\times10^9$ pfu/ml) were added. Cells were grown at 37° C. for an additional 4 h, harvested, resuspended in 10 ml of 50 mM 2-mercaptoethanol, 0.1 M NaCl, 50 mM $NaPO_4$ (pH 7.5) containing 1 mM phenylmethylsulfonyl fluoride, disrupted by sonication (two cycles of 15 sec, Bioruptor) and clarified by centrifugation (100,000 g for 30 min).

EXAMPLE 7

Assay for tRNA Charging Activity

The aminoacylation assay employed is described in Shiba and Schimmel, J. Biol. Chem. 267:22703 (1992), which was based on the procedure described by Shepard et al. (Proc. Natl. Acad. Sci. USA 89:9964–9968 (1992)). To each reaction mixture was added 10 µl of crude extract made from 50 ml of cell culture (approximately 25 µg of protein as determined by the BioRad protein assay kit). The reaction mixture also contained 0.1 µCi/µl of L-[4,5-$^3$H(N)] isoleucine (89.6 Ci/mmol, NEN), 0.4 mg/ml of calf liver tRNA (Boehringer Mannheim) and was 20 µM in L-isoleucine. The reaction mixture also contained 0.1 mg/ml bovine serum albumin, 20 mM KCl, 10 mM $MgCl_2$, 20 mM 2-mercaptoethanol, 4 mM ATP and 50 mM sodium phosphate (pH 7.5). After various times of incubation at 37° C., an aliquot of the reaction was removed and spotted onto Whatman 3MM paper filter disks which had been pre-soaked in 5% trichloracetic acid. The filter disks were immediately placed into cold 5% trichloroacetic acid. The filters were washed three times with cold 5% trichloracetic acid, washed twice with 95% ethanol and once with ether, dried under a heat lamp, and subsequently subjected to scintillation counting. FIG. 1 shows a time course assay of the charging activity of extracts made from $E.\ coli$ cells containing either pKS402 or the parental type plasmid, pET-3a, and subjected to the growth and infection conditions in Example 6.

EXAMPLE 8

GST Fusions of Hu IRS-A and Hu IRS-BΔC

Cloning human cytoplasmic and mitochondrial isoleucyl-tRNA synthetase genes in a $S.\ cerevisiae$ yeast expression vector Standard molecular biology methods were used (Ausubel, F. M., et al., (eds.) Current Protocols in Molecular Biology, John Wiley & Sons, New York, 1992). Enzymes were purchased from New England Biolabs. $E.\ coli$ strain DH5α was used for propagating plasmids.

pQB95

A 2887 bp fragment containing 955 amino acids (codons 39 to 993 of SEQ ID NO:1) of human mitochondrial isoleucyl-tRNA synthetase (Hu IRS-A) gene lacking its leader sequence was isolated from pKS405 (see below) by NdeI partial digestion, filling in 5' overhangs with Klenow fragment, heat-inactivating the enzymes, and then XhoI digestion. The resulting DNA fragment was subcloned into SmaI- and SalI-digested pQB83, a derivative of PEG(KG) (Mitchell, D. A. et al., Yeast 9:715–723 (1993)) in which the leu2-d gene was deleted by BstEII and NruI digestion, filling in with Klenow fragment and self-ligation. The resulting plasmid, pQB95, was designed to express Hu IRS-A in yeast as a galactose-inducible GST-fusion with a predicted molecular weight of ~133 kD.

pQB98

A 3251 bp fragment containing the human cytoplasmic isoleucyl-tRNA synthetase core enzyme sequence (codons 6 to 1086 of SEQ ID NO:3; "Hu IRS BΔC"), isolated from pKS402 by partial digestion with NdeI followed by Klenow treatment to fill in 5' overhangs, was subcloned into SmaI-digested pUC19 (New England Biolabs) to yield pQB97. pQB97 was then digested with EcoRI and HindIII (sites from the pUC19 vector) to release a 3.3 kb fragment containing the human gene, which was subcloned into EcoRI- and HindIII-digested pQB83 (see above). The resulting plasmid, pQB98, was designed to express Hu IRS-BΔC in yeast as a galactose-inducible GST-fusion protein of 1310 amino acids (1083 amino acids from pKS402 plus 7 amino acids from pUC19 plus 220 amino acids from GST), with a predicted molecular weight of ~148 kD.

pKS405

The 258 bp XbaI-Asp718 fragment of pKS372 (see below) was cloned into the XbaI-Asp718 site of pKS292 (see Example 5) to construct pKS401. The BstEII-Asp718 fragment of pIA1-12 (see below) was cloned into the BstEII-Asp718 site of pKS401 to produce pKS405.

pKS372

The 5' region of Human IleRS-A was extended by RACE-PCR using 5'-Amplifinder RACE kit (Clontech). Template mRNA was human lung mRNA that was provided with the kit. Oligonucleotides used were KY75 (CCGTTTGCATAAGGAGGTCCA; SEQ ID NO:18) and KY175 (CATCATGAAGGCAAAATTCTGTCTT; SEQ ID NO:19). The amplified DNA fragment was treated with *E. coli* DNA polymerase I and T4 polynucleotide kinase and cloned into the SmaI site of pTZ19R to obtain plasmid #21. Plasmid #21 has nucleotides 14 to 285 of the human mitochondrial IleRS gene (IleRS-A). Nucleotides 15–285 of IleRS-A were cloned by PCR amplification of #21 using oligonucleotides KY175 and KY204 (KY204= ACGCCCCGCCTTCCCTGCAGCCCGG; SEQ ID NO:20). This PCR product was mixed with pIA1 and KY204 and KY110 (KY110= TCTTTCTAATTTCCATAGCTG; SEQ ID NO:21) and PCR was carried out to produce nucleotides 14–488 of IleRS-A. This 14–488 PCR product was digested with PstI and DraI and cloned into PstI- and SmaI- cut pTZ19R to produce pKS348, containing the fragment 29-328 of IleRS-A. To introduce an NdeI site, and thus an ATG, at the 6th codon of IleRS-A, pKS348 was mutagenized (using an in vitro mutagenesis kit from Amersham) with the oligonucleotide KY2207 (CACCCGAACTCGCATATGGGCAGATACCGGGAC; SEQ ID NO:22) to make pKS367. The 231 bp NdeI-EcoRI fragment of pKS367 was ligated with the NdeI-EcoRI 2879 bp fragment of pKS315 (see Example 5) to construct pKS372.

PIA1-12

The original isolate from the human DNA library (see Example 2) named pIA1, which has the cDNA insert (nucleotides 233–3387 of SEQ ID NO:1) on vector pSI4001, was digested with MluI and EcoRI and made blunt-ended by Klenow fragment. This blunt-ended fragment containing Hu IRS-A was cloned into the SmaI site of pTZ19R to make pIA1-11. The EcoRI-SalI fragment of pIA1-11 was cloned into the EcoRI-SalI site of pBluescript KS (+) to make pIA1-12.

EXAMPLE 9

Purification and Activity Testing of Human Cytoplasmic and Mitochondrial Isoleucyl-tRNA Synthetases Expressed in *S. cerevisiae* Cytoplasm as GST Fusion Proteins Expression and purification of GST fusion proteins Standard methods for yeast propagation and transformation were used (Ausubel, F.M., et al., (eds.) *Current Protocols in Molecular Biology*, John Wiley & Sons, New York, 1992; Rose, M.D., et al., *Methods in Yeast Genetics*, Cold Spring Harbor Laboratory Press, Cold Spring Harbor, N.Y., 1990). The vector pQB83 and the plasmids pQB95 (Hu I-A) and PQB98 (Hu I-BΔC) were transformed into yeast strain EY699 (Elion, et al., 1991); MATa ade2-1 his3-11,15 leu2-3,112 ura3-52 trp1-63 can1-100 Gal+) by selection on synthetic complete medium lacking uracil (SC-Ura). (Transformants were stored as yeast strains QBY60=EY699 (pQB83), QBY62=EY699(pQB95) and QBY76=EY699 (pQB98).) Purified single transformants were grown to stationary phase in liquid SC-Ura supplemented with 2% dextrose, then diluted into SC-Ura supplemented with 2% raffinose for overnight growth to log phase ($A_{600}$ between 0.5 and 1.0). Cells were pelleted, resuspended in SC-Ura containing 2% galactose, and grown for 6–8 hours at 30° C. to induce the expression of GST fusion proteins. The induced cultures were pelleted, washed with cold sterile water and frozen at −80° C. Total soluble protein was prepared from these cells by lysis with glass beads, essentially as described in Elion, E. A. et al. (*Mol. Biol. Cell* 4:495–510, 1993), except that the lysis buffer was 25 mM Tris (pH 7.5), 150 mM NaCl, 10 mM EDTA, 1 mM $NaN_3$, 0.1% Triton X-100, 10% glycerol, with freshly added 1 mM DTT, and protease inhibitors (Elion, E. A., et al., *Mol. Biol. Cell* 4:495–510 (1993)). Protein concentration was determined by a Bradford assay (Pierce), using bovine serum albumin as a standard. GST fusion proteins were purified from 1000 μg of total protein by binding to 25 μl glutathione agarose (Sigma), as described (Kranz, J. E., et al., *Genes and Dev.* 8:313–327 (1994)), using the lysis buffer above. Glutathione agarose precipitates were washed 5× with lysis buffer, then resuspended in 25 μl SDS-containing (SDS is sodium dodecyl sulfate) sample buffer, boiled 5 minutes and loaded on an SDS-polyacrylamide gel. Single bands of the predicted size for both the GST-Hu IRS-A fusion and the GST-Hu IRS-B fusion were detected by Coomassie blue staining.

Purification and Activity of Hu IRS B-ΔC

Figure 2:
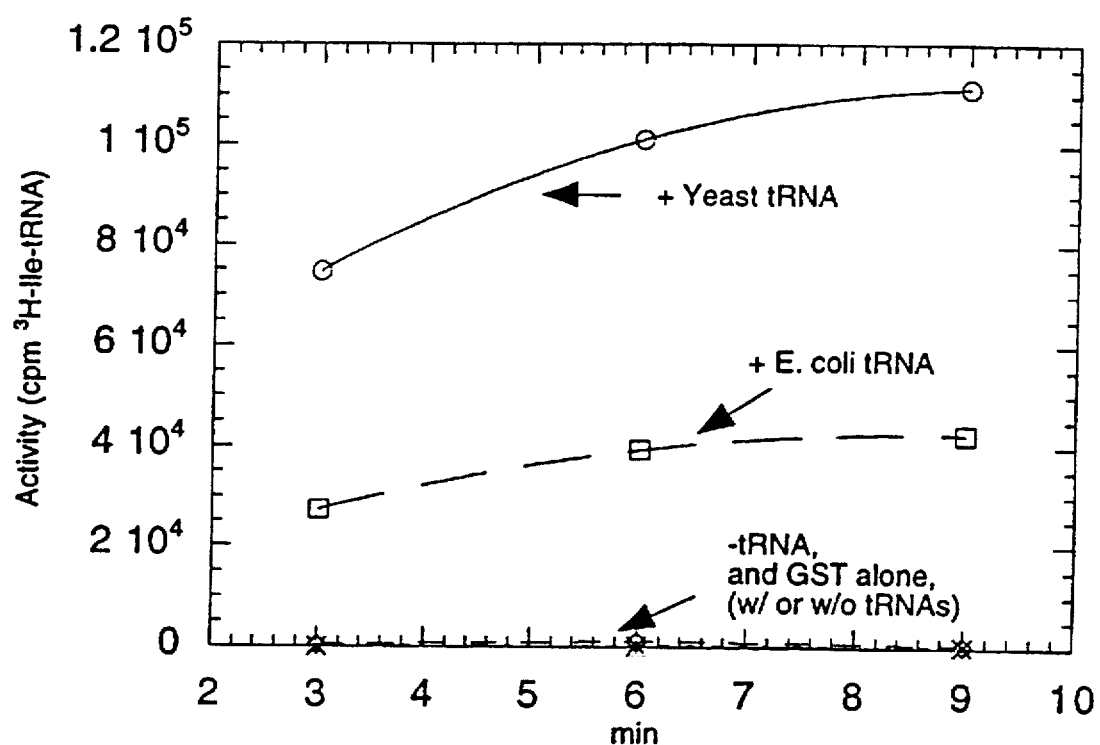
FIG. 2 is a graph showing the amount of aminoacylated tRNA product over time, produced by the enzymatic activity of GST-Hu IRS BΔC protein purified from *S. cerevisiae* cells (see Example 9). Symbols are: ○, brewer's yeast tRNA used as substrate; □, *E. coli* tRNA used as substrate; X, purified GST-Hu IRS BΔC protein used as enzyme, no tRNA substrate; ◊, glutathione S-transferase (GST) portion alone purified from *S. cerevisiae* cells used as enzyme, yeast tRNA used as substrate; Δ, GST purified from *S. cerevisiae* cells used as enzyme, no tRNA substrate.

To determine if either of these fusions were active, they were purified on a larger scale, as described (Ausubel, F. M., et al., (eds.) *Current Protocols in Molecular Biology*, John Wiley & Sons, New York, 1992), from 30 mg of yeast total protein (from a 400 ml culture, induced as described above) on a 2 ml glutathione agarose column. Pure GST fusion protein (or GST alone, as a control) was eluted from the glutathione agarose using 10 mM reduced glutathione (Sigma), as described (Ausubel, et al., 1992). Eluates were concentrated in a Centricon-30 (Amicon), resuspended at 1 mg/ml in 50% glycerol, 50 mM Tris (pH 7.5) and 1 mM DTT and stored in aliquots at −80° C. For GST-Hu IRS-BΔC, the typical yield was about 1 mg per liter of cells. Aminoacylation assays were performed as described previously (see Example 7) using 80 nM protein (0.5 μg for GST-Hu IRS-BΔC; 0.1 μg for GST alone (negative control), 20 μM $^3$H-isoleucine, 4 mM ATP, 10 mM KF, 0.1 mg/ml bovine serum albumin, 50 mM HEPES (pH 7.5), 10 mM $MgCl_2$, 30 mM $NH_4Cl$ and 10 mM 2-mercaptoethanol. As substrate, either *E. coli* or brewer's yeast tRNA (Sigma) was added to a final concentration of 0.24 mM. FIG. 2 shows that purified GST-Hu IRS-BΔC can charge both *E. coli* and yeast tRNA, while no activity is seen without tRNA or with GST alone purified from the same yeast strain.

Purification and Activity of Hu IRS A

Because the GST-Hu IRS-A fusion did not elute from glutathione agarose with 10 mM glutathione (Western analysis of the eluate, washes and of the column material itself with affinity purified α-GST polyclonal antibody revealed that GST-Hu IRS-A protein remained bound to the column), a "solid-phase charging assay" was performed to test for activity. GST alone and GST-Hu IRS BΔC were used as negative and positive controls, respectively. Small-scale purification (as described above) was performed to yield a total of 2 μg protein, as detected by SDS-PAGE. Before the last wash of the glutathione agarose precipitates, the 1000 μl buffer and resin were divided into 3 tubes——1 to visualize by SDS-PAGE, and the others (each containing approximately 0.6 μg protein) to perform charging assays with either *E. coli* or yeast tRNA. The glutathione agarose was precipitated by a 30 second centrifugation at 1000 rpm in a microfuge, and a gel-loading pipet tip was used to pipet off all buffer from the 10 µl precipitate. Reaction components (see above) were added to a final volume of 50 µl, and the tubes were incubated at 37° C., with occasional tapping to assure the precipitate remained mixed with assay components. At time points of 12, 24 and 36 minutes, samples were taken and counted, only the GST Hu IRS-BΔC was active, yielding >25,000 cpm with either substrate at 12 minutes and 40,000 cpm at 36 minutes. Both GST-Hu IRS-A and GST gave only background counts of ~200 cpm at all time points. Thus, GST Hu IRS BΔC is active as either a soluble protein or when bound to glutathione agarose, while the GST-Hu IRS-A, expressed as a cytoplasmic protein in yeast, appears to be inactive under the conditions used.

EXAMPLE 10

Creating an *S. cerevisiae* Null Strain for Expression of Human Cytoplasmic Isoleucyl-tRNA Synthetase and Complementation Tests ILS1, the gene encoding cytoplasmic isoleucyl-tRNA synthetase of *Saccharomyces cerevisiae*, has been cloned and sequenced previously (Englisch, U., et al., *Biol. Chem. Hoppe-Seyler*, 368:971–979 (1987); Martindale, D. W., et al., *Curr. Genetics* 15:99–106 (1989)). ATCC lambda clone PM4967 (ATCC Accession Number 70323), containing about 20 kb of the *S. cerevisiae* genome from chromosome II that includes the ILSI gene, was used to infect *E. coli* strain C600. Phage DNA was prepared, and digested with EcoRI to release a 6 kb fragment, or with BamHI to release a 5.2 kb fragment, containing the ILS1 gene and flanking DNA. The EcoRI fragment was subcloned into the EcoRI site of phagemid pBSKS(+) (Stratagene), yielding pQB76, and the BamHI fragment was subcloned into pBSKS(+), YCplac33, YCplac111, or YEplac181 (Gietz, R. D. and Sugino, A., *Gene* 74:527–534 (1988)) to make, respectively, pQB74, pQB89, pQB91, and pQB93.

To construct a chromosomal deletion of ILS1 by gammatransformation (Sikorski, R. S., and Hieter, P. *Genetics* 122:19–27 (1989)), a TRP1 integrating plasmid, pRS304 (Sikorski, R. S., and Hieter, P. *Genetics* 122:19–27 (1989)), containing 5' and 3' flanking sequences of ILS1, was made. The 1 kb EcoRI-BamHI fragment of pQB76 (the 5' flank) and the 800 bp HpaI-EcoRI fragment of pQB76 (the 3' flank) were ligated to BamHI- and SmaI-cut pRS304, to produce pQB118. Digestion of pQB118 with EcoRI yields a linear piece of DNA with the 5' and 3' flanking sequences of ILS1 now flanking the TRP1 marker (and plasmid DNA). Strain FY83 (MATa/α lys2-128δ/lys2-128δ leu2Δ1/leu2Δ1 ura3-52/ura3-52 trp1Δ63/trp1Δ63), obtained from Fred Winston (Harvard Medical School), was transformed with 5 µg EcoRI-cut pQB118 and plated on SC-Trp plates to construct a heterozygous (i.e., ILS1⁺/ils1Δ::TRP1) strain by one-step gene disruption (Rothstein, J., *Methods Enzymol.* 101:202–211 (1983)). Independent Trp⁺ transformants were purified, their genomic DNA isolated and digested with XbaI, and screened by Southern analysis (using the 800 bp EcoRI-HpaI ("3' flank") fragment as a probe) for presence of the disruption.

A transformant (QBY182) containing both a 2.5 kb (ILS1) and a 4.2 kb (ils1Δ::TRP1) band was sporulated and upon tetrad dissection revealed 2:2 segregation (i.e., 2 viable and 2 dead spores). All viable spores were Trp-, indicating that TRP1 is linked to inviability, as expected for spores inheriting the chromosome with the ils1Δ::TRP1 disruption.

To recover a haploid null strain to be used in complementation studies, QBY182 was transformed to Ura⁺ with the ILS1 maintenance plasmid pQB89. This transformant was sporulated, tetrads were dissected, and two haploid Trp⁺ Ura⁺ spores of opposite mating type were identified and designated QBY187 (MATα leu2Δ1 lys2-128δ ura3-52 trp1Δ63 ils1Δ::TRP1/pQB89) and QBY188 (MATa leu2Δ1 lys2-128δ ura3-52 trp1Δ63 ils1Δ::TRP1 /pQB89).

EXAMPLE 11

Complementation Testing of Human Isoleucyl-tRNA Synthetase Genes in *S. cerevisiae* Complementation of ils1Δ by Hu IRS-BΔC and -B but not -A Construction of "tester plasmids"

Plasmid pMC4 carries the ADH promoter of *S. cerevisiae*, and downstream of the promoter, the coding sequence for the cytochrome oxidase IV mitochondrial targeting peptide (Pinkham, J. et al., *Mol. Cell. Biol.*, 14:4643–4652, (1994); Hurt, E. C. et al., *J. Biol. Chem.*, 262:1420–1424 (1987); Hurt, E. C., et al., *EMBO J.*, 3:3149–3156 (1984)). Derivatives of plasmid pMC4 can be constructed which lack or interrupt the sequence encoding the mitochondrial targeting sequence (e.g., by insertion of a gene between the promoter and targeting sequence), permitting cytoplasmic expression. Alternatively, the ADH promoter of pMC4 can be excised and inserted into another suitable vector. pQB169, which was constructed for the expression of heterologous genes in yeast cytoplasm, is an example of a vector constructed in this manner.

pQB169 contains the constitutive ADH promoter, a polylinker and the ILS1 transcription terminator. A 450 bp fragment containing the constitutive ADH promoter (pADH) with its transcriptional start sites but not with a translational start site (i.e., ATG) was amplified by PCR using plasmid pMC4 (Hurt, et al., *J. Biol. Chem.* 262:1420–1424 (1987)) as template. Primers were designed to incorporate a HindIII site at the 5' end (primer JK-1; SEQ ID NO:23) of the fragment and a PstI site at the 3' end (primer JK-2; SEQ ID NO:24):

*HindIII*
JK-1: 5'-CCA AGA AGC TTG AAG TAA TAA TAG GCG CAT GC

*PstI*
JK-2: 5'-CGT ACT GCA GGA TTG TAT GCT TGG TAT AGC

The resulting PCR product was cleaved with HindIII and PstI. This HindIII-PstI pADH fragment containing the ADH promoter was subcloned into the HindIII and PstI-cut vector YEplac181 (Gietz, R. D. and Sugino, A., *Gene* 74:527–534 (1988)), a 2µ LEU2 yeast shuttle vector, yielding intermediate plasmid pQB147.

For efficient transcription termination, a terminator fragment (tILS1, containing conserved transcription termination signals (Zaret and Sherman, *Cell* 28:563–573 (1982)) was generated by PCR using plasmid pQB89 as template. pQB89 is a derivative of YCplac33 (a URA3, CEN4 plasmid; Geitz and Sugino, *Gene*, 74:527–534 (1988))). pQB89 was constructed by subcloning a 6 kb BamHI fragment obtained from a λ clone (ATCC Accession No. 70323) containing a yeast genomic fragment which includes the ILS1 gene (yeast cytoplasmic isoleucyl-tRNA synthetase gene; Englisch et al., *Biol. Chem. Hoppe-Seyler*, 368: 971–979 (1987)) into YCplac33.

The 270 bp tILS1 PCR fragment was engineered to have an EcoRI site at the 5' end (JK-5; SEQ ID NO:25), and a NarI site at the 3' end (JK-6; SEQ ID NO:26), and contains the 3' untranslated region of ILS1, including bases 3519–3846 of the ILS1 gene (Englisch, U. et al., *Biol. Chem. Hoppe-Seyler* 368:971–979 (1987)). The primers used to prepare this fragment were:

```
            EcoRI
JK-5:  5'-GGA ATT CTG AAA ACA ACT CAT ATA AAT ACG

NarI
JK-6:  5'-GAG GCG CCC TCT TAT CAA TCC CCT CCT CAA CC
```

The resulting PCR product was cleaved with EcoRI and NarI. pQB147 was cleaved with EcoRI and NarI, and the EcoRI-NarI tILS1 fragment was subcloned into the EcoRI and NarI sites of the vector to yield expression vector pQB169. Transcription initiates in the pADH, and translation initiates at the first ATG of the cloned insert. Transformants of *E. coli* DH5α containing pQB169 were obtained.

pQB167 carrying Hu IRS-BΔC pQB96, containing the Hu IRS-BΔC gene in pUC19, in the opposite orientation as pQB97 (described above), was digested with PvuI (to cut the vector backbone), XbaI and EcoRI. The 3.2 kb EcoRI-XbaI fragment was cloned into XbaI-EcoRI-digested pQB147 to make pQB167, carrying Hu IRS-BΔC under control of the yeast ADH promoter.

pQB168 carrying Hu IRS-A

A 2887 bp fragment containing 955 amino acids (codons 39 to 993 of SEQ ID NO:1) of the Hu IRS-A gene lacking its leader sequence was isolated from pKS405 by NdeI partial digestion, filling in 5' overhangs with Klenow fragment, heat-inactivating the enzymes, and then XhoI digestion. This fragment was subcloned into EcoRV-SalI cut pBSKS(+) (Stratagene) to yield pQB70. This plasmid was digested with PvuI (to cut the vector backbone), BamHI, and KpnI to release a 3 kb fragment containing Hu IRS-A, which was cloned into BamHI-KpnI-cut pQB147 to make pQB168, carrying Hu IRS-A under the control of the yeast ADH promoter.

pQB180 carrying Hu IRS-B pKS395 (see Example 5) was digested with EcoRI (to cut the vector backbone), then XbaI and KpnI, to generate a 4.9 kb XbaI-KpnI fragment, which was cloned into XbaI-KpnI cut pQB169 to make pQB180, which carries Hu IRS-B (full length) under control of the yeast ADH promoter.

pQB197 carrying ILS1

The 3.6 kb HindIII-AccI fragment from pQB89 (ILS1 in YCplac33; see above) was cloned into HindIII-AccI-digested pBSKS(+) to make pQB157. Digestion of pQB157 with XhoI, filling-in of 5' overhangs with Klenow fragment plus T4 DNA polymerase, heat-inactivation, and digestion with BamHI gave a 3.6 kb fragment. This fragment was cloned into pQB169, which was cut with EcoRI, blunt-ended by Klenow fragment plus T4 DNA polymerase, heat inactivated, and cut with BamHI. The resulting plasmid, pQB197, carries the ILS1 gene under control of the yeast ADH promoter.

Complementation of ils1Δ by Hu IRS-BΔC

To check for complementation of the lethal ils1Δ mutation in QBY187 by the human cytoplasmic isoleucyl-tRNA synthetase, a plasmid shuffle (Sikorski, R. S. and Boeke, J. D., *Meth. Enzymol.* 194:302–318 (1991)) was attempted. Strain QBY187 was transformed with one of the following LEU2 tester plasmids: pQB167 (2µ $P_{ADH}$-HU IRS-BΔC), pQB168 (2µ $P_{ADH}$-Hu IRS-A), pQB180 (2µ $P_{ADH}$-Hu IRS-B) , pQB197 (2µ $P_{ADH}$-ILS1), or pQB169 ($P_{ADH}$ vector alone). Purified single transformants (Ura$^+$ Trp$^+$ Leu$^+$) were streaked on 5-fluoro-orotic acid (5-FOA) plates to select against cells carrying the URA3 maintenance (ILSI) plasmid (Boeke, J. D. et al. *Mol. Gen. Genet.* 197: 345–346 (1984)) and the plates were incubated at 30° C. and 37° C. Neither the negative control (pQB169) nor the Hu IRS-A tester strain showed any growth after 6 days at either temperature. At 30° C., the strain containing the ILS1 tester plasmid grew well in 2 days, while the Hu IRS-BΔC tester strain showed faint growth after 2 days and complete growth after 5 days, and the Hu IRS B tester strain showed no growth after 2 days and only faint growth after 5 days. However, at 37° C., the ILS1 and the Hu IRS-BΔC strains grew equally well, arising in 2 days. The Hu IRS-B tester strain, however, still showed poorer complementation of ils1Δ even at 37° C., in that it showed no growth after 2 days and showed weak growth after 5 days.

To check that the 5-FOA$^+$ colonies (ILS1, Hu IRS-BΔC, and Hu IRS-B transformants) that arose had not undergone gene conversion at either ils1Δ on the chromosome or URA3 on pQBY89, the following two experiments were done:

(1) Rich medium (YPD) was inoculated with independent colonies and grown for at least 10 generations (>24 hours at 37° C.) to allow for plasmid loss. (The Hu IRS-B tester strain did not grow well, even with prolonged incubation, consistent with its weak growth on plates; thus, this strain was not analyzed further.) Cells were diluted and spread on rich (YPD) medium to yield about 200 colonies after 2 days at 37° C. These colonies were replica plated to SC-Ura, SC-Trp, SC-Leu, and SC medium, incubated overnight at 37° C., and scored the following day. All colonies (~600 of each ILS1 and Hu IRS-BΔC tester strain) were Ura- Trp$^+$ Leu$^+$, indicating that the cells had maintained the TRP1 disruption of ILS1 and were dependent on the LEU2 plasmid.

(2) Plasmid DNA was isolated from the same YPD cultures by isolating total DNA, transforming bacteria (DH5α), and preparing plasmid DNA from multiple independent bacterial transformants (~5 for each yeast strain). Restriction analysis revealed that all colonies contained the appropriate tester plasmid. Thus, for the Hu IRS-BΔC tester strain, testing confirmed that the 5-FOA$^+$ colonies have lost the maintenance plasmid, are dependent on a LEU2 plasmid, and that this plasmid is pQB167, containing the Hu IRS-BΔC gene. This strain, QBY214 (MATα leuΔ1 lys2-128δ ura3-52 trp1Δ63 ils1Δ::TRP1/pQB167) is therefore dependent on human cytoplasmic IleRS (BΔC) for survival. Parallel experiments were done with strain QBY188 to generate a MATa version, QBY218.

To check for any potential toxic effects of the heterologous or overexpressed IleRS, growth of the strains was compared on YPD, YPG, SC-Leu, and SC-Ura medium at both 30° C. and 37° C. No differences were observed. Furthermore, parallel experiments transforming these plasmids into QBY189, an ILS1$^+$ strain isogenic with QBY187, again showed no growth differences or obvious toxic effects from the plasmid. Thus, the poorer growth seen in the Hu IRS-B tester strain probably reflects reduced in vivo function (complementation) rather than toxic or dominant-negative effects. The fact that at 37° C. the Hu IRS-BΔC tester strain can grow equally well as the ILS1 strain suggests that at this temperature, the human core enzyme can completely substitute for the endogenous yeast isoleucyl-tRNA synthetase. This difference in complementation by Hu IRS-BΔC and Hu IRS-B is unlikely to be due to differences in expression, since the junction with the ADH promoter is identical. (However, levels of protein have not been checked in these strains, since the induced protein cannot be detected in crude extracts by SDS-PAGE with Coomassie blue staining.) It is possible that the poorer complementation of ils1Δ by the full-length human IleRS could be due to the "interference" of the C-terminal extension (which is not present in the yeast Ils1 protein) with normal function in *S. cerevisiae*, consistent with the hypothesis that this C-terminal extension is involved in associating IleRS with the multi-synthetase complex found in humans but not yeast.

EXAMPLE 12

Expression of Human Isoleucyl-tRNA Synthetase in *Pichia pastoris* Construction of a *Pichia pastoris* Strain for Expression of Human Isoleucyl-tRNA Synthetase The unique XbaI site of pKS398 (see Example 5) upstream of the initiation codon of the human IleRS type B gene was converted to an EcoRI site by making blunt ends with Klenow fragment and dNTPs (Sambrook, J., et al., *Molecular Cloning: A Laboratory Manual*, 2nd Ed., Cold Spring Harbor Laboratory, Cold Spring Harbor, N.Y. (1989)), and then ligating with an EcoRI linker oligonucleotide (GGAATTCC) to construct pKS451. The 3.5 kb EcoRI-EcoRI fragment of pKS451 that contains an open reading frame starting at codon 6 and ending at codon 1086 was cloned into the EcoRI site of the *Pichia pastoris* expression vector pHIL-D2, which has a HIS4 marker (Invitrogen), to yield plasmid pKS454. This plasmid has the cDNA clone for human isoleucyl-tRNA synthetase behind the promoter of the gene for *P. pastoris* alcohol oxidase (AOX1). Two μg of pKS454 were linearized by digesting with NotI (which cleaves at sites within the vector) and the linearized DNA was introduced into spheroplasts of *P. pastoris* strain GS115 (a HIS4 mutant of *Pichia pastoris* (Invitrogen)). HIS+ transformants were selected by growth for 4 days at 30° C. on plates containing 18.6% D glucitol, 1.34% yeast nitrogen base without amino acids (Difco, Detroit), 0.4 μg/ml D-biotin, 2% D-glucose and 50 μg/ml each of L-glutamic acid, L-methionine, L-lysine, L-leucine and L-isoleucine. Colonies which grew were checked for their utilization of methanol by scoring for growth on "MM" plates containing 1.34% yeast nitrogen base without amino acids, 0.4 μg/ml D-biotin (Sigma Chemical Co.) and 0.5% methanol and, separately, on "MD" plates containing 1.34% yeast nitrogen base without amino acids, 0.4 μg/ml D-biotin and 2% D-glucose. If the introduced DNA fragment was integrated into the AOX1 locus of the host chromosome by homologous recombination between the 5' and 3' AOX1 sequences in the pHIL-D2 vector portion of pKS454 and those in the genome, then the resultant cells are disrupted at the AOX1 gene and cannot metabolize methanol as the sole carbon source (Mut-phenotype). One of the His+/Mut- transformants (that grew on MD plates but not on MM plates) was purified as the strain designated NOR-Ib.

Figure 3:
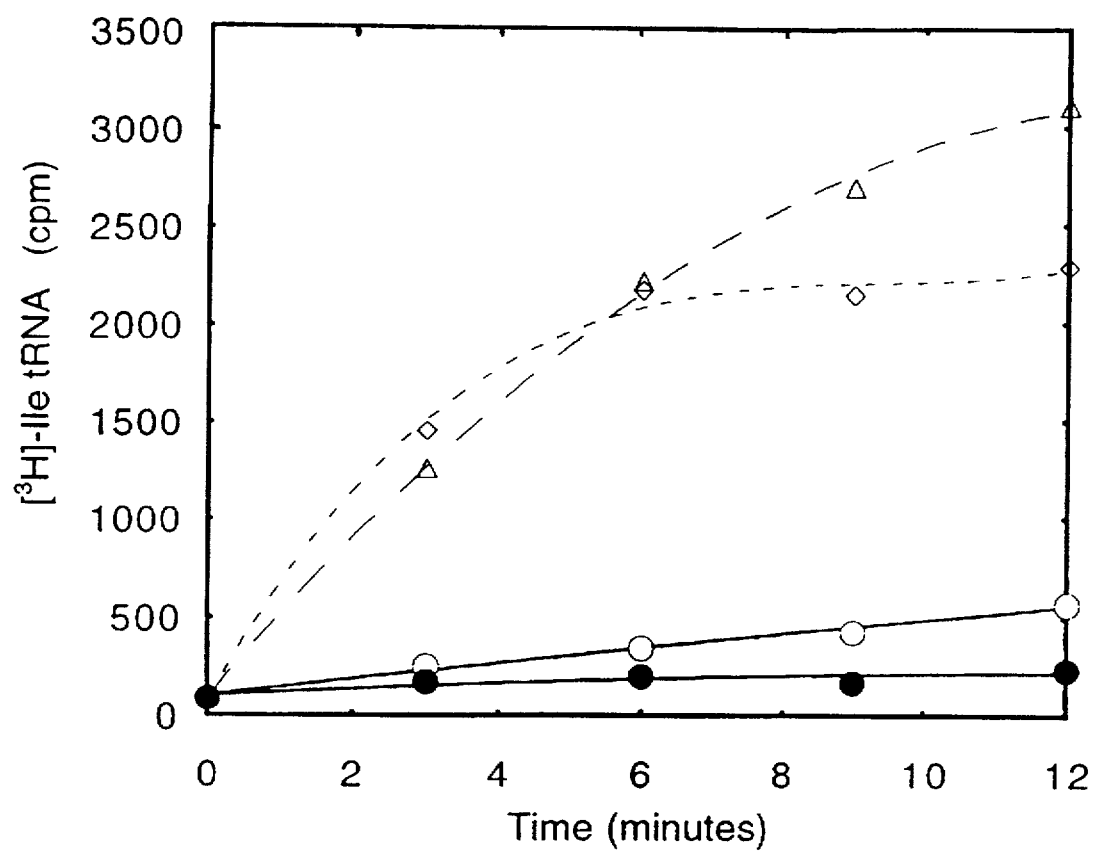
FIG. 3 is a graph showing the amount of aminoacylated tRNA product over time, produced by the enzymatic activity of human isoleucyl-tRNA synthetase protein purified from *Pichia pastoris* strain NOR-Ib. Symbols are: ○, lysate of untransformed *P. pastoris* used as enzyme on *E. coli* tRNA subtrate; ●, lysate of untransformed *P. pastoris* used as enzyme on bovine tRNA substrate; Δ, lysate of NOR-Ib used as enzyme on *E. coli* tRNA substrate; ◊, lysate of NOR-Ib used as enzyme on bovine tRNA substrate (see Example 12).

Expression of Human isoleucyl-tRNA Synthetase in *P. pastoris* and Preparation of Extracts for Aminoacylation of Bovine and *E. coli* tRNA Strain NOR-Ib was grown at 30° C. for 24 h in 5 ml of 1.34% yeast nitrogen base without amino acids, 0.4 μg/ml D-biotin and 1% glycerol. Cells were harvested and resuspended in 10 ml of MM medium and incubated for an additional 66 h at 30° C. The cells were then resuspended in 0.2 ml of 50 mM sodium phosphate (pH 7.4), 1 mM phenylmethylsulfonyl fluoride (Sigma Chemical Co.), 1 mM ethylenediaminetetraacetic acid and 5% glycerol, and broken with acid washed glass beads (425–600 microns (Sigma Chemical Co.)). Aminoacylation activity in cell extracts was assayed as described (Shiba, K. and Schimmel, P., *J. Biol. Chem.* 267:22703–22706 (1992)) using 15 μg of crude extract (determined by the Protein Assay Kit (BioRad, Richmond)), 120 μCi L-[4,5-$^3$H(N)]-isoleucine (80.6 Ci/mmol, New England Nuclear, Boston) in a total reaction mixture of 100 μl containing 0.4 mg/ml of either *E. coli* MRE 600 or calf liver tRNA (Boehringer Mannheim), 20 μM isoleucine, 0.1 mg/ml bovine serum albumin, 20 mM KCl, 10 mM MgCl$_2$, 20 mM β-mercaptoethanol, 4 mM ATP, and 50 mM sodium phosphate (pH 7.5). Host *P. pastoris* lysate was prepared in parallel and assayed as the negative control. Results are shown in FIG. 3.

Equivalents

Those skilled in the art will know, or be able to ascertain using no more than routine experimentation, many equivalents to the specific embodiments of the invention described herein. These and all other equivalents are intended to be encompassed by the following claims.

---

What is claimed is:

1. An isolated nucleic acid which encodes a human mitochondrial isoleucyl-tRNA synthetase.

2. An isolated nucleic acid which encodes at least a portion of a human mitochondrial isoleucyl-tRNA synthetase and which hybridizes to DNA having SEQ ID NO:1 under stringency conditions comprising washing with 0.3 M NaCl, 0.03 M sodium citrate (pH 7.0) and 0.1% SDS at 65° C., wherein the portion has enzymatic activity or binding function.

3. An isolated nucleic acid which encodes an amino acid sequence SEQ ID NO:2.

4. An isolated nucleic acid which encodes a human cytoplasmic isoleucyl-tRNA synthetase.

5. An isolated nucleic acid which encodes at least a portion of a human cytoplasmic isoleucyl-tRNA synthetase and which hybridizes to DNA having SEQ ID NO:3 under stringency conditions comprising washing with 0.3 M NaCl, 0.03 M sodium citrate (pH 7.0) and 0.1% SDS at 65° C., wherein the portion has enzymatic activity or binding function.

6. An isolated nucleic acid which encodes an amino acid sequence SEQ ID NO:4.

7. A recombinant DNA vector comprising DNA which encodes at least a portion of a human mitochondrial isoleucyl-tRNA synthetase and which hybridizes to DNA having SEQ ID NO:1 under stringency conditions comprising washing with 0.3 M NaCl, 0.03 M sodium citrate (pH 7.0) and 0.1% SDS at 65° C., wherein the portion has enzymatic activity or binding function.

8. A recombinant DNA vector comprising DNA which encodes at least a portion of a human cytoplasmic isoleucyl-tRNA synthetase and which hybridizes to DNA having SEQ ID NO:3 under stringency conditions comprising washing with 0.3 M NaCl, 0.03 M sodium citrate (pH 7.0) and 0.1% SDS at 65° C., wherein the portion has enzymatic activity or binding function.

9. An expression vector comprising a nucleic acid encoding a fusion protein comprising a human isoleucyl-tRNA synthetase or a functional portion thereof having enzymatic activity or binding function, wherein said nucleic acid comprises a coding sequence for the human isoleucyl-tRNA synthetase or functional portion of the human isoleucyl-tRNA synthetase, and wherein the coding sequence is under control of transcription signals and is linked to appropriate translation signals for expression in a suitable host cell.

10. A recombinant DNA vector comprising DNA which encodes a human mitochondrial isoleucyl-tRNA synthetase.

11. A recombinant DNA vector comprising DNA which codes for an amino acid sequence SEQ ID NO:2.

12. A recombinant DNA vector comprising DNA which encodes a human cytoplasmic isoleucyl-tRNA synthetase.

13. A recombinant DNA vector comprising DNA which codes for an amino acid sequence SEQ ID NO:4.

14. A host cell which contains a recombinant human isoleucyl-tRNA synthetase gene which expresses a human isoleucyl-tRNA synthetase.

15. A tester strain comprising non-human host cells containing a recombinant human isoleucyl-tRNA synthetase gene or portion thereof which expresses a human isoleucyl-tRNA synthetase or portion thereof having enzymatic activity or binding function.

16. The tester strain of claim 15 in which a host gene encoding an isoleucyl-tRNA synthetase has been altered relative to wild type so as to make no gene product, a gene product which is inactive, or a gene product which can be conditionally made inactive, and in which the recombinant human isoleucyl-tRNA synthetase gene detectably complements the altered host gene.

17. The tester strain of claim 16 in which the host cells are of the species *Saccharomyces cerevisiae*, and in which the host gene is ILS1.

18. A method for producing a recombinant human isoleucyl-tRNA synthetase or functional portion thereof comprising the following steps:
   a) constructing a recombinant DNA vector comprising a coding sequence for at least a portion of a human isoleucyl-tRNA synthetase, wherein the coding sequence is under control of transcription signals and is linked to appropriate translation signals, and wherein the portion has enzymatic activity or binding function;
   b) transforming suitable host cells which support replication of the vector; and
   c) maintaining the host cells under conditions in which human isoleucyl-tRNA synthetase is expressed.

19. A method of producing isolated, recombinant human isoleucyl-tRNA synthetase or a functional portion thereof, comprising the following steps:
   a) providing host cells comprising a recombinant gene encoding human isoleucyl-tRNA synthetase or a functional portion thereof;
   b) maintaining the host cells under conditions in which the gene encoding human isoleucyl-tRNA synthetase or a functional portion thereof is expressed; and
   c) isolating recombinant human isoleucyl-tRNA synthetase or a functional portion thereof from the host cell, wherein the portion has enzymatic activity or binding function.

20. A host cell which contains an expression vector comprising a nucleic acid encoding a fusion protein comprising a human isoleucyl-tRNA synthetase or a functional portion thereof having enzymatic activity or binding function, wherein said nucleic acid comprises a coding sequence for the human isoleucyl-tRNA synthetase or functional portion of the human isoleucyl-tRNA synthetase, and wherein the coding sequence is under control of transcription signals and is linked to appropriate translation signals for expression in the host cell.

21. A host cell comprising recombinant nucleic acid encoding a polypeptide comprising a human cytoplasmic isoleucyl-tRNA synthetase or functional portion thereof having enzymatic activity or binding function.

* * * * *